(12) United States Patent
Kwong et al.

(10) Patent No.: US 9,899,612 B2
(45) Date of Patent: Feb. 20, 2018

(54) ORGANIC ELECTROLUMINESCENT MATERIALS AND DEVICES

(71) Applicant: Universal Display Corporation, Ewing, NJ (US)

(72) Inventors: Raymond Kwong, Plainsboro, NJ (US); Chuanjun Xia, Lawrenceville, NJ (US); Jason Brooks, Philadelphia, PA (US); Bert Alleyne, Ewing, NJ (US); Bin Ma, Plainsboro, NJ (US); James Fiordeliso, Morrisville, PA (US); Yonggang Wu, Ewing, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 840 days.

(21) Appl. No.: 14/295,696

(22) Filed: Jun. 4, 2014

(65) Prior Publication Data

US 2014/0284585 A1   Sep. 25, 2014

Related U.S. Application Data

(60) Division of application No. 12/044,801, filed on Mar. 7, 2008, now Pat. No. 8,778,508, which is a continuation-in-part of application No. PCT/US2007/025353, filed on Dec. 10, 2007, and a continuation-in-part of application No. 11/951,879, filed on Dec. 6, 2007, now Pat. No. 8,119,255.

(60) Provisional application No. 60/940,310, filed on May 25, 2007, provisional application No. 60/873,581, filed on Dec. 8, 2006.

(51) Int. Cl.
| | |
|---|---|
| *H01L 51/54* | (2006.01) |
| *H01L 51/00* | (2006.01) |
| *C07F 15/00* | (2006.01) |
| *C09K 11/06* | (2006.01) |
| *H05B 33/14* | (2006.01) |
| *H01L 51/50* | (2006.01) |

(52) U.S. Cl.
CPC ...... *H01L 51/0085* (2013.01); *C07F 15/0033* (2013.01); *C09K 11/06* (2013.01); *H05B 33/14* (2013.01); *C09K 2211/1029* (2013.01); *C09K 2211/185* (2013.01); *H01L 51/006* (2013.01); *H01L 51/0054* (2013.01); *H01L 51/0071* (2013.01); *H01L 51/0074* (2013.01); *H01L 51/5016* (2013.01); *H01L 51/5088* (2013.01)

(58) Field of Classification Search
None
See application file for complete search history.

(56) References Cited

U.S. PATENT DOCUMENTS

| | | |
|---|---|---|
| 4,769,292 A | 9/1988 | Tang et al. |
| 5,061,569 A | 10/1991 | VanSlyke et al. |
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

(Continued)

*Primary Examiner* — Marie R. Yamnitzky

(74) *Attorney, Agent, or Firm* — Duane Morris LLP

(57) ABSTRACT

Homoleptic organometallic iridium complexes formed from bidentate substitute phenylpyridine ligands are disclosed. Devices containing the homoleptic organometallic iridium complexes that exhibit improved device manufacturing, fabrication, stability, efficiency, and/or color are also disclosed.

8 Claims, 4 Drawing Sheets

(56) References Cited

U.S. PATENT DOCUMENTS

| | | |
|---|---|---|
| 2003/0059646 A1 | 3/2003 | Kamatani et al. |
| 2003/0068536 A1* | 4/2003 | Tsuboyama et al. ............ C07F 15/0033 428/704 |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0127696 A1 | 6/2006 | Stossel et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0128466 A1* | 6/2007 | Nomura et al. ....... C09K 11/06 428/690 |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| WO | 2001039234 | 5/2001 |
| WO | 2002002714 | 1/2002 |
| WO | 200215645 | 2/2002 |
| WO | 2003040257 | 5/2003 |
| WO | 2003060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | WO 2009/030981 A2 * | 3/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Aonuma, Masaki et al., "Material Design of Hole Transport Materials Capable of Thick-Film Formation in Organic Light Emitting Diodes," Appl. Phys. Lett., 90:183503-1-183503-3, (2007).

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

Gao, Zhigiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1, 15-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi et al., "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

(56) References Cited

OTHER PUBLICATIONS

Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18 (21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5'-Bis(dimesitylboryl)-2,2'5",2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., Molecular Organic Glasses for Blue Electroluminescence, Synthetic Metals, 91:209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing $N^\wedge C^\wedge M$-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 87:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Foreign Office Action and Search Report for corresponding Taiwan Application No. 097116553 dated Jun. 23, 2014.

* cited by examiner

ORGANIC ELECTROLUMINESCENT MATERIALS AND DEVICES

CROSS-REFERENCES TO RELATED APPLICATIONS

This application is a divisional application of application Ser. No. 12/044,801, filed Mar. 7, 2008, now U.S. Pat. No. 8,778,508, which is a continuation-in-part application of application Ser. No. 11/951,879, filed Dec. 6, 2007, which is now U.S. Pat. No. 8,119,255 issued on Feb. 21, 2012, which itself claims priority to U.S. Provisional Application Ser. No. 60/873,581, filed Dec. 8, 2006, and Ser. No. 60/940,310, filed May 25, 2007, the disclosures of which are herein expressly incorporated by reference in their entirety. Application Ser. No. 12/044,801 is also a continuation-in-part application of Application No. PCT/US2007/025353, filed Dec. 10, 2007, the disclosure of which is herein expressly incorporated by reference in its entirety. This application is related to PCT International Application No. PCT/US2008/056221, filed Mar. 7, 2008. This application is also related to PCT International Application No. PCT/US2008/056325, filed Mar. 7, 2008.

The claimed invention was made by, on behalf of and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs). More specifically, the present invention relates to light-emitting organometallic materials and devices that may have improved device manufacturing, fabrication, stability, efficiency, and/or color.

BACKGROUND

Opto-electronic devices that make use of organic materials are becoming increasingly desirable for a number of reasons. Many of the materials used to make such devices are relatively inexpensive, so organic opto-electronic devices have the potential fir cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the structure of Formula I:

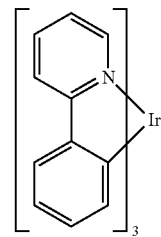

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand is referred to as "photoactive" when it is believed that the ligand contributes to the photoactive properties of an emissive material.

More details on OLEDs, and the definitions described above, can be found in U.S. Pat. No. 7,279,704, which is incorporated herein by reference in its entirety.

SUMMARY OF THE INVENTION

Materials for use in an OLED are provided. The materials are a 2-phenylpyridine iridium (Irppy) complex having alkyl and/or aryl substituted ligands and a heteroleptic or a homoleptic nature. These materials may be advantageously used in OLEDs.

The materials have a heteroleptic iridium compound having the formula:

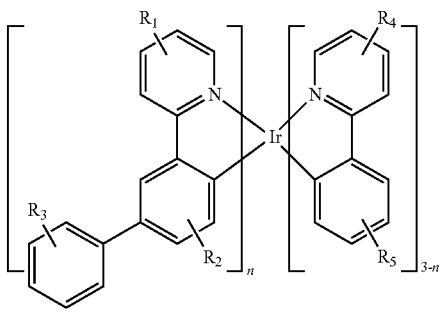

wherein n=1 or 2;
$R_1$, $R_2$, $R_3$, $R_4$ and $R_5$ are independently selected from the group consisting of hydrogen, alkyl and aryl, and where each of $R_1$, $R_2$, $R_3$, $R_4$ and $R_5$ may represent mono, di, tri, tetra, or penta substitutions; and
at least one of $R_1$, $R_2$, $R_3$, $R_4$ and $R_5$ is alkyl or aryl.

In one aspect, the materials have a heteroleptic iridium compound having the formula:

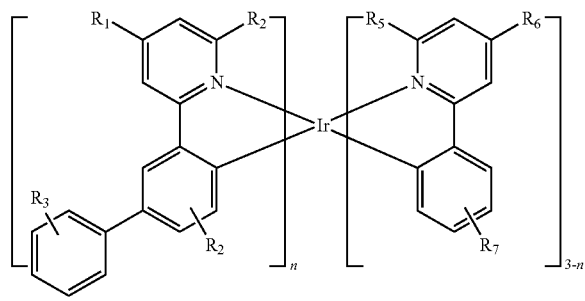

wherein n=1 or 2;
$R_1$, $R_2$, $R_5$ and $R_6$ are independently selected from the group consisting of hydrogen, alkyl and aryl;
at least one of $R_1$, $R_2$, $R_5$ and $R_6$ is alkyl or aryl; and
$R_3$, $R_4$ and $R_7$ are independently selected from the group consisting of hydrogen, alkyl and aryl, and where $R_3$, $R_4$ and $R_7$ may represent mono, di, tri, tetra or penta substitutions.

In another aspect, the materials have a heteroleptic iridium compound having the formula:

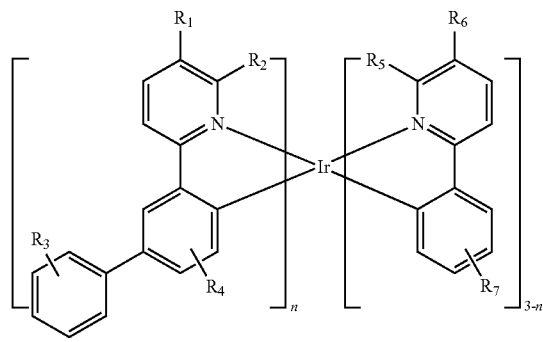

wherein n=1 or 2;
$R_1$, $R_2$, $R_5$ and $R_6$ are independently selected from the group consisting of hydrogen, alkyl and aryl;
at least one of $R_1$, $R_2$, $R_5$ and $R_6$ is alkyl or aryl; and
$R_3$, $R_4$ and $R_7$ are independently selected from the group consisting of hydrogen, alkyl and aryl, and where each of $R_3$, $R_4$ and $R_7$ may represent mono, di, tri, tetra or penta substitutions.

In another aspect, the materials have a heteroleptic iridium compound having the formula:

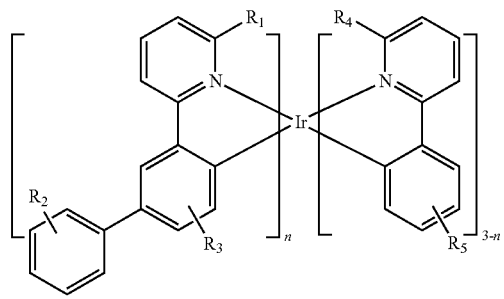

wherein n=1 or 2;
$R_1$ and $R_4$ are independently selected from the group consisting of hydrogen, alkyl, and aryl;
at least one of $R_1$ and $R_4$ is alkyl or aryl; and
$R_2$, $R_3$ and $R_5$ are independently selected from the group consisting of hydrogen, alkyl, and aryl, and where each of $R_2$, $R_1$ and $R_5$ may represent mono, di, tri, tetra or penta substitutions.

In another aspect, the materials have a heteroleptic iridium compound having the formula:

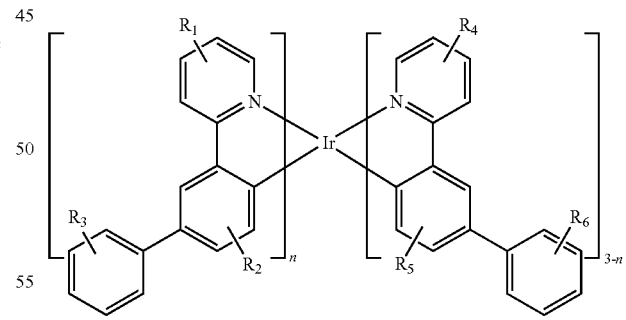

wherein n=1 or 2;
$R_1$, $R_2$, $R_3$, $R_4$, $R_5$ and $R_6$ are independently selected from the group consisting of hydrogen, alkyl, and aryl, and where each of $R_1$, $R_2$, $R_3$, $R_4$, $R_5$ and $R_6$ may represent mono, di, tri, tetra or penta substitutions;
at least one of $R_1$, $R_2$, $R_3$, $R_4$, and $R_5$ is alkyl or aryl; and
at least $R_1$ is different from $R_4$, $R_2$ is different from $R_5$, or $R_3$ is different from $R_6$.

In another aspect, the materials have a homoleptic iridium compound selected from the group consisting of:
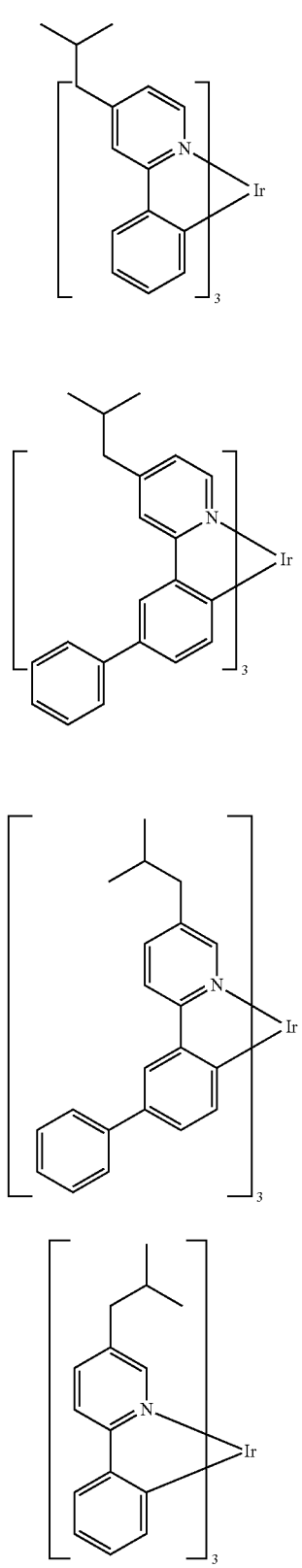
Compound 1
Compound 4
Compound 5
Compound 7
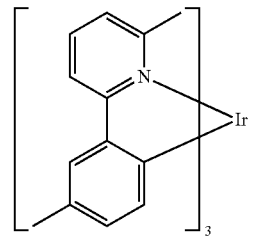
Compound 9
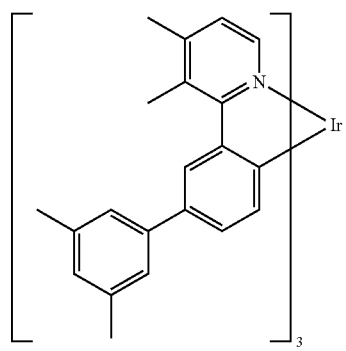
Compound 13
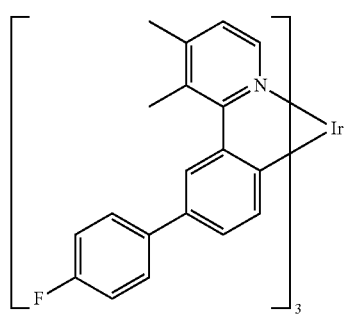
Compound 14
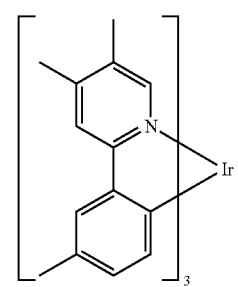
Compound 15
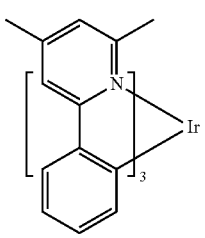
Compound 16

Compound 17
Compound 19
Compound 20
Compound 21
Compound 22
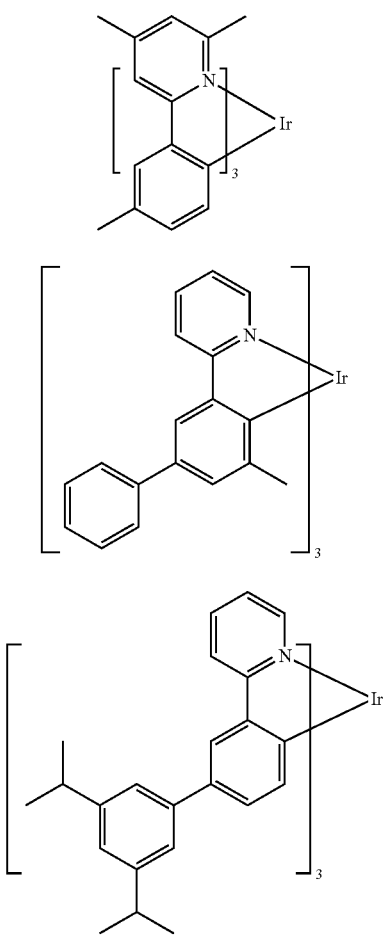
Compound 23
Compound 24
Compound 28
Compound 29
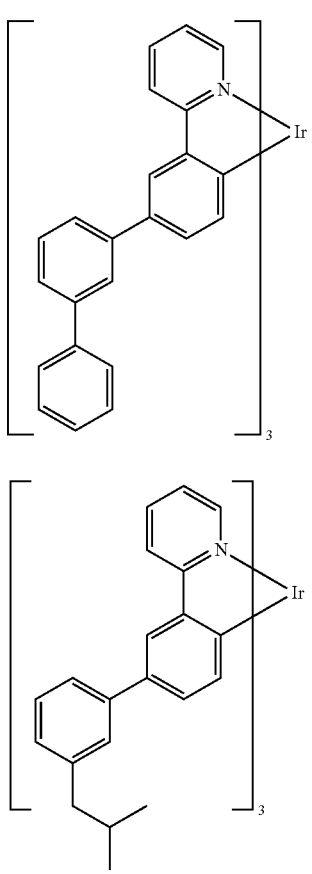
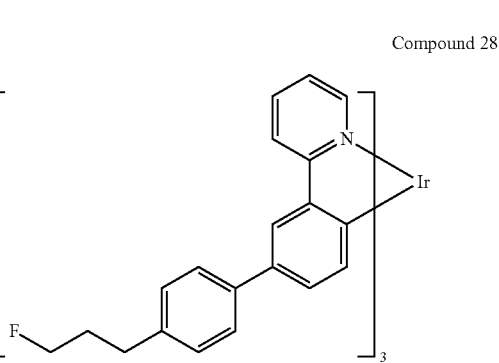
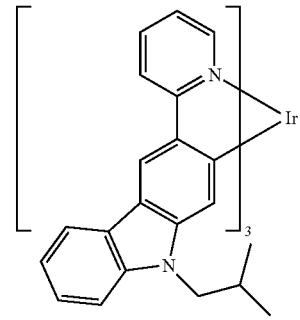

Compound 30

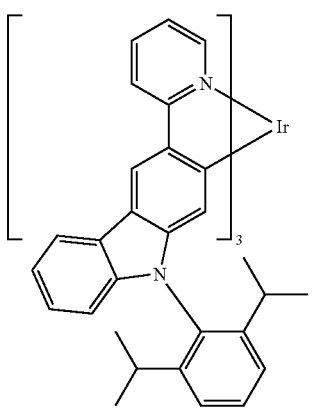

Compound 31

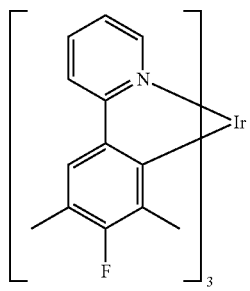

Compound 32

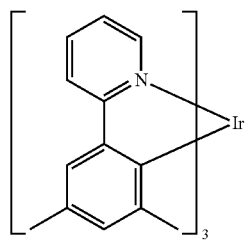

Compound 33

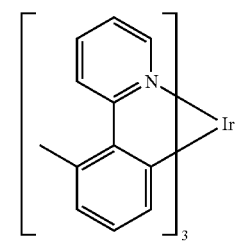

Compound 34

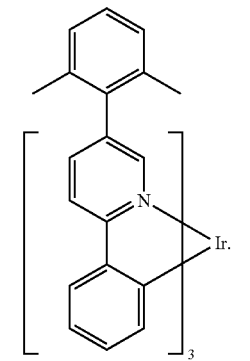

In another aspect, the materials have a compound including a ligand selected from the group described below wherein the ligand is coordinated to a metal having an atomic number greater than 40.

Additionally, an organic light emitting device is provided. The device comprises an anode, a cathode and an organic emissive layer, disposed between the anode and the cathode, the organic layer further comprises an emissive dopant, wherein a compound as described above is the emissive dopant. The organic emissive layer further comprises a host. Particular devices containing a specific host and a specific dopant are provided.

A process is provided for making an $Ir(L_a)(L_b)(L_c)$ complex in improved yields, comprising reacting an intermediate having the formula $(L_a)(L_b)IrX$ with $L_c$ to produce a $Ir(L_a)(L_b)(L_c)$ complex, where $L_a$, $L_b$ and $L_c$ are photoactive and independently bidentate cyclometallated ligands having the formula:

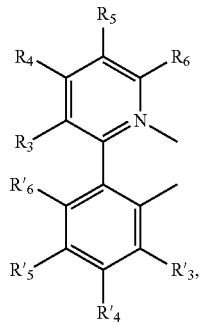

where $R_3$, $R_4$, $R_5$, $R_6$, $R'_3$, $R'_5$, and $R'_6$ are independently selected from the group consisting of hydrogen, alkyl, alkenyl, alkynyl, alkylaryl, CN, $CO_2R$, C(O)R, $NR_2$, $NO_2$, OR, halo, aryl, heteroaryl, substituted aryl, substituted heteroaryl, or a heterocyclic group;

where at least one of $R_6$ or $R'_3$ is not hydrogen, and $R_6$ or $R'_3$ is selected from the group consisting of alkyl, alkenyl, alkynyl, alkylaryl, CN, $CO_2R$, C(O)R, $NR_2$, $NO_2$, OR, halo, a heteroaryl, substituted aryl, substituted heteroaryl, and a heterocyclic group; and X is

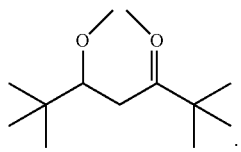

DETAILED DESCRIPTION

Generally, an OLED comprises at least one organic layer disposed between and electrically connected to an anode and a cathode. When a current is applied, the anode injects holes and the cathode injects electrons into the organic layer(s).

The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-15.4, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Phosphorescence from triplets can be enhanced over fluorescence by confining, preferably through bonding, the organic molecule in close proximity to an atom of high atomic number. This phenomenon, called the heavy atom effect, is created by a mechanism known as spin-orbit coupling. Such a phosphorescent transition may be observed from an excited metal-to-ligand charge transfer (MLCT) state of an organometallic molecule such as tris(2-phenylpyridine)iridium(III).

Figure 1:
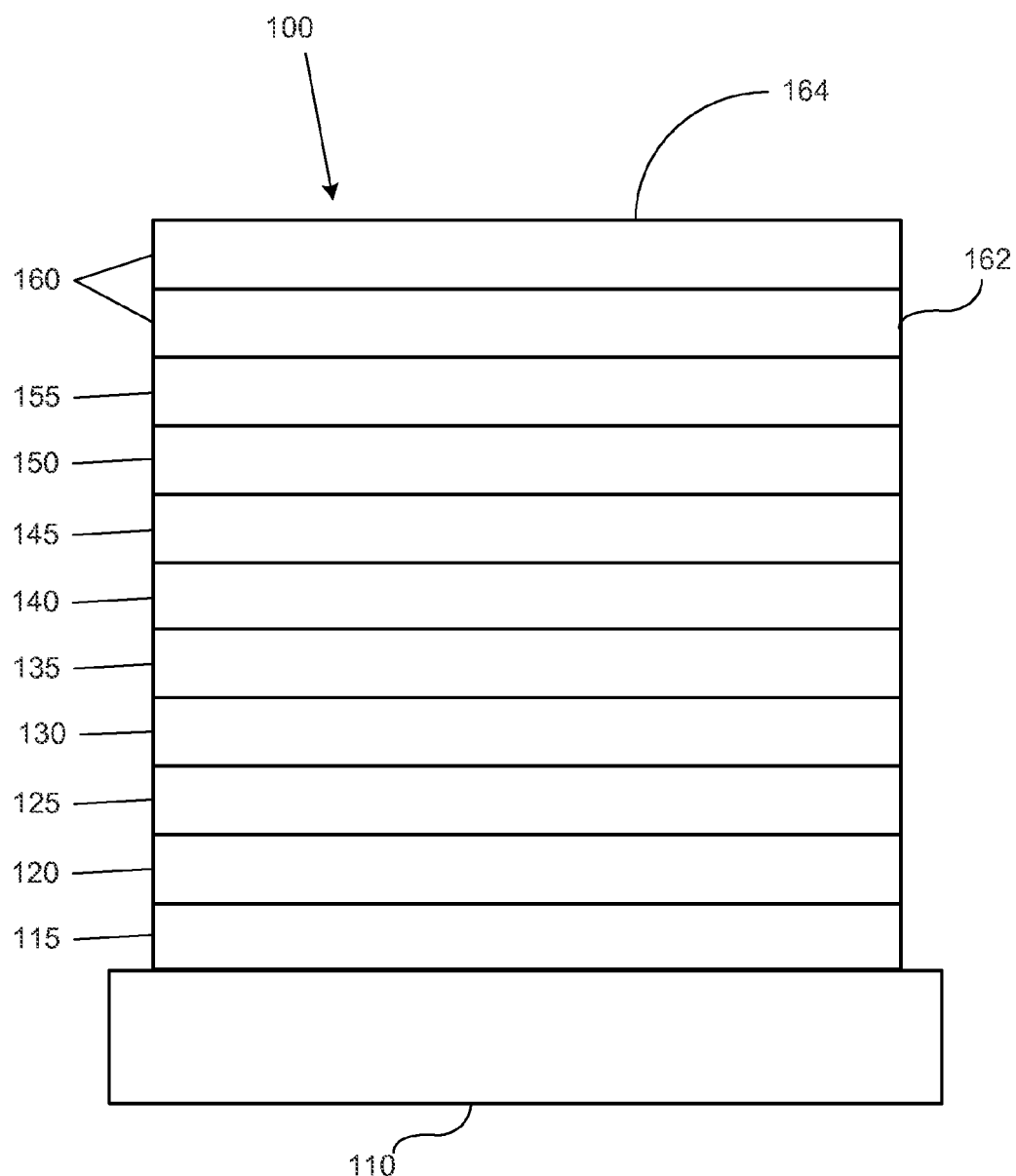
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.stib.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
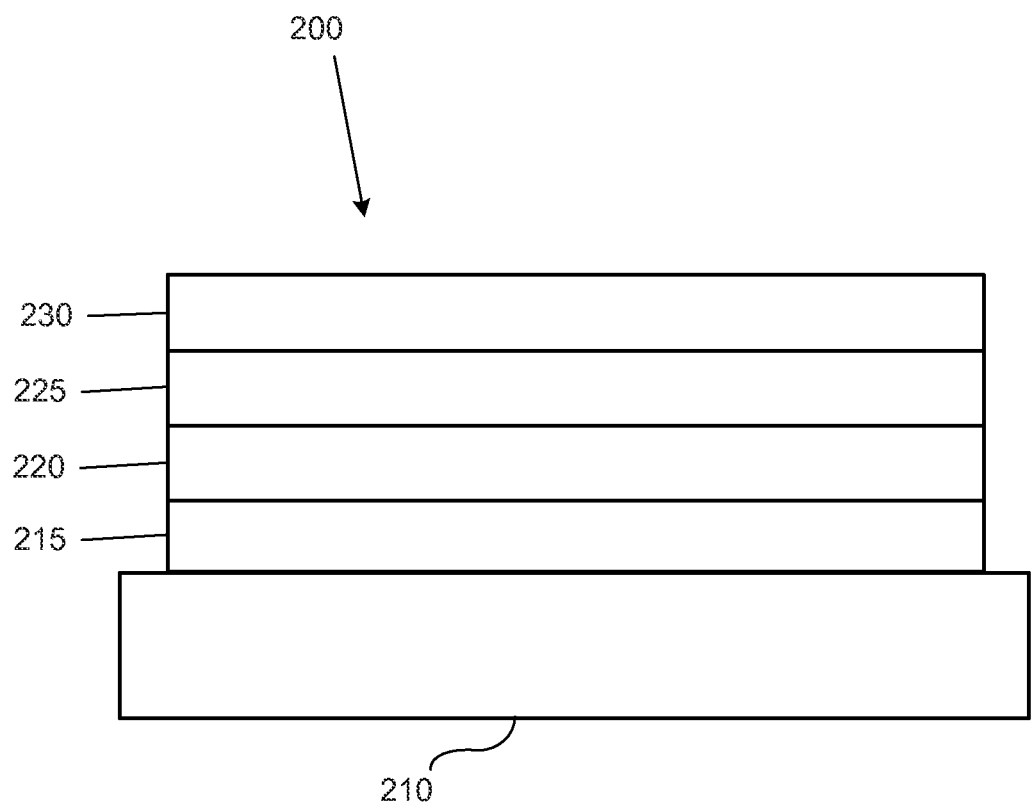
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED, Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, inkjet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, now U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Compounds are provided, comprising a tris Ir(III) complex having a photoactive sterically demanding cyclometallated ligand. The advantage of using ligands with substituents such as alkyl and aryl groups is that they offer luminescence and device property tuning with a small impact on device operation stability. Particularly, aryl and alkyl substituted ligands incorporated into tris complexes may be used to achieve devices with high efficiency and high stability. See Kwong et al., *Complexes with phenylpyridine derivatives and their use in organic light-emitting devices,* 2006, WO2006/014599 and Kwong et al., *Stable and efficient electroluminescent materials,* 2006, WO 2006/014599 A2.

Many cyclometallating ligands that could be incorporated into Ir-based phosphors do not give tris-ligand complexes by the reported synthetic methods. In many situations, tris-ligand complexes are significantly advantageous over a complex having two cyclometallated ligands and a single, bidentate or two monodentate ancillary ligands as phosphorescent materials. Without being bound by theory, it is thought that the bond between the Ir and the cyclometallated ligand is less labile, meaning that it cannot be displaced as easily, leading to improved luminescence efficiency. See Larnansky et al., *Synthesis and Characterization of Cyclometallated iridium Complexes,* Inorg. Chem., 40:1704-1711, 2001 and Kwong et al., *Organic Light Emitting Devices having Reduced Pixel Shrinkage,* col. 16, ln. 45-60, 2006, U.S. Pat. No. 7,087,321 B2. Therefore, it is highly desirable to provide a process for making Ir(III) complexes having photoactive ligands of choice for use in OLEDs in improved yields. The synthesis is particularly difficult for emissive Ir(III) complexes having the formula:

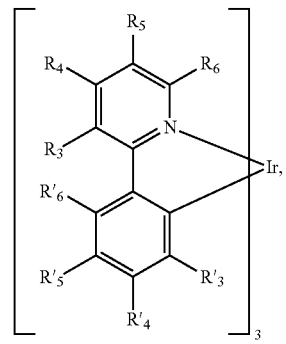

where $R_3$, $R_4$, $R_5$, $R_6$, $R'_3$, $R'_4$, $R'_5$, and $R'_6$ are independently selected from the group consisting of hydrogen, alkyl, alkenyl, alkynyl, alkylaryl, CN, $CO_2R$, $C(O)R$, $NR_2$, $NO_2$, OR, halo, aryl, heteroaryl, substituted aryl substituted heteroaryl and a heterocyclic group; and where at least one of $R_6$ and $R'_3$ is not hydrogen, and $R_6$ and $R'_3$ is selected from the group consisting of alkyl, alkenyl, alkynyl, alkylaryl, CN, $CO_2R$, $C(O)R$, $NR_2$, $NO_2$, OR, halo, aryl, heteroaryl, substituted aryl substituted heteroaryl and a heterocyclic group. Due to the steric congestion of multiple and/or $R'_3$ near the Ir in the final tris cyclometallated Ir complex, direct complexation of the cyclometallated ligand with $Ir(acac)_3$ may result in very low yield (~10%) of the desired product. See Kwong et al., *Complexes with phenylpyridine derivatives and their use in organic light-emitting devices.* 2006, WO2006/014599. A scheme of the current route is illustrated below:

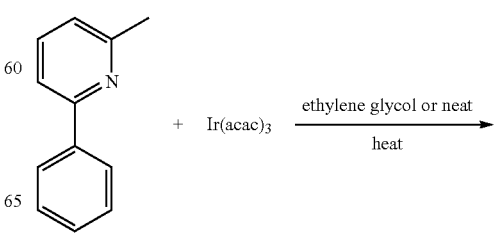

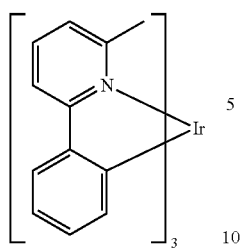

This reaction is reported to have 5.4% yield.

The complexes provided having alkyl and/or aryl substitutions may be of a homoleptic or heteroleptic nature, which can be used in PHOLED devices, giving stable and efficient devices with more saturated color. These materials may be advantageously used as an emissive dopant in PHOLED devices. Heteroleptic complexes may be advantageous in some situations because of the desirable properties imparted by the different ligands. For example, consider a first device containing $Ir(L_1)_3$ as the emitter compared to a second device containing $Ir(L_2)_3$ as the emitter, where the first device is more stable and both devices emit similar colors. But if $L_1$ has a higher molecular weight then $L_2$, then $Ir(L_1)_3$ would require a higher vacuum evaporation temperature then $Ir(L_2)_3$, thus reducing the attractiveness of using $Ir(L_1)_3$. In this case, a heteroleptic $Ir(L)(L_2)_2$ or $Ir(L_1)_2(L_2)$ complex may possess desirable features that are imparted by each ligand (i.e. $L_1$ imparts good stability, while $L_2$ imparts reduced molecular weight and lower evaporation temperature). Also, in another situation, if $Ir(L_1)_3$ is insoluble whereas $Ir(L_2)_3$ is soluble in most organic solvents, $Ir(L_1)_3$ could not be used in solution-based device fabrication methods such as inkjet printing. In this case, a heteroleptic $Ir(L_1)(L_2)_2$ or $Ir(L_1)_2(L_2)$ complex may possess both good stability (as imparted by $L_1$) and good solubility (as imparted by $L_2$). Heteroleptic complexes with asymmetric structures may have better solution processability than those homoleptic structures having symmetric structures, because asymmetric materials may have a lower tendency to recrystallize. Therefore, heteroleptic compounds compared to homoleptic compounds may provide devices with improved manufacturing, fabrication, stability, efficiency, and/or color.

Figure 3:
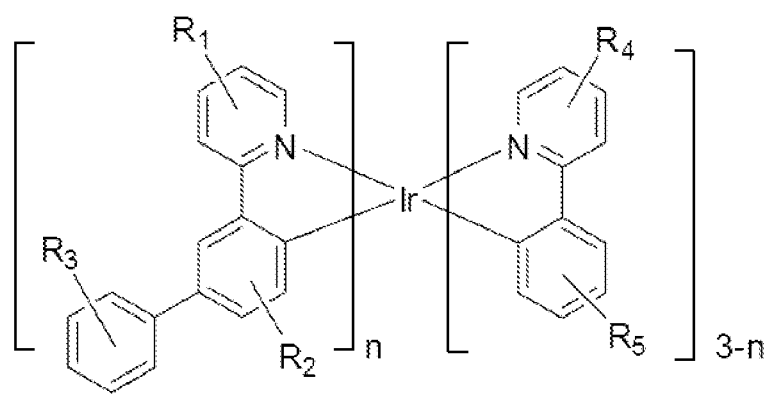
FIG. 3 shows an iridium complex.

As shown in FIG. 3, heteroleptic compounds are provided, which may be advantageously used in OLEDs, having the formula:

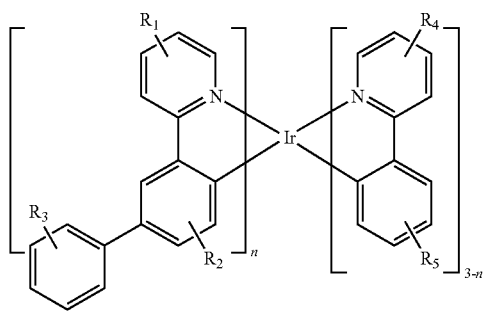

wherein n=1 or 2;
$R_1$, $R_2$, $R_3$, $R_4$ and $R_5$ are independently selected from the group consisting of hydrogen, alkyl and aryl, and where each of $R_1$, $R_2$, $R_3$, $R_4$ and $R_5$ may represent mono, di, tri, tetra, or penta substitutions; and
at least one of $R_1$, $R_2$, $R_3$, $R_4$ and $R_5$ is alkyl or aryl.

Particular heteroleptic compounds, which may be advantageously used in OLEDs, are provided:

Compound 2

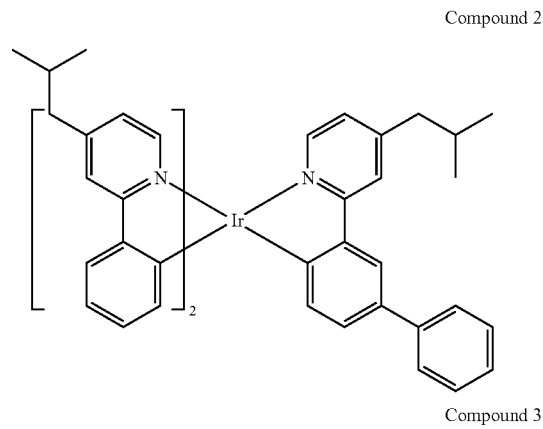

Compound 3

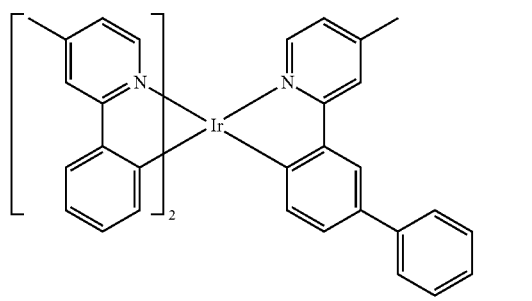

Compound 6

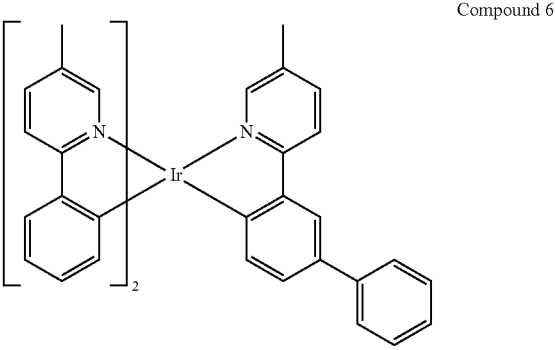

Compound 8

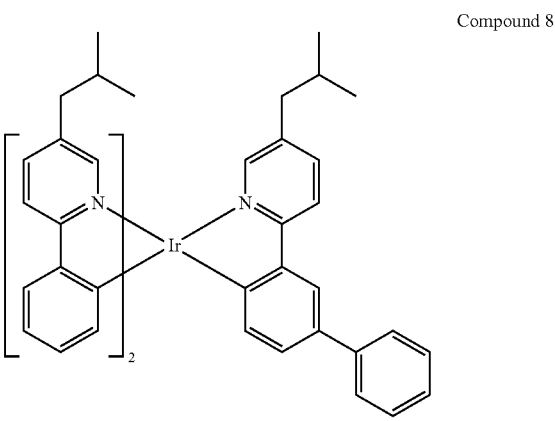

Compound 10
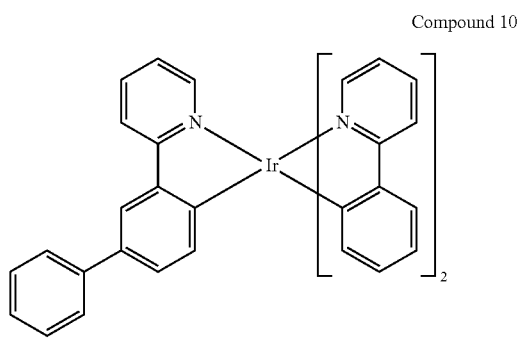
Compound 11
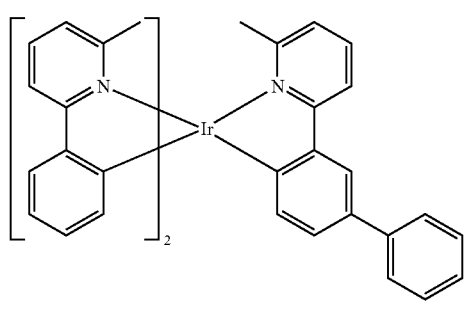
Compound 12
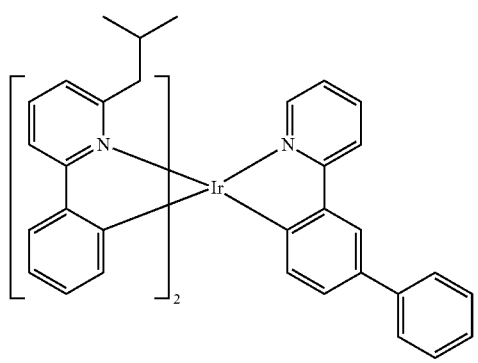
Compound 18
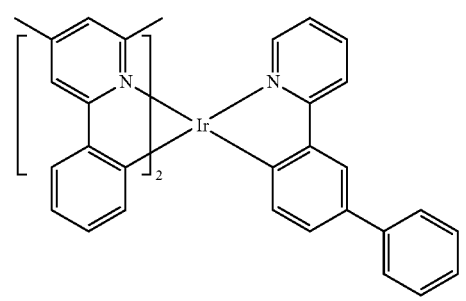
Compound 25
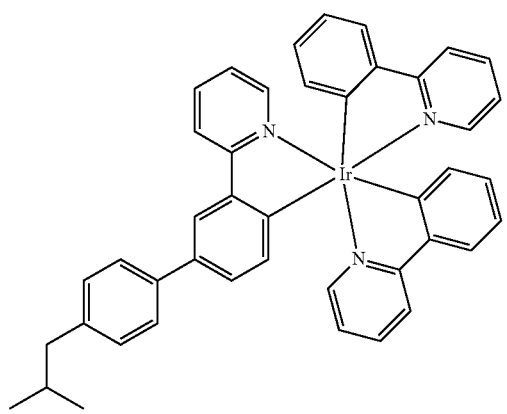
Compound 26
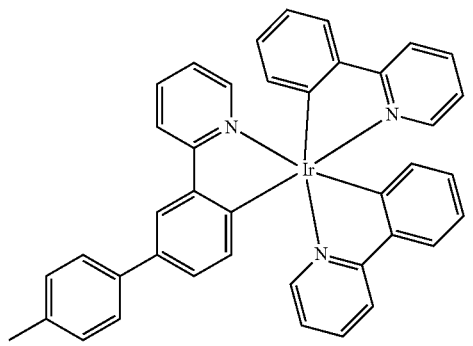
Compound 27
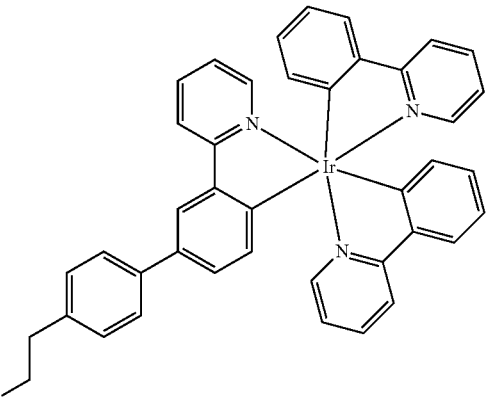
Compound 35
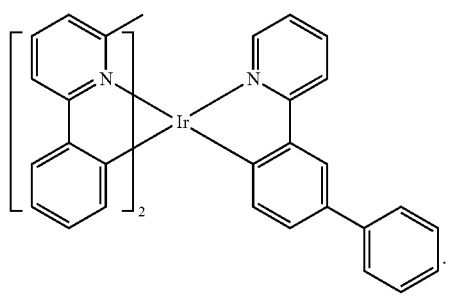
Additionally, heteroleptic compounds are provided, which may be advantageously used in OLED devices, having the formula:

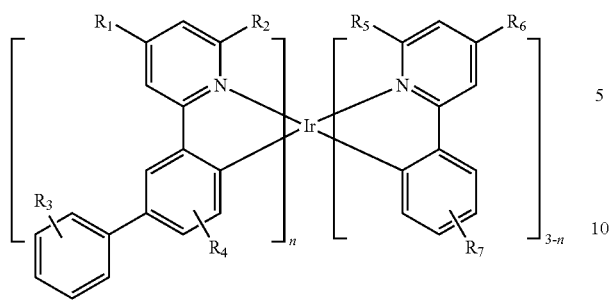

wherein n=1 or 2;

$R_1$, $R_2$, $R_5$ and $R_6$ are independently selected from the group consisting of hydrogen, alkyl and aryl;

at least one of $R_1$, $R_2$, $R_5$ and $R_6$ is alkyl or aryl; and $R_3$, $R_4$ and $R_7$ are independently selected from the group consisting of hydrogen, alkyl and aryl, and where $R_3$, $R_4$ and $R_7$ may represent mono, di, tri, tetra or penta substitutions.

Particular heteroleptic compounds, which may be advantageously used in OLEDs, are provided:

Compound 2

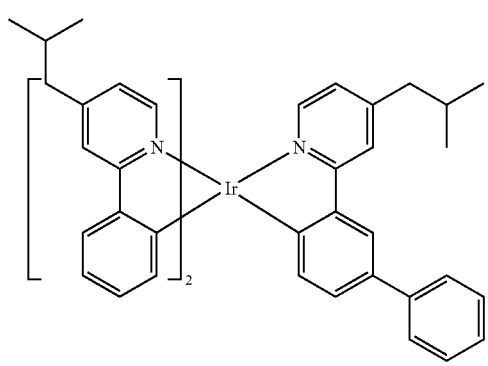

Compound 3

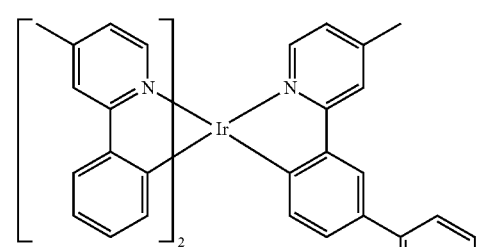

Compound 10

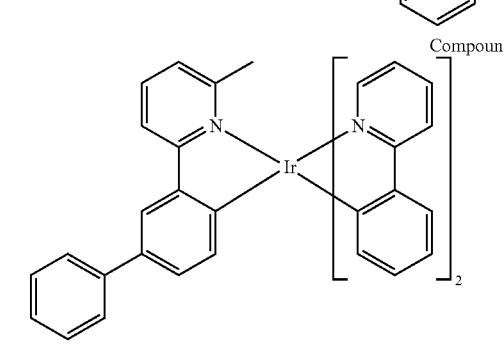

Compound 11

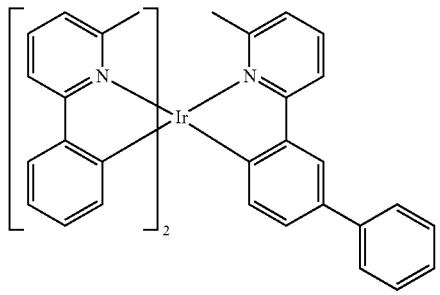

Compound 12

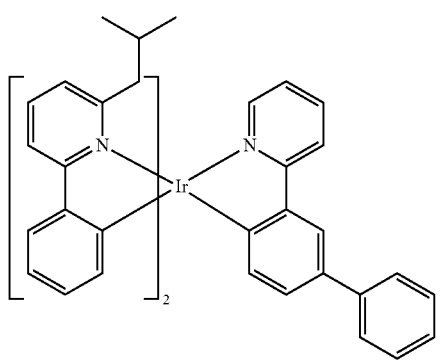

Compound 18

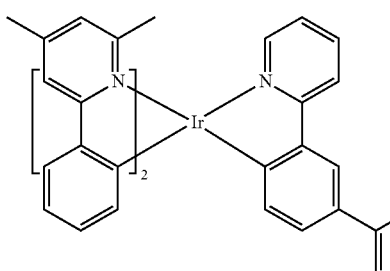

Compound 35

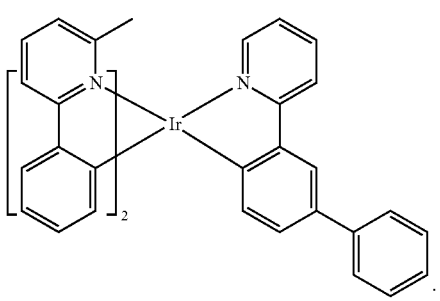

Additionally, heteroleptic compounds are provided, which may be advantageously used in OLED devices, having the formula:

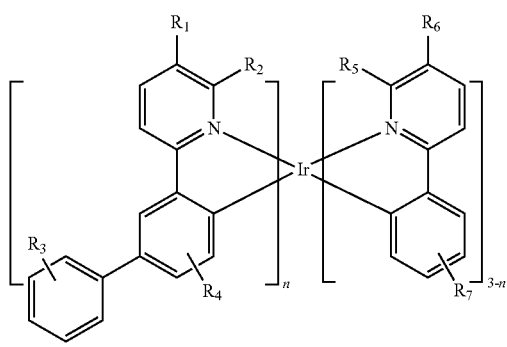

wherein n=1 or 2;

$R_1$, $R_2$, $R_5$ and $R_6$ are independently selected from the group consisting of hydrogen, alkyl and aryl;

at least one of $R_1$, $R_2$, $R_5$ and $R_6$ is alkyl or aryl; and $R_3$, $R_4$ and $R_7$ are independently selected from the group consisting of hydrogen, alkyl and aryl, and where each of $R_3$, $R_4$ and $R_7$ may represent mono, di, tri, tetra or penta substitutions.

Particular heteroleptic compounds, which may be advantageously used in OLEDs, are provided:

Compound 6

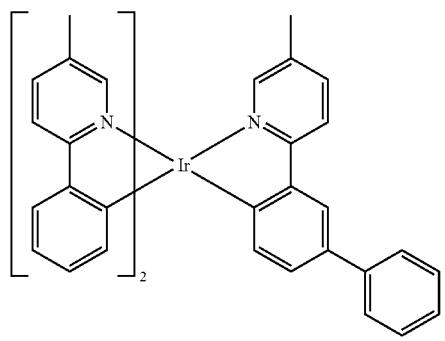

Compound 8

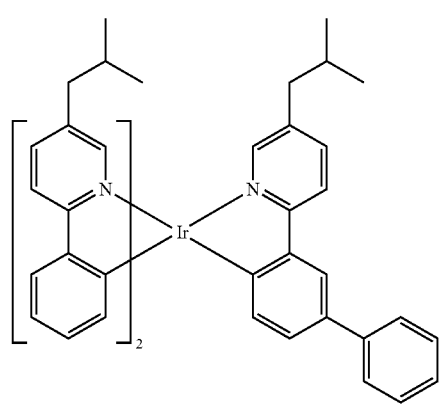

Compound 10

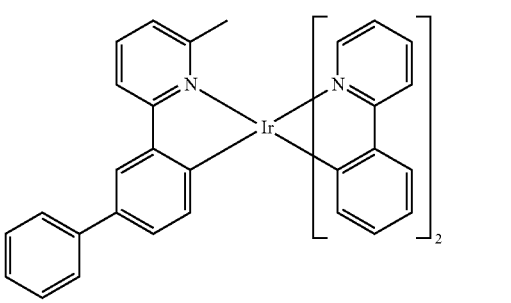

Compound 11

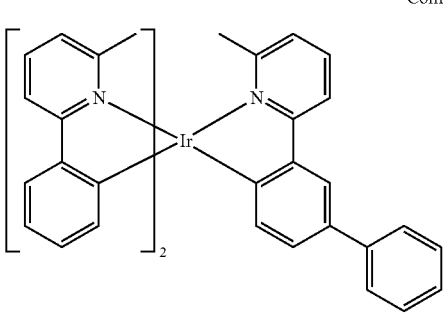

Compound 12

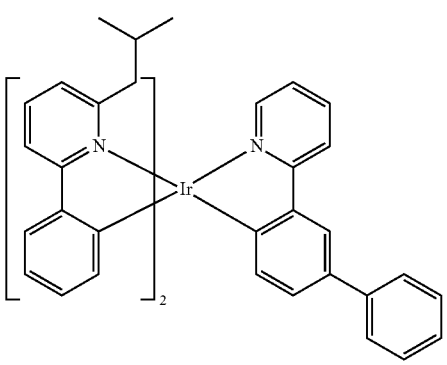

Compound 18

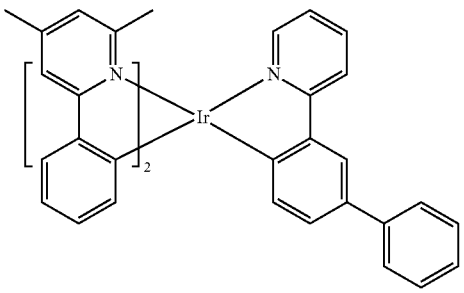

Compound 35

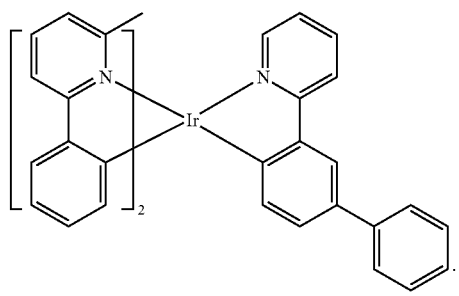

Additionally, heteroleptic compounds are provided, which may be advantageously used in OLED devices, having the formula:

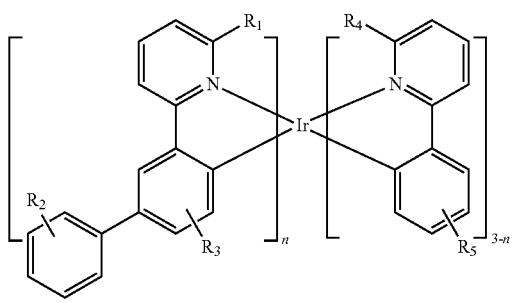

wherein n=1 or 2;

R$_1$ and R$_4$ are independently selected from the group consisting of hydrogen, alkyl, and aryl;

at least one of R$_1$ and R$_4$ is alkyl or aryl; and

R$_2$, R$_3$ and R$_5$ are independently selected from the group consisting of hydrogen, alkyl, and aryl, and where each of R$_2$, R$_3$ and R$_5$ may represent mono, di, tri, tetra or penta substitutions.

Particular heteroleptic compounds, which may be advantageously used in OLEDs, are provided:

Compound 10

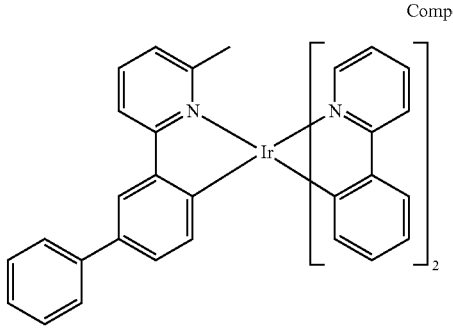

Compound 11

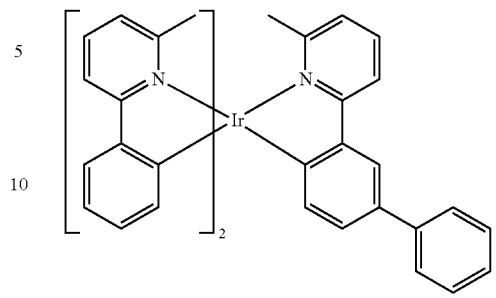

Compound 12

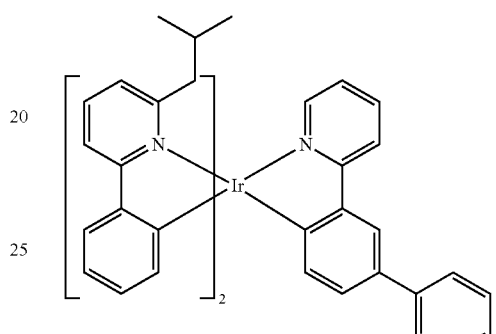

Compound 35

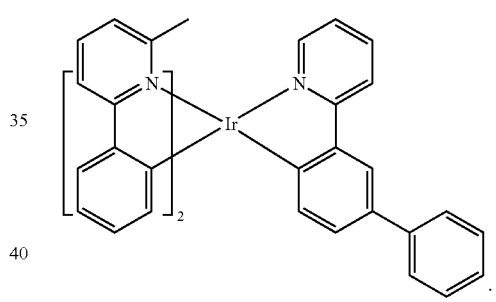

Additionally, heteroleptic compounds are provided, which may be advantageously used in OLED devices, having the formula:

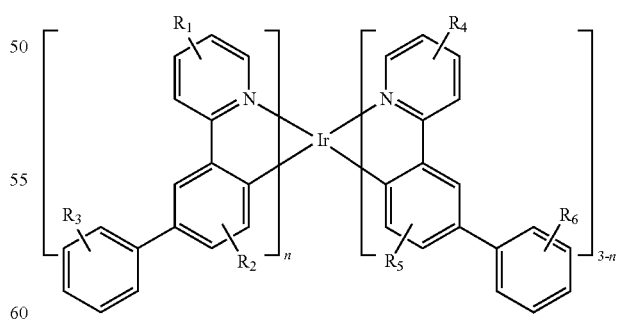

wherein n=1 or 2;

R$_1$, R$_2$, R$_3$, R$_4$, R$_5$ and R$_6$ are independently selected from the group consisting of hydrogen, alkyl, and aryl, and where each of R$_1$, R$_2$, R$_3$, R$_4$, R$_5$ and R$_6$ may represent mono, di, tri, tetra or penta substitutions;

at least one of $R_1$, $R_2$, $R_3$, $R_4$, and $R_5$ is alkyl or aryl; and at least $R_1$ is different from $R_4$, $R_2$ is different from $R_5$, or $R_3$ is different from $R_6$.

Particular heteroleptic compounds, which may be advantageously used in OLEDs, are provided:

Compound 36

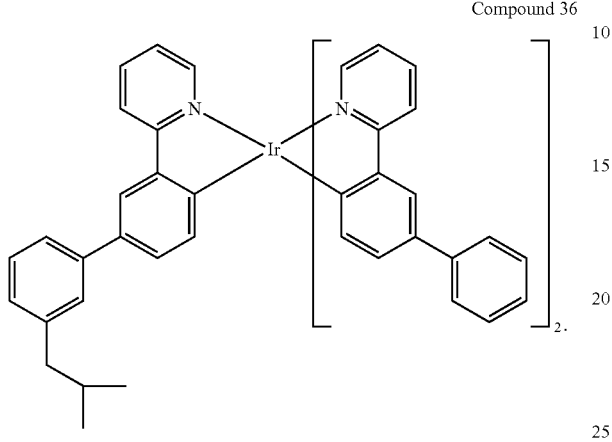

Additionally, particular homoleptic compounds are provided, which may be advantageously used in OLEDs, having the structures:

Compound 1

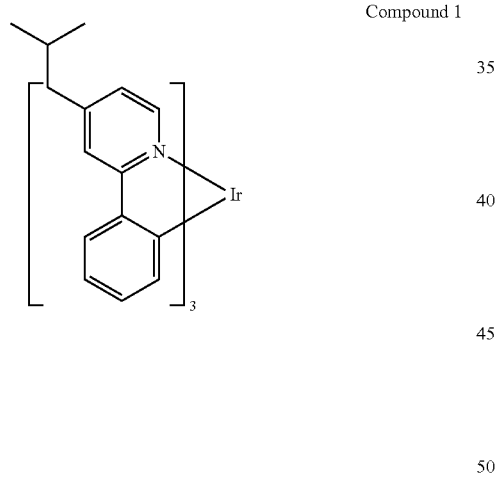

Compound 4

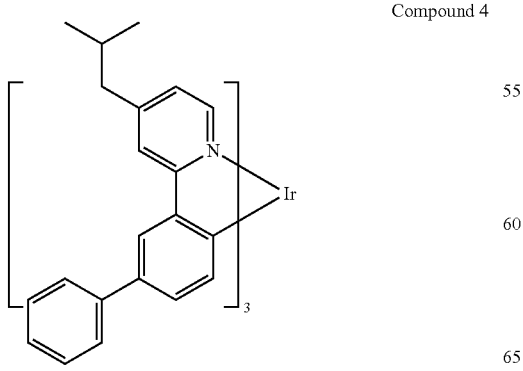

Compound 5

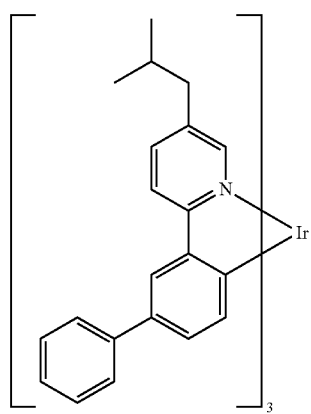

Compound 7

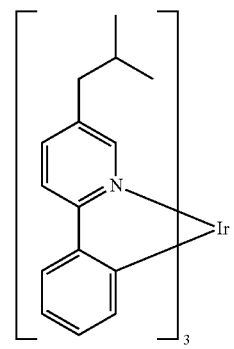

Compound 9

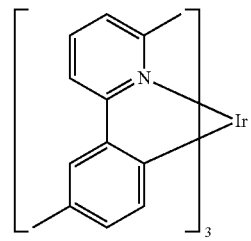

Compound 13

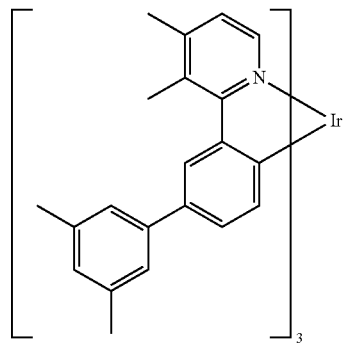

Compound 14
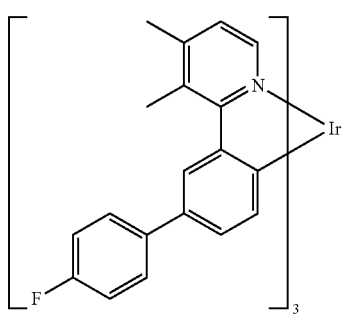
Compound 15
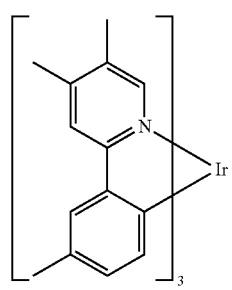
Compound 16
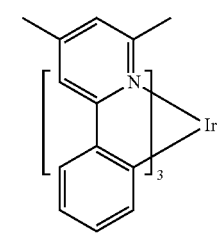
Compound 17
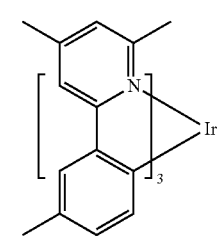
Compound 19
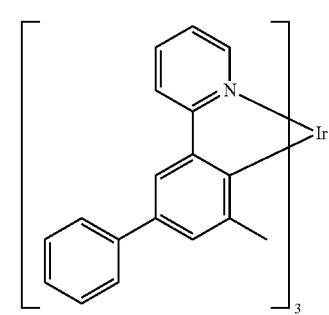
Compound 20
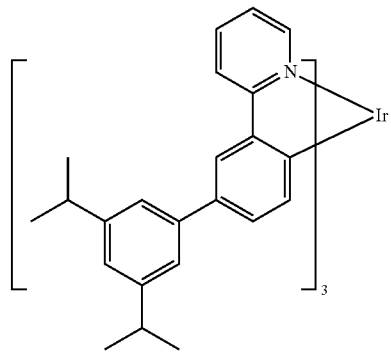
Compound 21
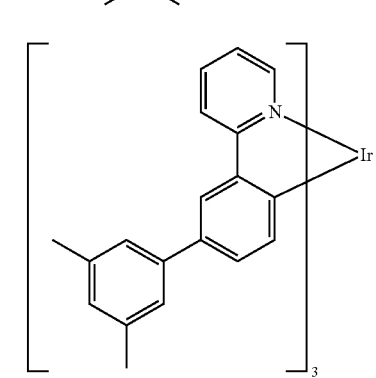
Compound 22
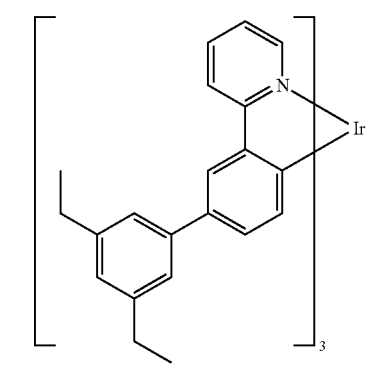
Compound 23
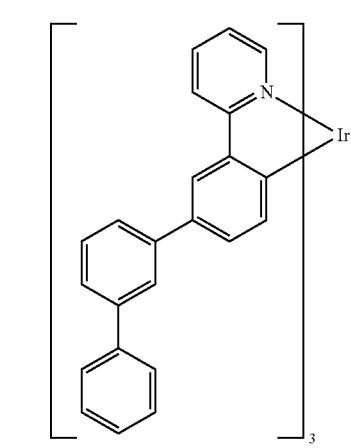

Compound 24
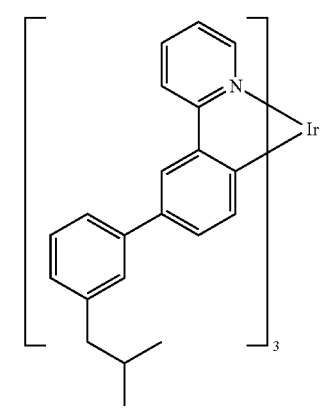
Compound 28
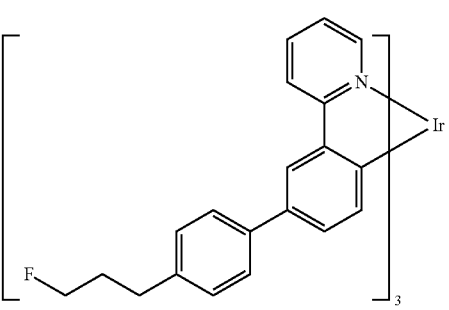
Compound 29
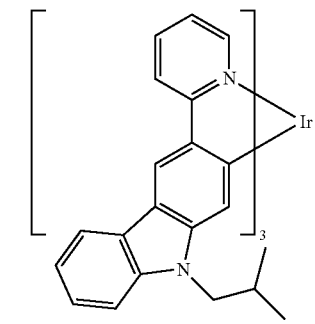
Compound 30
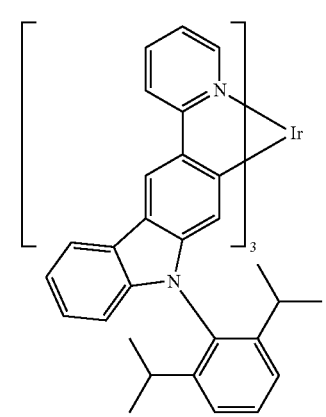
Compound 31
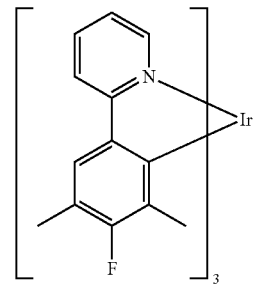
Compound 32
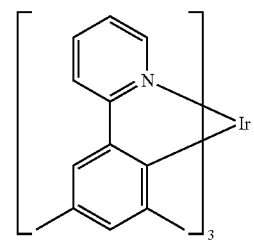
Compound 33
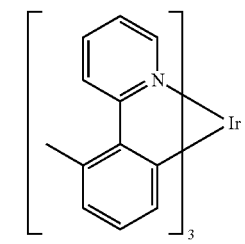
Compound 34
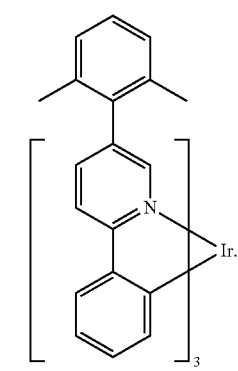
Additionally, compounds are provided where the compounds include a ligand selected from the group consisting of:
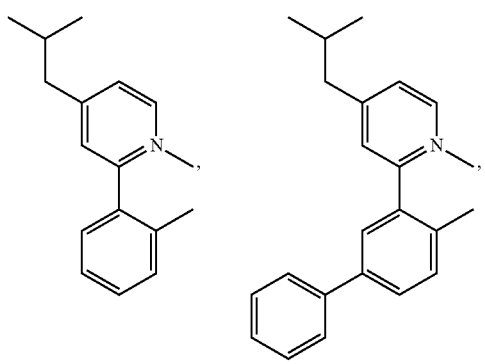

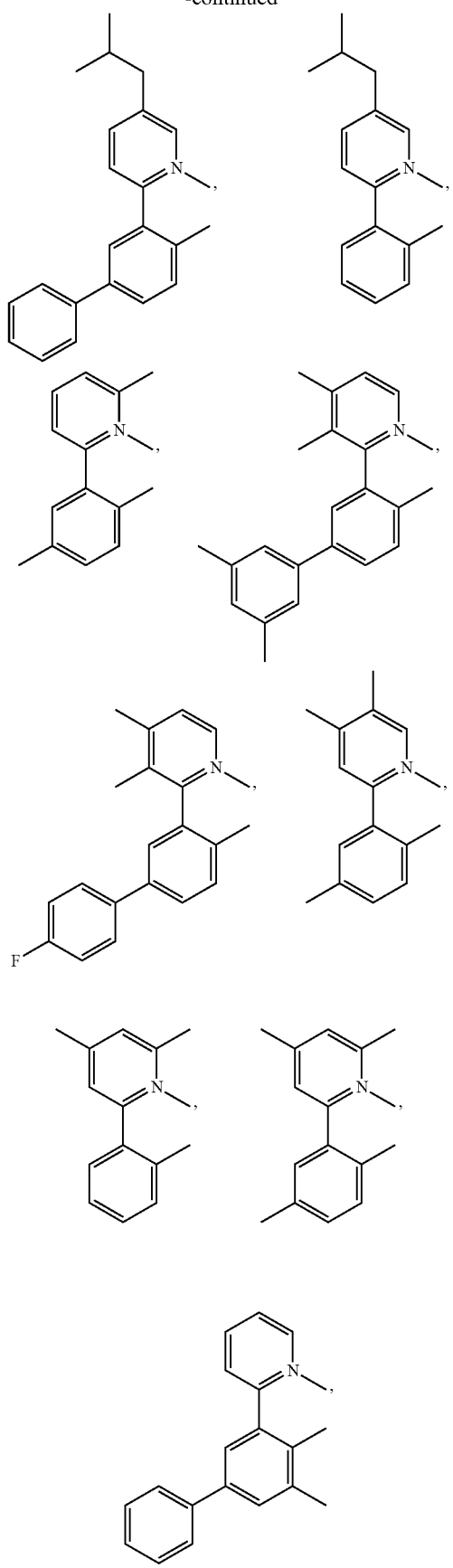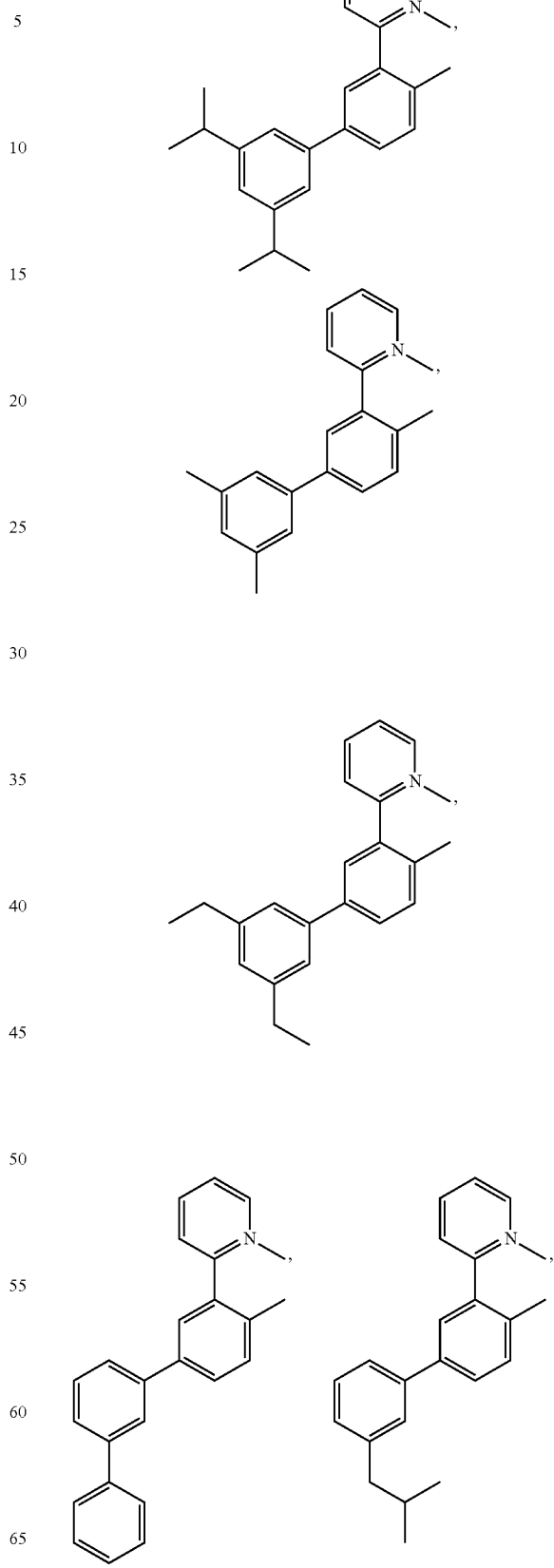

-continued

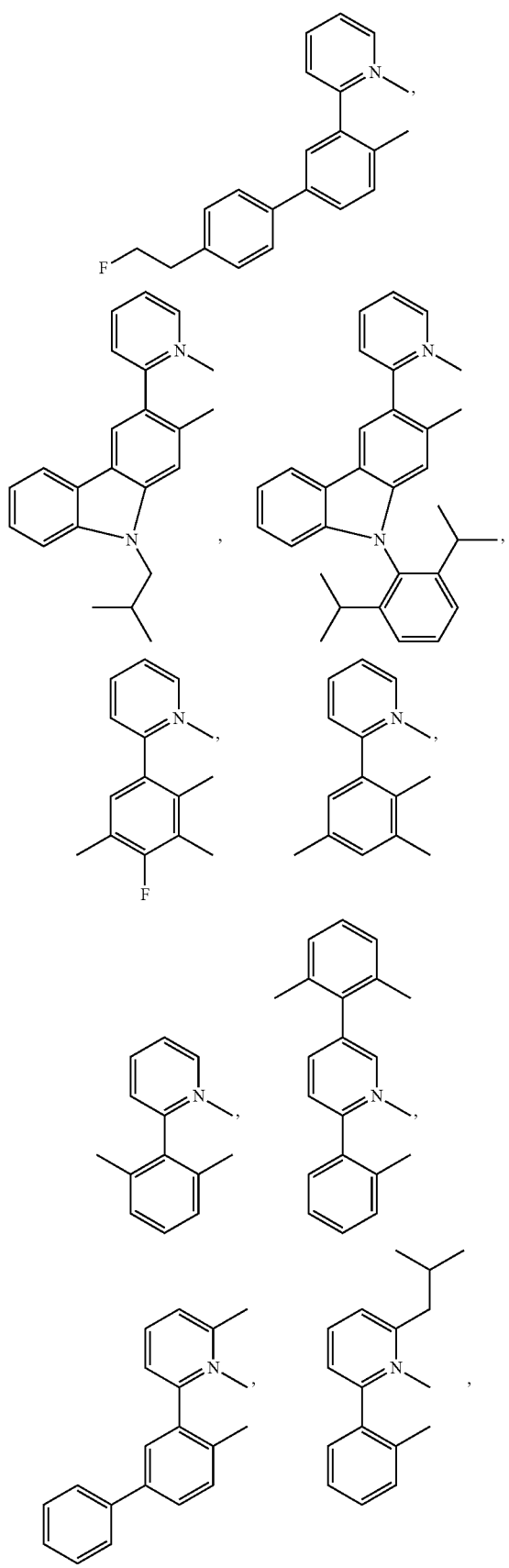

-continued

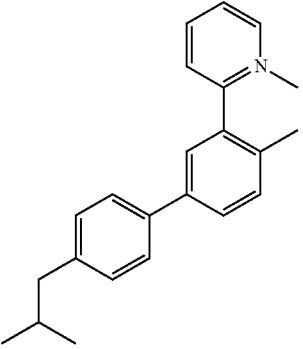

wherein the ligand is coordinated to a metal having an atomic number greater than 40. Preferably, the metal is iridium.

Additionally, an organic light emitting device is provided. The device comprises an anode, a cathode and an organic emissive layer, disposed between the anode and the cathode, the organic layer further comprises an emissive dopant, wherein a compound as described above is the emissive dopant. The organic emissive layer further comprises a host, wherein the host is a compound containing a carbazole group, triphenylene group or dibenzothiophene group. Specifically, the host is Compound H or Compound G.

Particular devices are provided wherein Compound 11 or Compound 35 is the emissive dopant and Compound H or Compound G is the host.

Particular emissive dopants for the emissive layer of an OLED are also provided which may lead to devices having particularly good properties. Specifically, devices having an emissive layer using Compounds 25 or 26 as the emissive dopant as shown in Table 1. Devices using Compound 25 and 26 respectively as emitters show improved device stability indicating to that alkylphenyl substitutions may be beneficial. Cmpd. is an abbreviation of Compound.

The alkyl substitution on the 5'-phenyl can be used to tune evaporation temperature and solubility, narrow emission, and increase device efficiency. The heteroleptic nature of Compounds 25 and 26, with only one of the 2-phenylpyridine substituted keeps the evaporation temperature low as shown in Table 1, which is important for OLED manufacturing because prolonged heating of the materials is needed, and low evaporation temperature translates to less thermal stress which typically results in cleaner evaporations. The alkyl substitution on the 5'-phenyl can also increase solubility as shown in Table 1, which is critical in device fabrication based on solution processes, such as inkjet printing. 5' alkylphenyl may also narrow emission which is preferred in OLED for display application because more saturated color can be achieved. In addition, devices using Compounds 25 and 26 demonstrate that using heteroleptic complexes may offer high device efficiency.

Similarly, devices having an emissive layer using heteroleptic Compounds 6, 35, 11, 18 or 2 as the dopant may lead to devices having particularly good properties. Specifically, devices having an emissive layer using Compound 6 as the dopant, an emissive layer with Compound 35 as a dopant, an emissive layer with Compound 35 as a dopant and Compound H as the host, an emissive layer with Compound 35 as a dopant and Compound G as a host, an emissive layer with Compound 11 as the dopant and Compound H as the host, an emissive layer with Compound 11 as a dopant and Compound G as the host, an emissive layer with Compound 18 as a dopant, and/or an emissive layer with Compound 2 as a dopant. Such devices often have one or more improvements in device stability, luminescence linewidth or device efficiency as shown in Table 1.

Particular Ir(6-alkylppy) type compounds are provided which may lead to devices having particularly narrow luminescence linewidth. Specifically, devices using heteroleptic Compounds 35 or 11 as an emissive dopant as shown in Table 1. It is believed that a substitution at the 6-position has this effect because it exerts a steric effect on the Ir complex, resulting in a relatively longer N—Ir bond, which translates to a narrower emission. Thus having an Ir(ppy) compounds have a 6-alkyl group and with a heteroleptic nature is particularly useful in achieving narrow luminescence linewidth and improved device stability without much increase in evaporation temperature as compared to the homoleptic counterpart.

A process for making $Ir(L_a)(L_b)(L_c)$ complex is provided, the process comprising reacting an intermediate having the formula $(L_a)(L_b)IrX$ with $L_c$ to produce a $Ir(L_a)(L_b)(L_c)$ complex, where $L_a$, $L_b$ and $L_c$ are independently bidentate cyclometallated ligands having the formula:

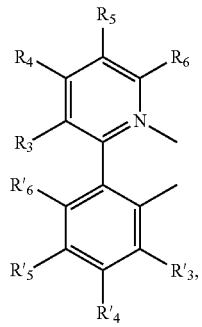

where $R_3$, $R_4$, $R_5$, $R_6$, $R'_3$, $R'_4$, $R'_5$, and $R'_6$ are independently selected from the group consisting of hydrogen, alkyl, alkenyl, alkynyl, alkylaryl, CN, $CO_2R$, $C(O)R$, $NR_2$, $NO_2$, OR, halo, aryl, heteroaryl, substituted aryl, substituted heteroaryl, or a heterocyclic group;

where at least one of $R_6$ or $R'_3$ is not hydrogen, and $R_6$ or $R'_3$ is selected from the group consisting of alkyl, alkenyl, alkynyl, alkylaryl, CN, $CO_2R$, $C(O)R$, $NR_2$, $NO_2$, OR, halo, aryl, heteroaryl, substituted aryl, substituted heteroaryl, and a heterocyclic group; and X is

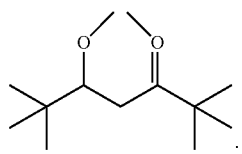

Examples of the process to make complexes having the formula $Ir(L_a)(L_b)(L_c)$ include complexes wherein $(L_a)$, $(L_b)$, and $(L_c)$ are photoactive.

Examples of the process to make complexes having the formula $Ir(L_a)(L_b)(L_c)$ include $L_a$, $L_b$ and $L_c$ wherein $R'_6$ is hydrogen, and $R_3$ is selected from the group consisting of alkyl, alkenyl, alkynyl, alkylaryl, CN, $CO_2R$, $C(O)R$, $NR_2$, $NO_2$, OR, halo, aryl, heteroaryl, substituted aryl, substituted heteroaryl, and a heterocyclic group. The yield is at least 30% or at least 50%.

Examples of the process to make complexes having the formula $Ir(L_a)(L_b)(L_c)$ include $L_a$, $L_b$ and $L_c$ wherein $R_3$ is hydrogen, and $R'_6$ is selected from the group consisting of alkyl, alkenyl, alkynyl, alkylaryl, CN, $CO_2R$, $C(O)R$, $NR_2$, $NO_2$, OR, halo, aryl, heteroaryl, substituted aryl, substituted heteroaryl, and a heterocyclic group. The yield is at least 10%.

Examples of the process to make complexes having the formula $Ir(L)(L_b)(L_c)$ include $L_a$, $L_b$ and $L_c$ are the same.

Examples of the process to make complexes having the formula $Ir(L_a)(L_b)(L_c)$ include $L_a$, $L_b$ and $L_c$ wherein $R_6$ is methyl, and $R_3$, $R_4$, $R_5$, $R'_3$, $R'_4$, $R'_5$ and $R'_6$ are hydrogen.

Examples of the process to make complexes having the formula $Ir(L_a)(L_b)(L_c)$ include $L_a$, $L_b$ and $L_c$ wherein $R'_3$ is methyl, $R'_5$ is methyl, $R_4$ is methyl and $R_3$, $R_5$, $R_6$, $R'_4$, and $R'_6$ are hydrogen.

Examples of the process to make complexes having the formula $Ir(LX)(L_b)(L_c)$ include $L_a$, $L_b$ and $L_c$ wherein $R'_3$ is methyl, $R'_5$ is methyl, and $R_3$, $R_4$, $R_5$, $R_6$, $R'_4$, and $R'_6$ are hydrogen.

Figure 4:
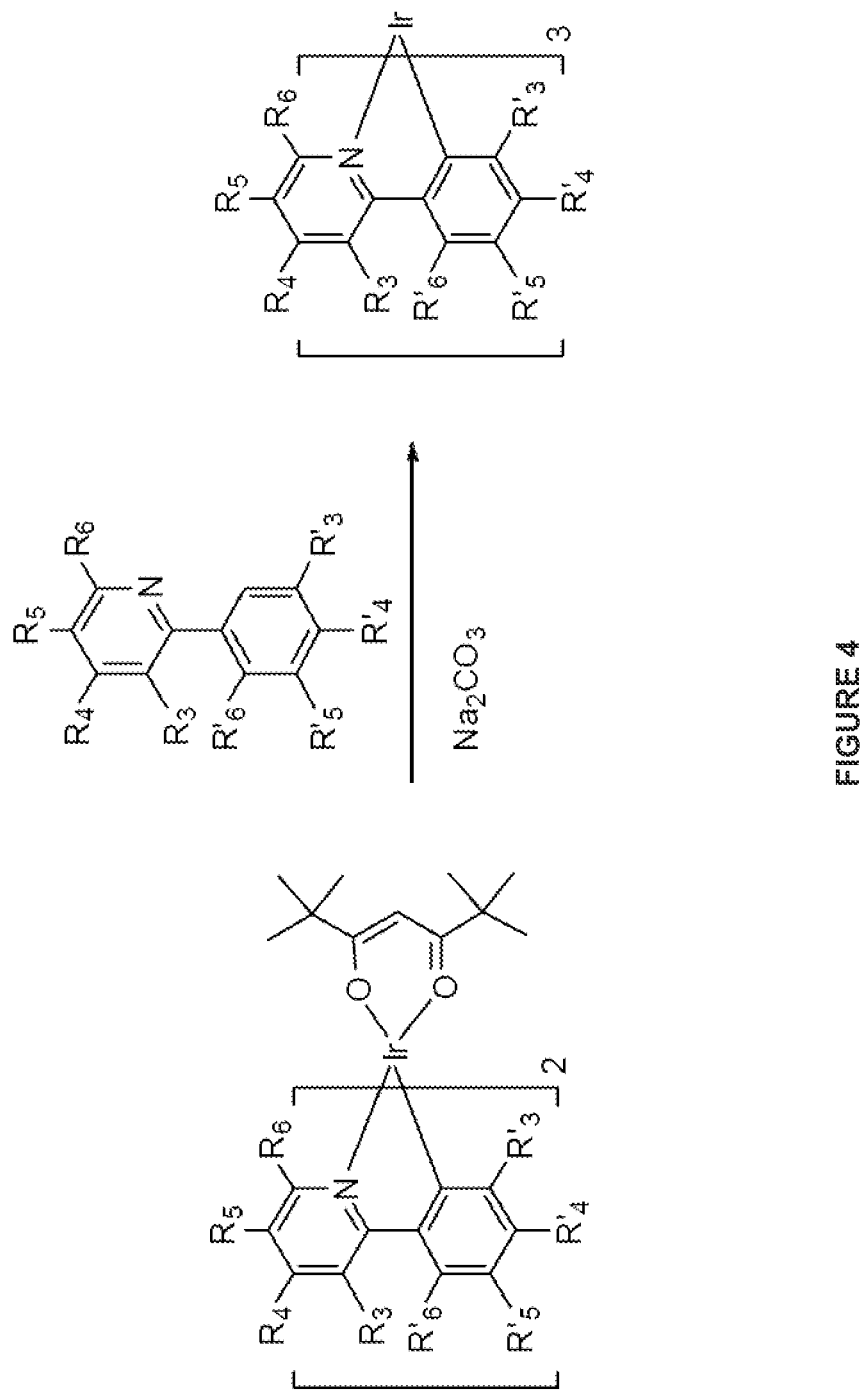
FIG. 4 shows a reaction in a synthetic pathway.

As discussed in previous paragraphs, the yield of iridium complexes having sterically-demanding ligands may be improved by a process wherein an intermediate $Ir(L_2)^t Buacac$ is reacted with L to produce $IrL_3$. For example, the $Ir(L_2)^t Buacac$ intermediate method results in improved yield of Compound 17, Compound 32, and Intermediate I in the synthesis of Compound 11. The reaction from the $Ir(L_2)^t Buacac$ to $IrL_3$ complex is shown in FIG. 4. Similarly, improved yield of a complex having the formula $Ir(L_a)(L_b)(L_c)$ may be improved by reacting an intermediate $Ir(L_a)(L_b)^t Buacac$ with $L_c$.

EXPERIMENTAL

Some of the homoleptic and heteroleptic alkyl and/or aryl substituted iridium compounds were synthesized as follows:

Compound 1

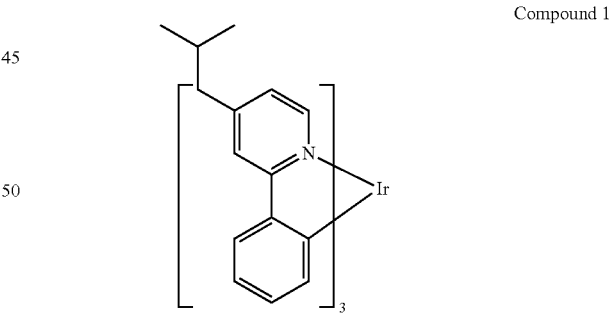

Compound 1

Step 1.10 g (67.5 mmol) of 2,4-dichloropyridine, 9 g (74 mmol) of phenylboronic acid, 28 g (202 mmol) of potassium carbonate, 250 mL of dimethoxyethane, and 150 mL of water were mixed in a 3-neck flask. The system was purged with nitrogen for 30 minutes. 2.3 g (2.0 mmol) of $Pd(PPh_3)_4$ was added and the mixture was heated to reflux for 20 hours. After cooled to room temperature, the reaction mixture was extracted with ethyl acetate and dried over magnesium sulfate. The product was column chromatographed with 5% ethyl acetate and hexanes. 9.2 (72% yield) of product was obtained after column.

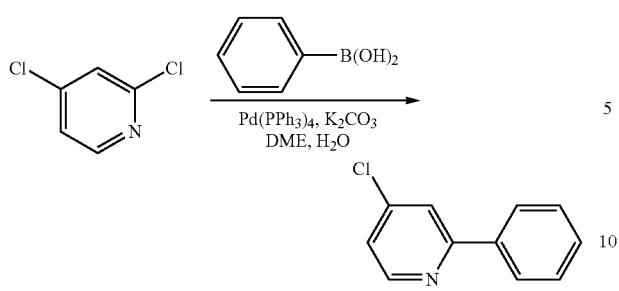

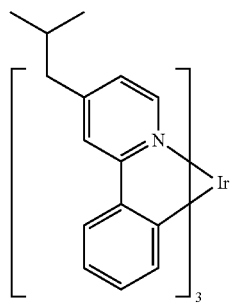

Compound 2

Step 2. 8.8 g (46 mmol) of 4-chloro-2-phenylpyridine, 7 g (69 mmol) of isobutylboronic acid, 298 g (138 mmol) of potassium phosphate, 1.5 g (3.68 mmol) of 2-dicyclohexylphosphino-2',6'-dimethoxybiphenyl, 100 mL of toluene were mixed in a 3-neck flask. The system was purged with nitrogen for 30 minutes. 0.84 g (0.92 mmol) of $Pd_2(dba)_3$ was added and the mixture was heated to reflux for 4 hours. After cooled to room temperature, the reaction mixture was filtered through a Celite bed. The product was column chromatographed with 5% ethyl acetate and hexanes. 8.3 g of product was obtained after column (85% yield).

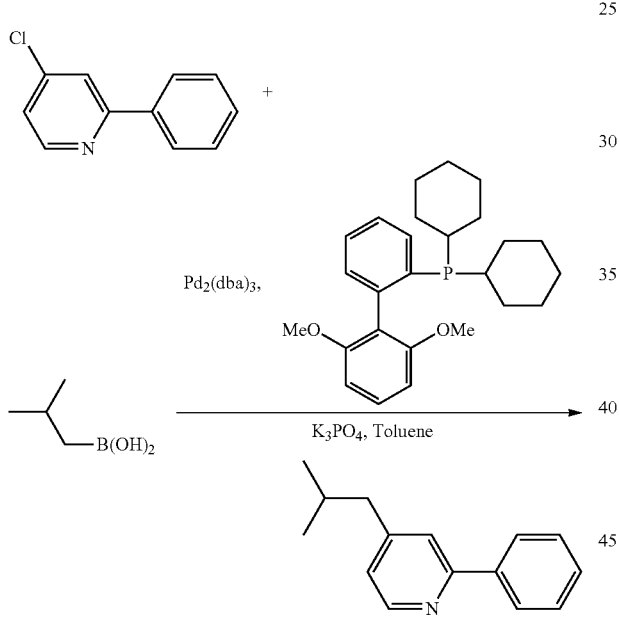

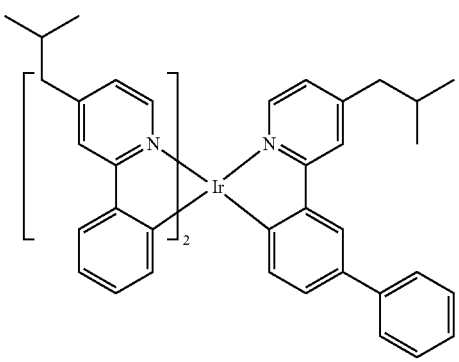

Compound 2

Step 3. 7.3 g (34.5 mmol) of 4-isobutyl-2-phenylpyridine and 3.4 g (6.9 mmol) of $Ir(acac)_3$ were heated to reflux in 50 mL of ethylene glycol for 24 hours. After cooled to room temperature, 100 mL of methanol was added. The precipitate was collected by filtration. The solid was purified by column using 1:1 dichloromethane and hexanes as eluent. 3.1 g product was obtained after column purification. (55% yield). The product was further purified by high vacuum sublimation at 240° C.

Step 1. 2.1 g (2.6 mmol) of tris[4-isobutyl-2-phenylpyridine]iridium(III) was dissolved in 100 mL of dichloromethane. To the solution was added 0.45 g (2.6 mmol) of N-bromosuccimide in dichloromethane drop wise. After overnight stirring at room temperature, the reaction was concentrated to 50 mL of solvent and precipitated from methanol. The solid was dried under vacuum and used for the next step without further purification. 2.1 g product was collected, which contains ~71% of mono brominated compound.

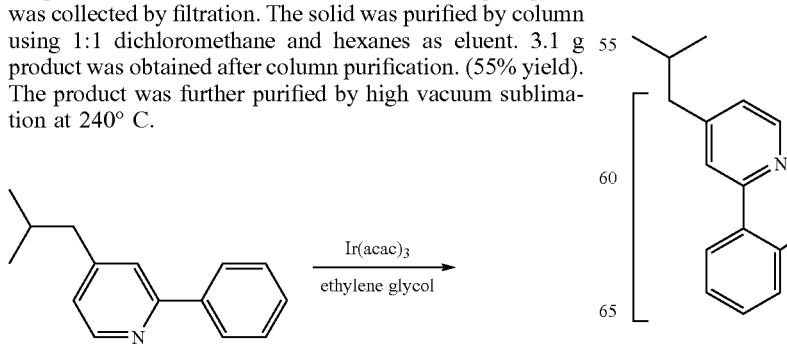

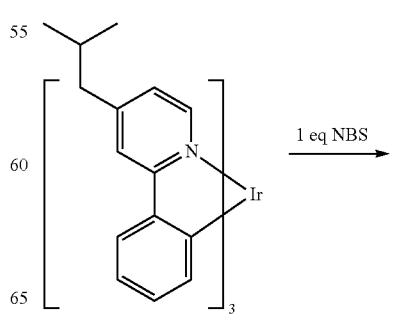

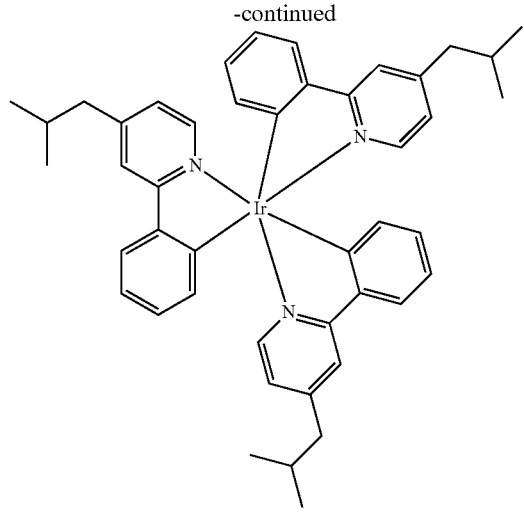

+

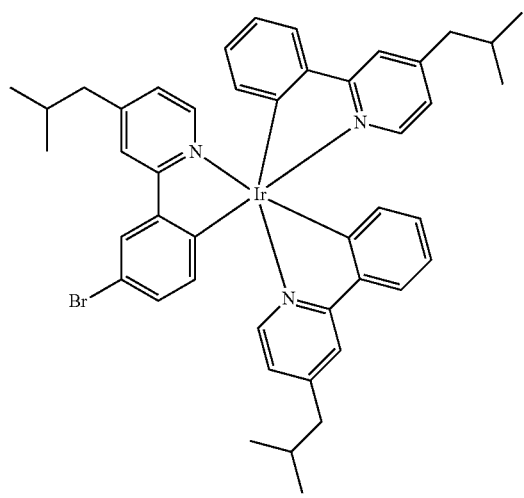

+

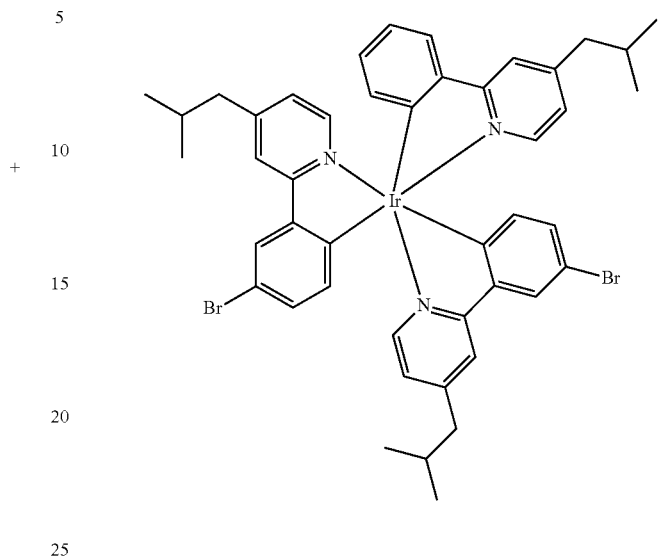

Step 2. 2.1 g of the brominated iridium complex mixture from Step 1, 1.2 g (4.6 mmol) of pinacolatodiboron, 0.68 g (6.9 mmol) of potassium acetate, 100 mL of dioxane were mixed in a 3-neck flask. The system was purged with nitrogen for 30 minutes. To the mixture was added 0.06 g (0.07 mmol) of Pd(dppf)$_2$Cl$_2$. The reaction was heated to 90° C. for 15 hours. The reaction was monitored by TLC. After the reaction was done, the solvent was evaporated. The residue was columned with 1:1 dichloromethane and hexanes. 1.1 g of product was obtained.

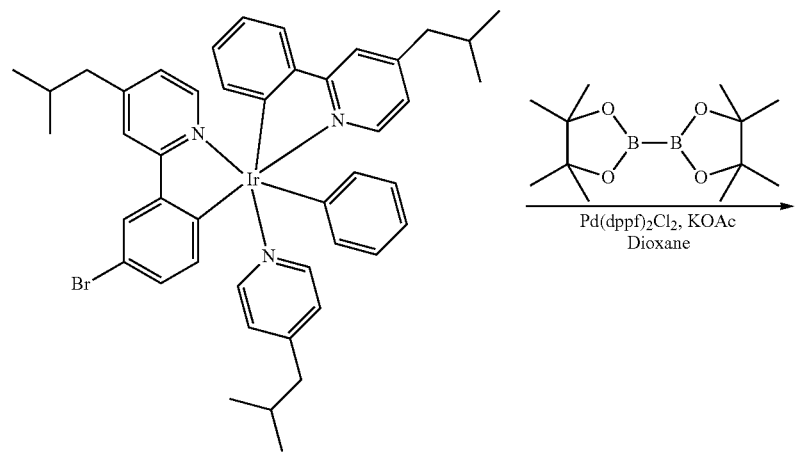

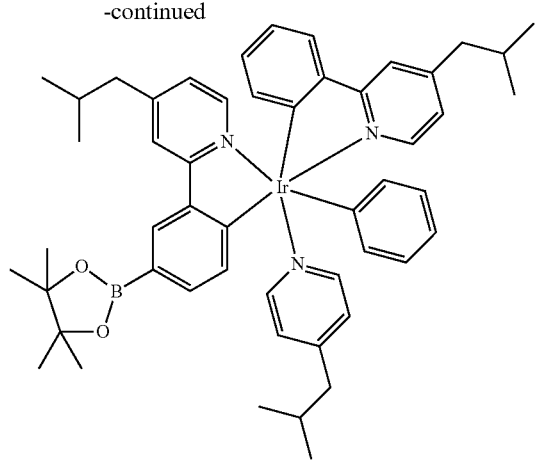

Step 3. 1.1 g (1.16 mmol) of boronic ester, 0.55 g (3.5 mmol) of bromobenzene, 0.8 g (3.48 mmol) of potassium phosphate, 0.02 g (0.046 mmol) of 2-dicyclohexylphosphino-2',6'-dimethoxybiphenyl, 60 mL of toluene and 6 mL of water were mixed in a 3-neck flask. The system was purged with nitrogen for 30 minutes. 0.01 g (0.01 mmol) of $Pd_2(dba)_3$ was added and the mixture was heated to reflux for 4 hours. After cooled to room temperature, the reaction mixture was filtered through a Celite bed. The product was columned with 1:1 dichloromethane and hexanes. 1.0 g of product was obtained after column. The product was further purified by high vacuum sublimation at 260° C.

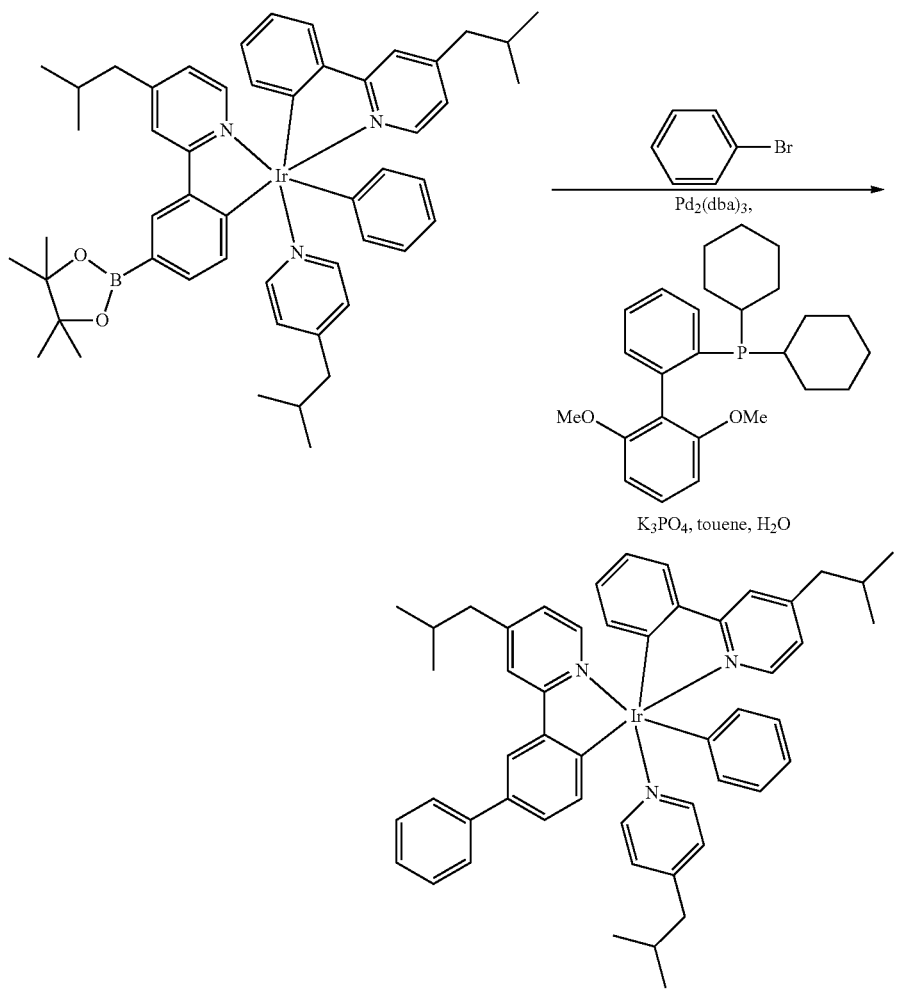

Compound 3

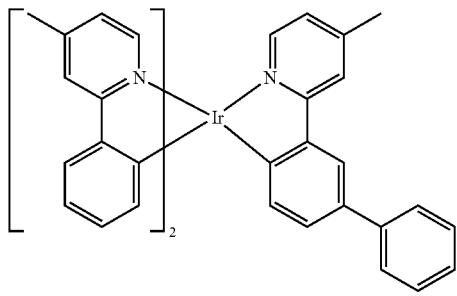

Step 1. Tris(4-methyl-2-phenylpyridine)iridium(III) (1.3 g, 1.9 mmol), N-bromosuccinimide (0.33 g, 1.9 mmol) were dissolved in 400 mL of dichloromethane. The mixture was purged with nitrogen for 10 minutes and stirred at room temperature in the dark for overnight. The solvent was evaporated under reduced pressure. The residue was washed by methanol. 1.4 g (95% yield) of yellow solid mixture was obtained.

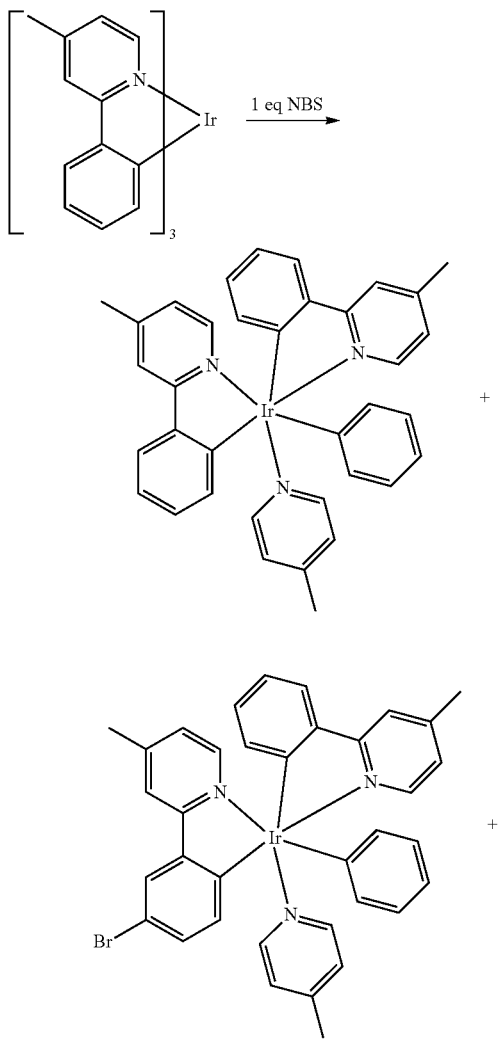

Compound 3

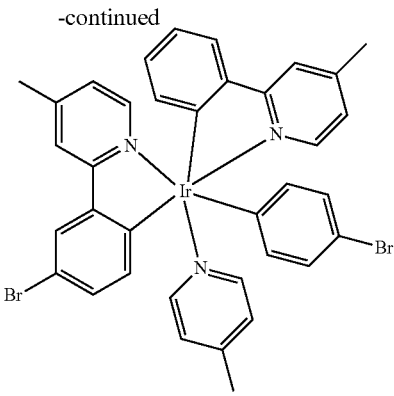

Step 2. The brominated Ir complex mixture from Step 1 (1.3 g, 1.7 mmol), pinacolatodiboron (0.85 g, 3.4 mmol), potassium acetate (0.5 g, 5.1 mmol), and anhydrous dioxane (100 mL) were mixed and purged with nitrogen for 15 minutes. Pd(dppf)$_2$Cl$_2$ (42 mg, 0.05 mmol) was then added in and the mixture was purged with nitrogen for another 10 minutes. After heated at 90° C. for overnight, the mixture was cooled to room temperature and evaporated under reduced pressure. The crude product was purified by silica column with up to 30% CH$_2$Cl$_2$ in hexanes to yield 0.9 g of a yellow solid (64% yield).

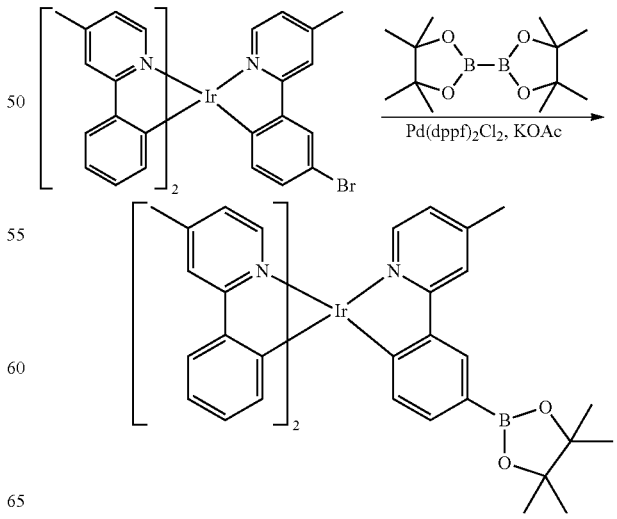

Step 3. The product from Step 2, bromobenzene (0.41 g, 2.6 mmol), 2-dicyclohexylphosphino-2',6'-dimethoxybiphenyl (14.4 mg, 0.035 mmol), potassium phosphate tribasic (557 mg, 2.6 mmol), toluene (60 mL) and water (20 mL) were mixed and purged with nitrogen for 15 minutes. The Pd$_2$(dba)$_3$ was then added and the mixture was purged with nitrogen for another 10 minutes. After being refluxed overnight, the organic layer was collected and dried with MgSO$_4$. The crude product was purified by silica column with 1:1 CH$_2$Cl$_2$ and hexanes to get 0.6 g of a yellow solid (89% yield). The product was further purified by high vacuum sublimation at 260° C.

Step 1. 2,4-dichloropyridine (10 g, 67.6 mmol), biphenyl-3-ylboronic acid (13.4 g, 67.6 mmol), palladium acetate (0.5 g, 2 mmol), triphenylphosphine (2.1 g, 8.1 mmol), potassium carbonate (28 g, 203 mmol), dimethoxyethane 120 mL and water 40 mL were mixed in a 300 mL 3-neck flask. The system was purged with nitrogen for 15 minutes and then refluxed overnight. After the reaction was cooled to room temperature, the organic layer was collected, dried over MgSO$_4$ and evaporated under reduced pressure. The crude product was purified by silica column eluted with up to 10% ethyl acetate in hexanes to give 12.2 g of a yellow oil (68% yield).

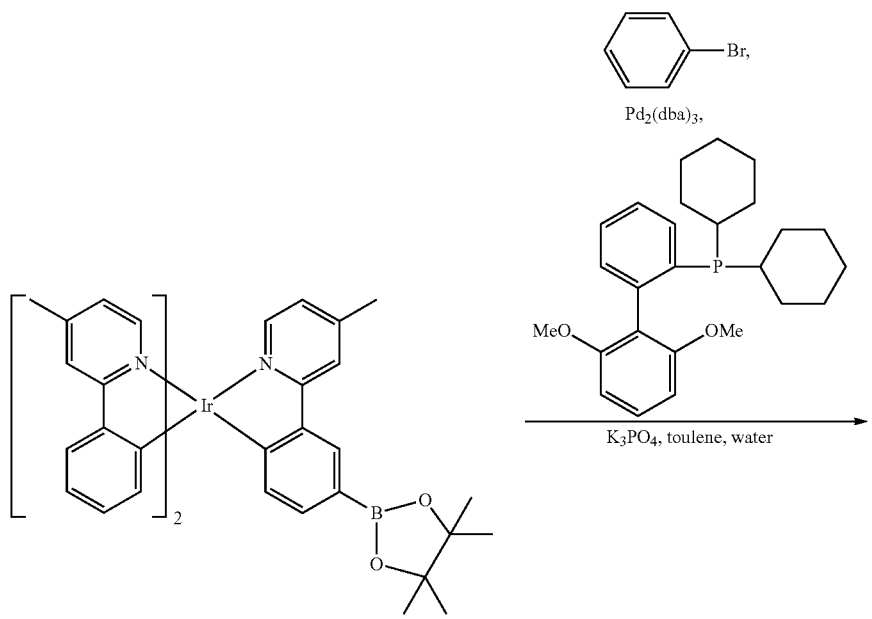

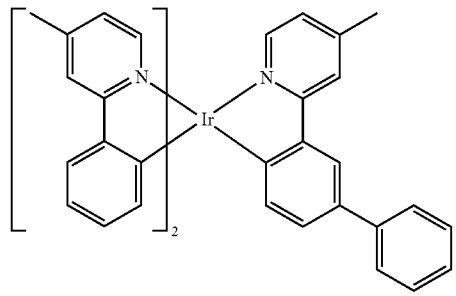

Compound 4

Compound 4

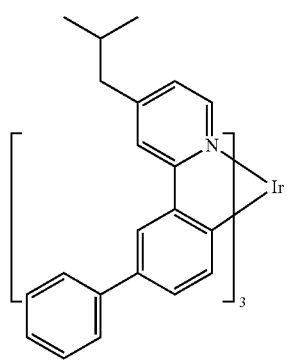

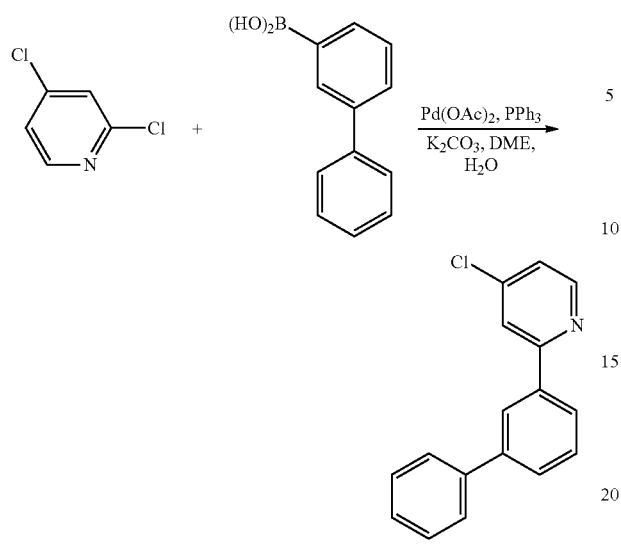

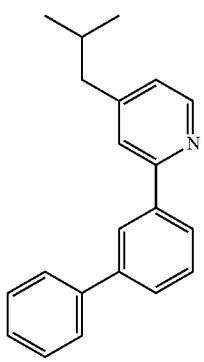

Step 2. 2-(biphenyl-3-yl)-4-chloropyridine (12.2 g, 45.9 mmol), i-butylboronic acid (5.6 g, 55.1 mmol), potassium phosphate tribasic (29 g, 138 mmol), toluene (300 mL) were mixed. The system was purged with nitrogen for 15 minutes. Then 2-dicyclohexylphosphino-2',6'-dimethoxybiphenyl (0.8 g, 1.8 mmol) and $Pd_2(dba)_3$ (0.4 g, 0.5 mmol) were added. The system was purged with nitrogen for another 5 minutes. After being refluxed overnight, the reaction was cooled to room temperature and washed with water. The combined organic layers were dried over $MgSO_4$ and evaporated under reduced pressure. The crude product was purified by silica column eluted with up to 5% ethyl acetate in hexanes to get 3.5 g of a yellow oil (27% yield) as the product.

Step 3. 2-(biphenyl-3-yl)-4-isobutylpyridine (1 g, 3.5 mmol), $Ir(acac)_3$ (0.4 g, 0.9 mmol) and ethylene glycol (10 mL) were mixed. The system was vacuumed and refilled with nitrogen 3 times. After heated at 220° C. (sand bath temperature) overnight, the reaction was cool to room temperature. The yellow precipitate was collected by filtration and washed by methanol. The crude product was purified by silica column eluted with 1:1 dichloromethane and hexanes to give 440 mg of a yellow solid (46% yield). The product was further purified by high vacuum sublimation at 280° C.

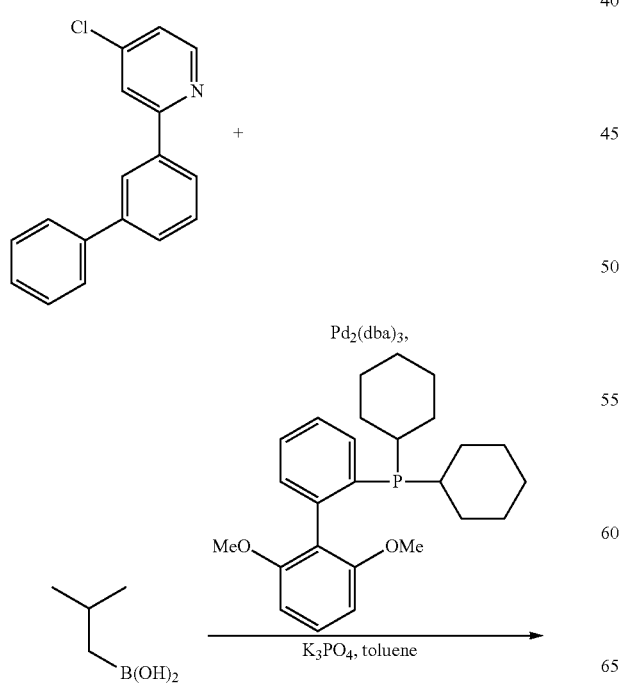

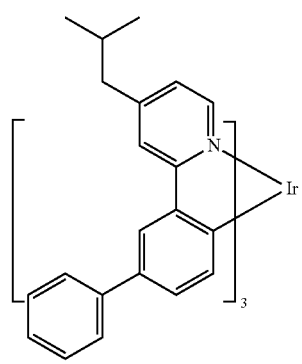

Compound 5

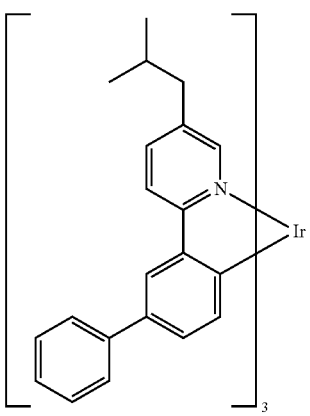

Step 1. 2-bromo-5-chloropyridine (12.0 g, 62.3 mmol), biphenyl-3-ylboronic acid (14.9 g, 75 mmol), palladium acetate (0.035 g, 2.5 mol %)), triphenylphosphine (0.8 g, 5 mol %) and potassium carbonate (26.0 g, 188 mmol) was placed in a 500 mL 3-neck flask. 150 mL of dimethoxyethane and 150 mL of H₂O was added to the flask. Nitrogen was purged through the solution for 30 minutes and then the solution was refluxed for 8 hours in an atmosphere of nitrogen. The reaction was then allowed to cool to room temperature and the organic phase was separated from the aqueous phase. The aqueous phase was washed with ethyl acetate and the organic fractions were combined and dried over magnesium sulfate and the solvent removed under vacuum. The product was chromatographed using silica gel with ethyl acetate and hexanes as the eluent. The solvent was removed to give 14.5 g of a white solid (88% yield).

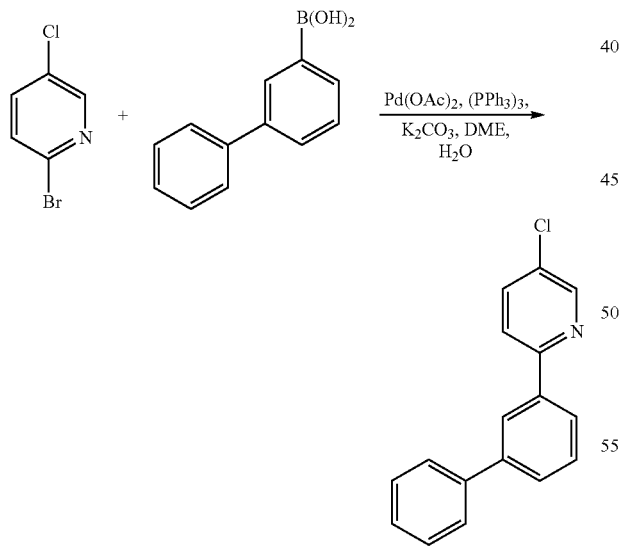

Step 2. 2-(biphenyl-3-yl)-5-chloropyridine (5.0 g, 19.0 mmol), isobutylboronic acid (4.0 g, 0.38 mmol), Pd₂(dba)₃ (0.20 g, 1 mol %), 2-dicyclohexylphosphino-2',6'-dimethoxybiphenyl (0.31 g, 4 mol %), potassium phosphate monohydrate (13 g, 57 mmol) was mixed in 100 mL of toluene in a 250 mL round bottom flask. Nitrogen was purged through the mixture for 20 minutes and the mixture was refluxed in a nitrogen atmosphere overnight. The reaction mixture was allowed to cool and the solvent removed under vacuum. The crude product was chromatographed using a silica gel column with 2% ethyl acetate in hexanes as the eluent. The solvent was then removed under vacuum to give 4 g of product.

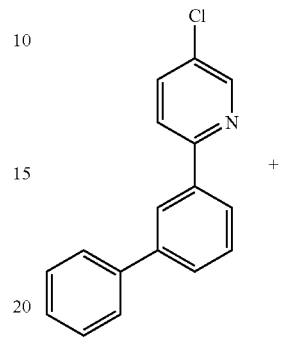

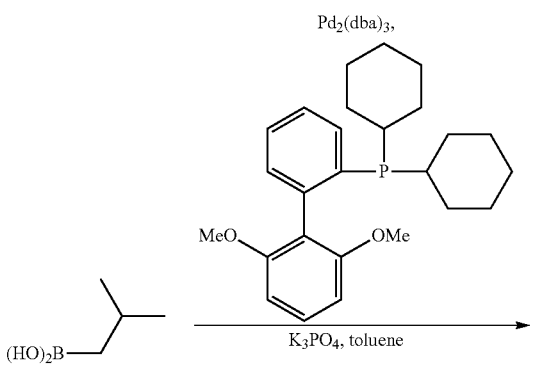

Step 3. 2-(biphenyl-3-yl)-5-isobutylpyridine (4.0 g, 14.0 mmol) and Ir(acac)₃ (1.7 g, 3.5 mmol) and 10 mL of ethylene glycol was placed in a 100 mL round bottom flask. The reaction mixture was refluxed at 220° C. overnight in an atmosphere of nitrogen. The reaction mixture was allowed to cool and 10 mL of methanol was added to the mixture. The precipitate was filtered and washed with methanol. The product was chromatographed using a silica gel column with dichloromethane and hexanes (50:50) as the eluent. 1.3 g of product was obtained (36% yield).

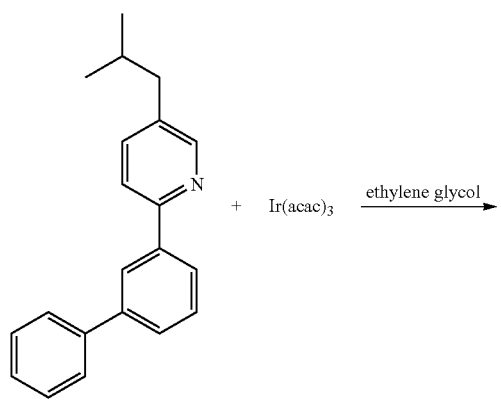

Compound 6

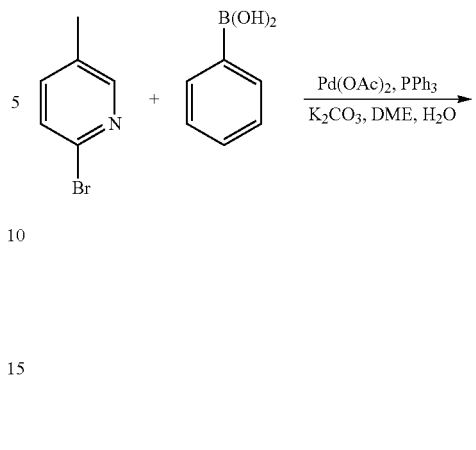

Step 2. 2-phenyl-5-methylpyridine (10.0 g, 59.0 mmol) and Ir(acac)₃ (10.0 g, 20.4 mmol) and 20 mL of ethylene glycol was placed in a 100 mL round bottom flask. The reaction mixture was refluxed at 220° C. overnight in an atmosphere of nitrogen. The reaction mixture was allowed to cool and 10 mL of methanol was added to the mixture. The precipitate was filtered and washed with methanol. The product was column chromatographed using a silica gel column with dichloromethane and hexanes (50:50) as the eluent. 5.94 g of product was obtained (42% yield).

Compound 6

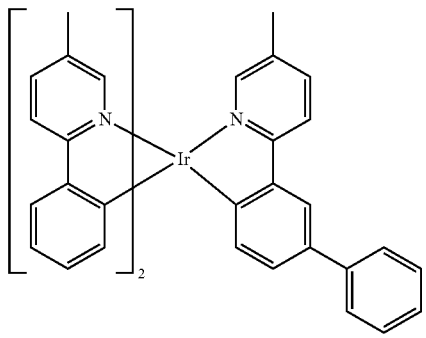

Step 1. A mixture of 2-bromo-5-methylpyridine (100 g, 581 mmol), phenylboronic acid (85.2 g, 700 mmol), palladium acetate (0.4 g, 2.5 mol %), triphenylphosphine (7.6 g, 5 mol %) and potassium carbonate (240.0 g, 1740 mmol) in 600 mL of dimethoxyethane and 600 mL of water was purged with nitrogen for 30 minutes and heated to reflux for 8 hours under nitrogen. The reaction was then allowed to cool to room temperature and the organic phase was separated from the aqueous phase. The aqueous phase was washed with ethyl acetate and the organic fractions were combined and dried over magnesium sulfate and the solvent removed under vacuum. The product was column chromatographed using silica gel with ethyl acetate and hexanes as the eluent. The solvent was removed to give 90.0 g of a clear liquid (92% yield).

Step 3. Tris(2-phenyl-4-methylpyridine)iridium(III) (4.4 g, 5.4 mmol) was dissolved in 600 mL of dichloromethane. N-bromosuccimide (0.96 g, 5.4 mmol) in dichloromethane was added drop wise over a period of 15 minutes. The reaction mixture was stirred at room temperature for 2 hours. The reaction volume was reduced to 200 mL and 200 mL of ethanol was added to precipitate the product. The solid was filtered and air dried overnight and used for the next step without further purification. 4.8 g of product was collected which contained ~71% of the mono brominated compound.

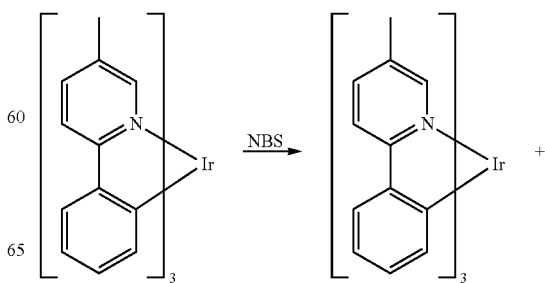

-continued

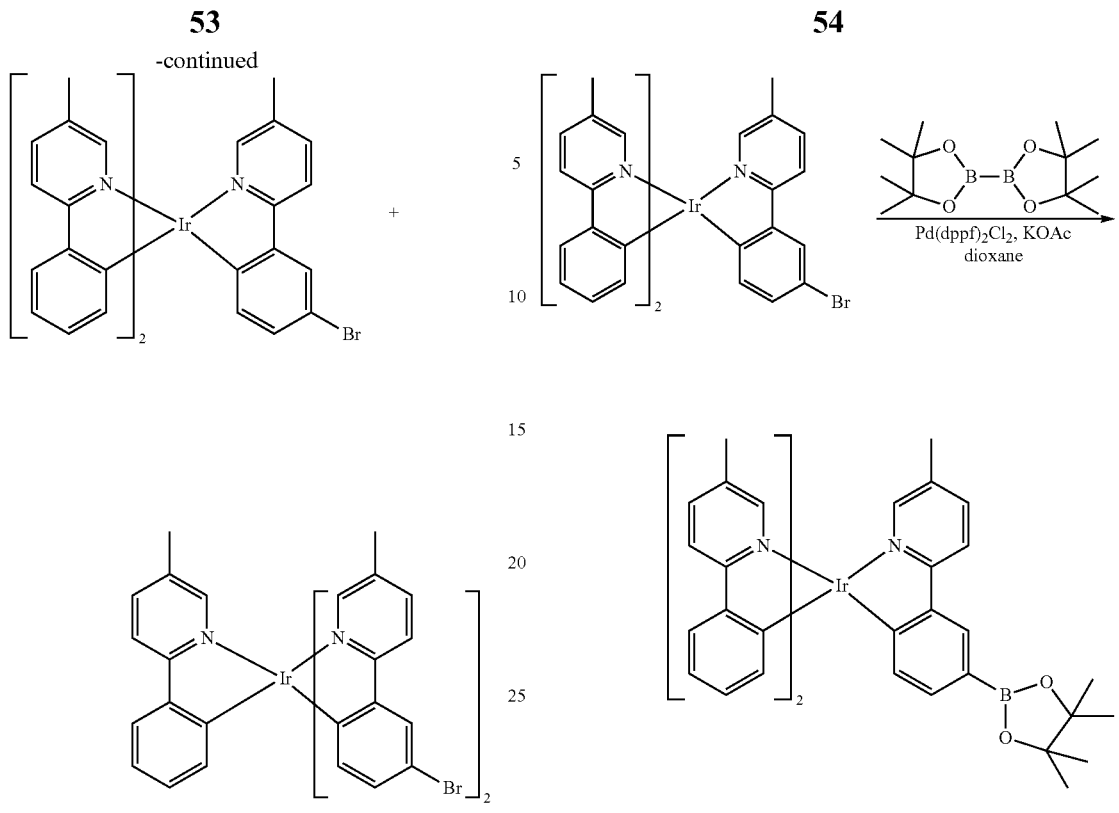

Step 4. The brominated mixture from Step 3 (5.0 g, 6.5 mmol), pinacolatodiboron (3.27 g, 12.9 mmol), potassium acetate (2.0 g. 20 mmol) and 200 ml of dioxane were mixed in a three-neck flask. The system was purged with nitrogen for 30 minutes. Pd(dppf)$_2$Cl$_2$ was then added (0.16 g, 3 mol %). The reaction was heated to 90° C. for 15 hours. After the reaction was complete, the solvent was evaporated. The residue was column chromatographed using a silica gel column with first 1:1 dichloromethane and hexanes as the eluent followed by 60:40 dichloromethane and hexanes. 1.9 g of product was obtained.

Step 5. The Ir borate ester (2.2 g, 2.7 mmol), bromobenzene (0.85 g, 5.4 mmol), potassium phosphate (1.86 g, 8.1 mmol), 2-dicyclohexylphosphino-2',6'-dimethoxybiphenyl (0.06 g, 5 mol %), 100 mL of toluene and 10 mL of water were mixed in a three-neck flask. The system was purged with nitrogen for 30 minutes. Pd$_2$(dba)$_3$ (0.02 g, 1 mol %) was added to the reaction mixture which was then refluxed for 2 hours. The reaction was cooled to room temperature and was filtered through a Celite plug. The residue was chromatographed using a silica gel column with 1:1 dichloromethane and hexanes as the eluent. 1.5 g of product was obtained.

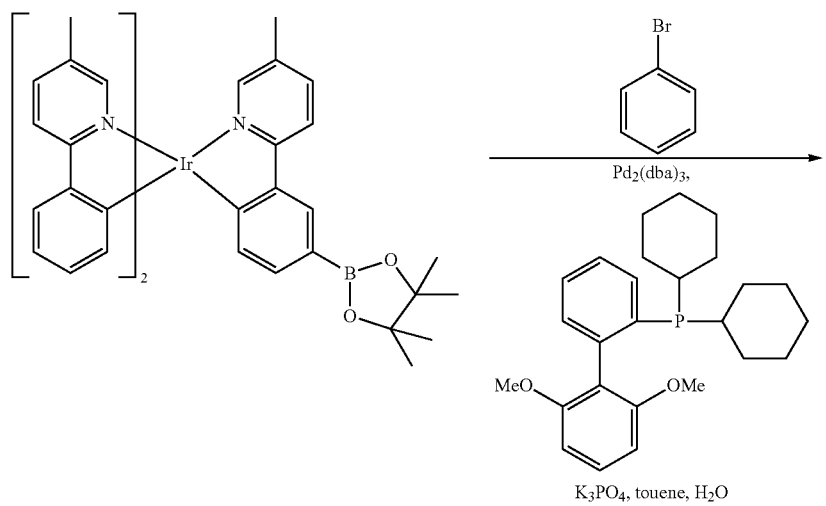

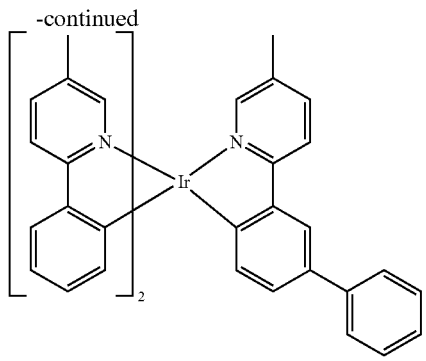

Compound 7

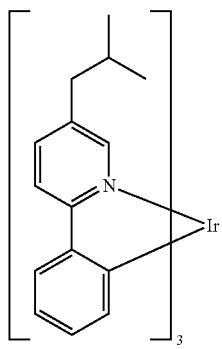

Compound 7

Step 1. A mixture of 2-bromo-5-chloropyridine (15.0 g, 77.94 mmol), phenylboronic acid (11.4 g, 93.53 mmol), triphenylphosphine (2.04 g, 7.79 mmol), and potassium carbonate (26.9 g, 194.9 mmol) in 150 mL of dimethoxyethane and 100 mL of water was purged with nitrogen for 20 minutes. Palladium acetate was added (0.87 g, 3.90 mmol) and the reaction mixture was heated to reflux overnight under nitrogen. The reaction mixture was cooled and filtered through Celite. The Celite was washed with water and ethyl acetate. The layers were separated and the aqueous layer extracted with ethyl acetate. The organic layers were dried over magnesium sulfate, filtered, and evaporated to a residue. The residue was purified by column chromatography eluting with 0 to 3% ethyl acetate/hexanes. 11.8 g (80% yield) of a white solid was obtained.

refluxed overnight under nitrogen. The cooled mixture was filtered through Celite and the Celite was washed with water and ethyl acetate. The layers were separated and the aqueous layer extracted with ethyl acetate. The organic layers were dried over magnesium sulfate, filtered, and evaporated to a residue. The residue was purified by column chromatography eluting with 0 and 2% ethyl acetate/hexanes. 11.05 g (84% yield) of a white solid was obtained.

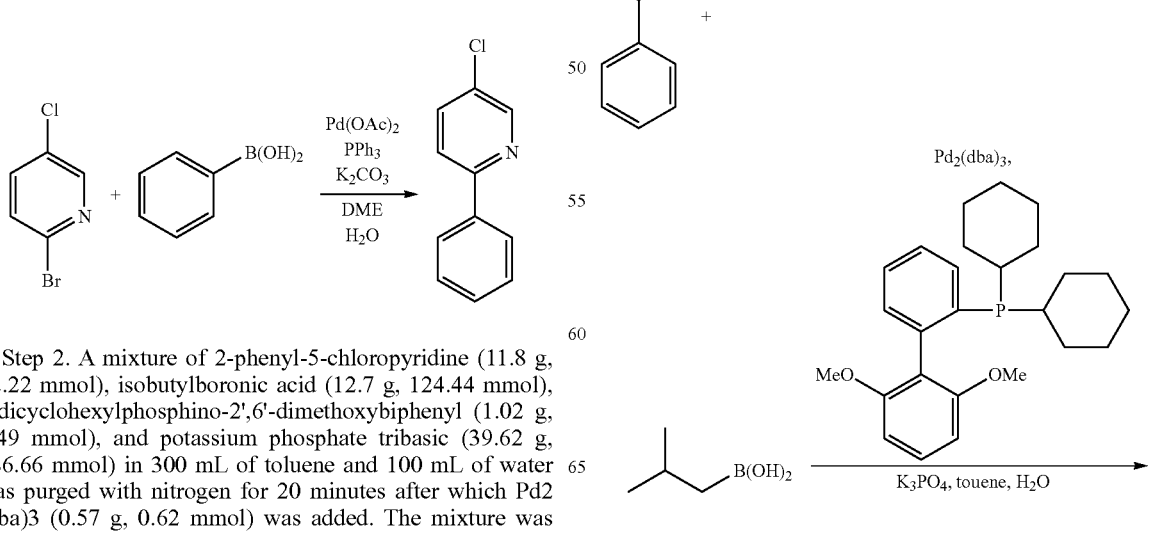

Step 2. A mixture of 2-phenyl-5-chloropyridine (11.8 g, 62.22 mmol), isobutylboronic acid (12.7 g, 124.44 mmol), 2-dicyclohexylphosphino-2',6'-dimethoxybiphenyl (1.02 g, 2.49 mmol), and potassium phosphate tribasic (39.62 g, 186.66 mmol) in 300 mL of toluene and 100 mL of water was purged with nitrogen for 20 minutes after which Pd2(dba)3 (0.57 g, 0.62 mmol) was added. The mixture was -continued

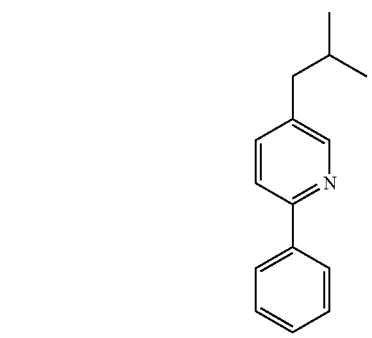

Step 3. A mixture 2-phenyl-5-isobutylpyridine (6.86 g, 32.47 mmol) and Ir(acac)$_3$ (3.16 g, 6.46 mmol) in 100 mL of ethylene glycol was heated to 210° C. overnight. The reaction was cooled and methanol was added and a yellow solid was filtered off. The solid was purified by column chromatography eluting with 20 and 40% dichloromethane/hexanes. 3.4 g (64% yield) of product was obtained.

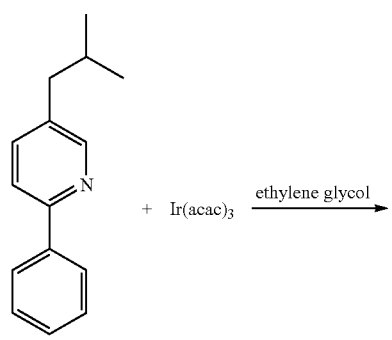

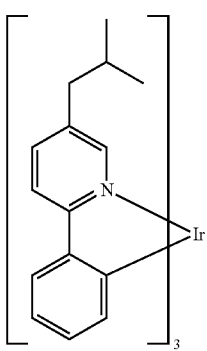

-continued

Compound 8

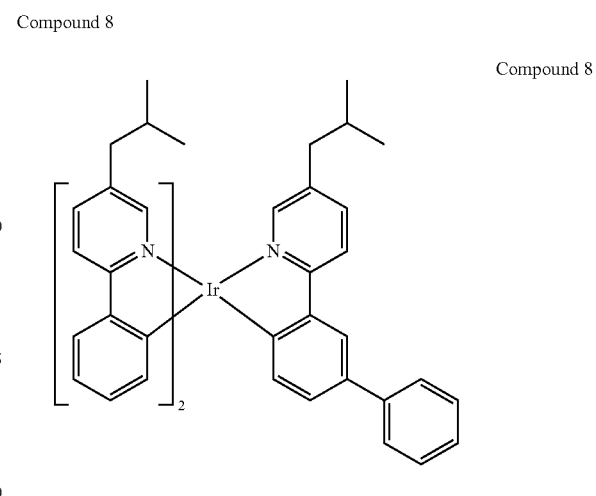

Compound 8

Step 1. A mixture of 2-bromo-5-chloropyridine (15.0 g, 77.94 mmol), phenylboronic acid (11.4 g, 93.53 mmol), triphenylphosphine (2.04 g, 7.79 mmol), and potassium carbonate (26.9 g, 194.9 mmol) in 150 mL of dimethoxyethane and 100 mL of water was purged with nitrogen for 20 minutes. Palladium acetate was added (0.87 g, 3.90 mmol) and the reaction mixture was heated to reflux overnight under nitrogen. The reaction mixture was cooled and filtered through Celite. The Celite was washed with water and ethyl acetate. The layers were separated and the aqueous layer was extracted with ethyl acetate. The organic layers were dried over magnesium sulfate, filtered, and evaporated to a residue. The residue was purified by column chromatography eluting with 0 to 3% ethyl acetate/hexanes. 11.8 g (80% yield) of a white solid was obtained.

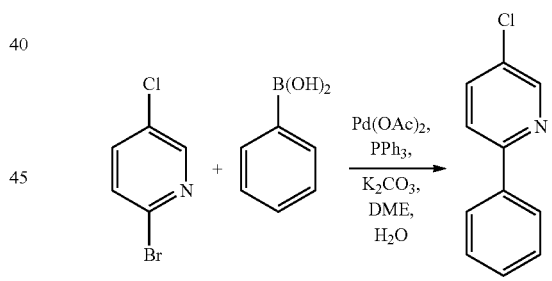

Step 2. A mixture of 2-phenyl-5-chloropyridine (11.8 g, 62.22 mmol), 2-methylpropylboronic acid (12.7 g, 124.44 mmol), 2-dicyclohexylphosphino-2',6'-dimethoxybiphenyl (1.02 g, 2.49 mmol), potassium phosphate tribasic (39.62 g, 186.66 mmol) in 300 mL of toluene and 100 mL of water was purged with nitrogen for 20 minutes after which Pd$_2$(dba)$_3$ (0.57 g, 0.62 mmol) was added. The mixture was refluxed overnight under nitrogen. The cooled mixture was filtered through a pad of Celite and the Celite was washed with water and ethyl acetate. The layers were separated and the aqueous layer was extracted with ethyl acetate. The organic layers were dried over magnesium sulfate, filtered, and evaporated to a residue. The residue was purified by column chromatography eluting with 0 and 2% ethyl acetate/hexanes. 11.05 g (84% yield) of a white solid was obtained.

reaction volume was reduced to 200 mL and 200 mL of ethanol was added to precipitate the product. The solid was filtered and air dried overnight and used for the next step without further purification. 4.9 g of product was collected, which contained ~71% of the mono brominated compound.

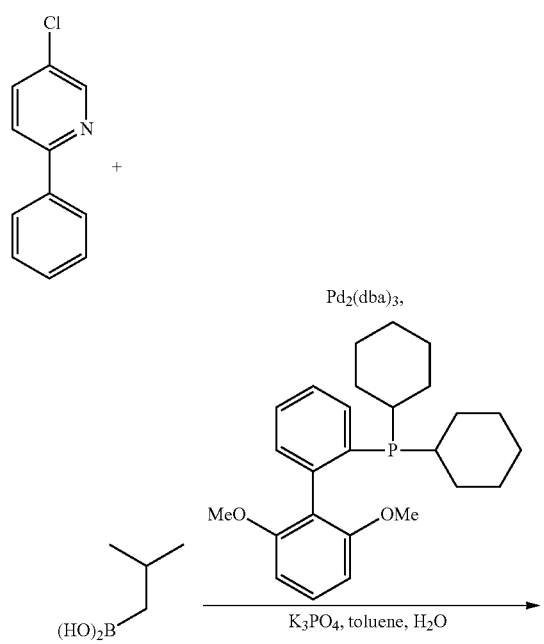

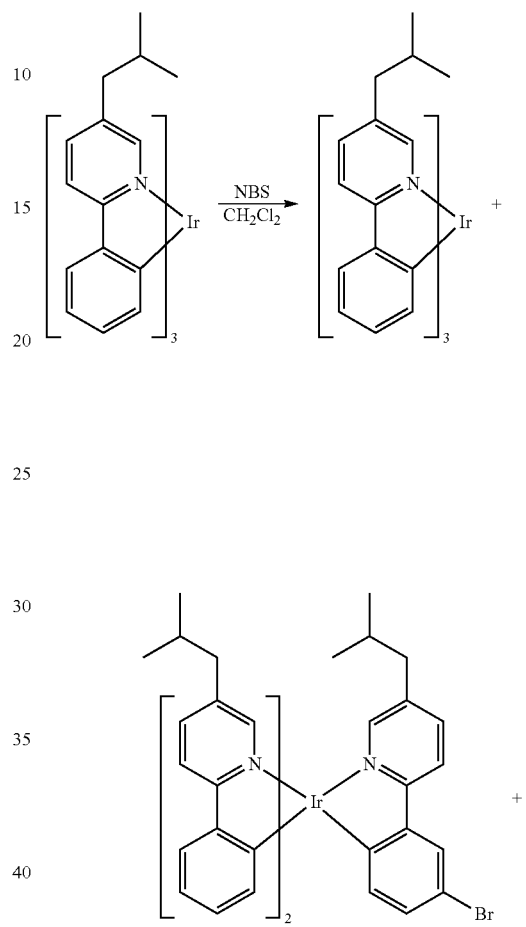

Step 3. A mixture of 2-phenyl-5-isobutylpyridine (6.86 g, 32.47 mmol) and Ir(acac)₃ (3.16 g, 6.46 mmol) in 100 mL of ethylene glycol was heated to 210° C. overnight. The reaction was cooled and methanol was added and a yellow solid was filtered off. The solid was purified by column chromatography eluting with 20 and 40% dichloromethane/ hexanes. to yield 3.4 g of product (64% yield).

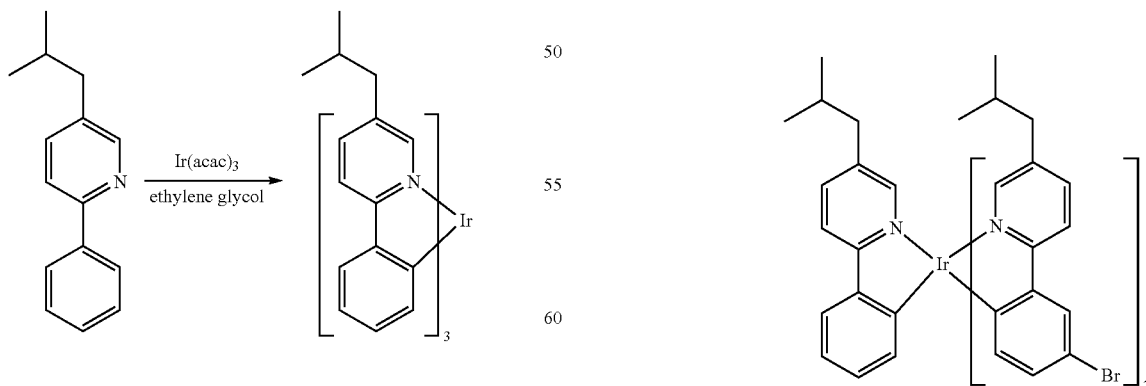

Step 4. Tris(2-phenyl-4-isobutylpyridine)iridium(III) (4.5 g, 6.5 mmol) was dissolved in 600 mL of dichloromethane. N-bromosuccimide (1.16 g, 6.5 mmol) in dichloromethane was added drop wise over a 15-minute period. The reaction mixture was stirred at room temperature for 2 hours. The Step 5. The brominated mixture (4.8 g, 5.3 mmol), pinacolatodiboron (2.71 g, 18.7 mmol), potassium acetate (1.6 g, 16.3 mmol) and 200 mL of dioxane were mixed in a three-neck flask. The system was purged with nitrogen for 30 minutes. Pd(dppf)$_2$Cl$_2$ was then added (0.43 g, 0.53 mmol). The reaction was heated to 90° C. for 15 hours. After the reaction was complete, the solvent was evaporated. The residue was chromatographed using a silica gel column with first 1:1 dichloromethane and hexanes as the eluent followed by 60:40 dichloromethane and hexanes to yield 1.0 g of the product.

-continued

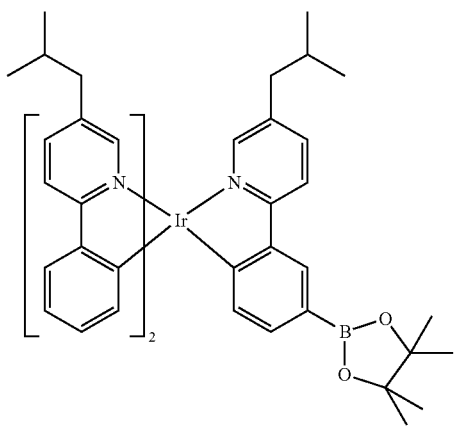

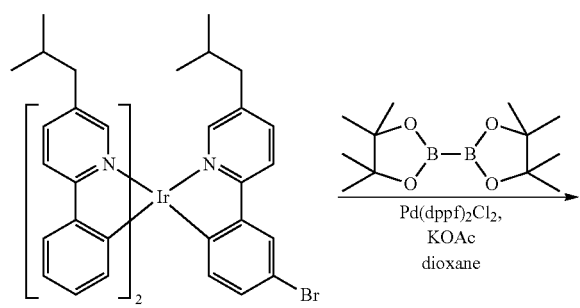

Step 6. The Ir borate ester (0.9 g, 0.9 mmol), bromobenzene (0.70 g, 4.7 mmol), potassium phosphate (1.96 g, 8.2 mmol), 2-dicyclohexylphosphino-2',6'-dimethoxybiphenyl (0.19 g, 5 mol %), 100 mL of toluene and 10 mL of water were mixed in a three-neck flask. The system was purged with nitrogen for 30 minutes. Pd$_2$(dba)$_3$ (0.01 g, 1 mol %) was added to the reaction mixture which was then refluxed for 2 hours. The reaction was cooled to room temperature and was filtered through a Celite plug. The residue was chromatographed using a silica gel column with 1:1 dichloromethane and hexanes as the eluent. 0.5 g of product was obtained.

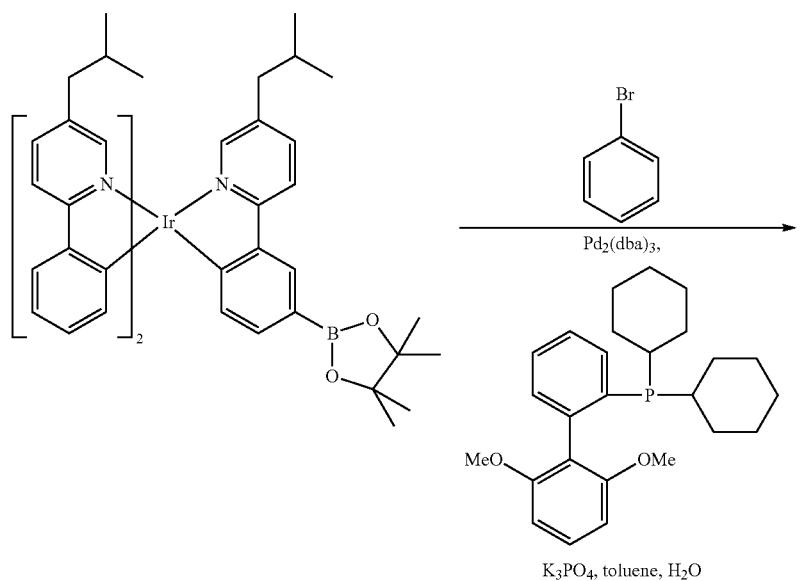

-continued

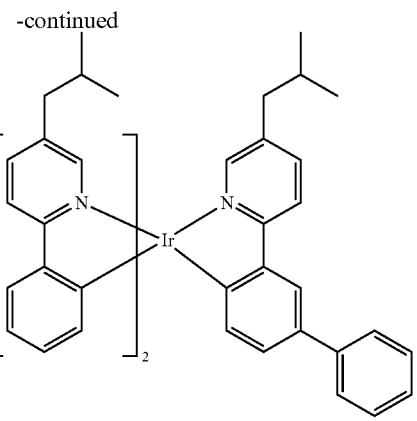

Compound 9

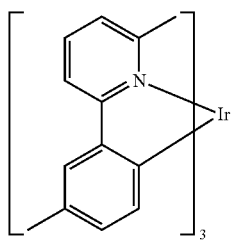

Compound 9

Step 1. 2-bromo-6-methylpyridine (10.0 g, 58.0 mmol), 3-methylphenylboronic acid (9.3 g, 70 mmol), palladium acetate (0.6 g, 5 mol %), triphenylphosphine (1.5 g, 10 mol %) and potassium carbonate (32.0 g, 232 mmol) was placed in a 500 mL 3-neck flask. 100 mL of dimethoxyethane and 100 mL of H$_2$O was added to the flask. Nitrogen was purged through the solution for 20 minutes and then the solution was refluxed for 8 hours in an atmosphere of nitrogen. The reaction was then allowed to cool to room temperature and the organic phase was separated from the aqueous phase. The aqueous phase was washed with ethyl acetate and the organic fractions were combined and dried over magnesium sulfate and the solvent removed under vacuum. The product was chromatographed using silica gel with ethyl acetate and hexanes as the eluent. The solvent was removed to give 8.08 g (76% yield) of a clear oil.

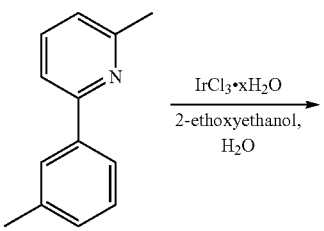

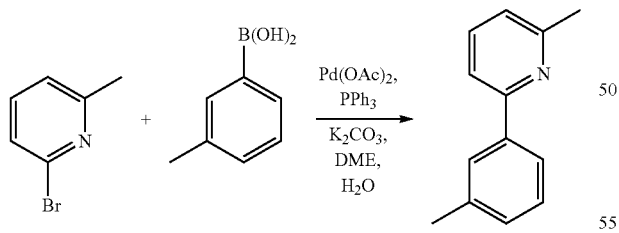

Step 2. 2-(5-methylphenyl)-6-methylpyridine (10.0 g, 54.6 mmol) and IrCl$_3$ (7.8 g, 21.8 mmol) was dissolved in 100 mL of a 3:1 mixture of 2-ethoxyethanol and water respectively in a 250 mL round bottom flask. Nitrogen was purged through the solution for 10 minutes and then refluxed under a nitrogen for 16 hours. The reaction mixture was the allowed to cool to room temperature and the precipitate was filtered and washed with methanol. The dimer was then dried under vacuum and used for next step without further purification. 8.6 g of the dimer was obtained after vacuum drying.

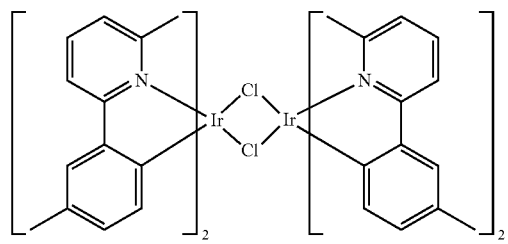

Step 3. The dimer (6.0 g, 5 mmol), 2,4-pentanedione (1.5 g, 15.0 mol) and potassium carbonate (7.0 g, 50.0 mmol) was added to 200 mL of 2-methoxyethanol and refluxed overnight. The solvent was removed on the rotary evaporator and the solid was redissolved in dichloromethane and chromatographed using a silica gel column and dichloromethane and hexanes as the eluent. The solvent was removed on the rotary evaporator and the product was washed with methanol and dried to give 5.1 g of product.

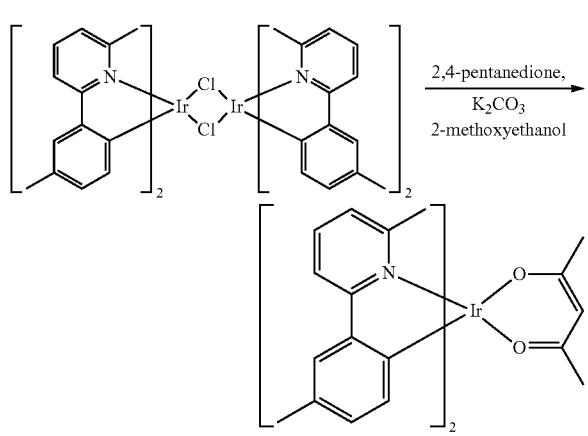

Step 4. The product from Step 3 (2.0 g, 3 mmol), 2-(3-methylphenyl)-6-methylpyridine (3.4 g, 6 mol eq) and potassium carbonate (2.5 g, 18 mmol) was placed in a 100 mL round bottom flask. The reaction mixture was heated at 250° C. for 8 hours. The reaction mixture was allowed to cool and 10 mL of methanol was added to the mixture. The precipitate was filtered and washed with methanol. The product was chromatographed using a silica gel column with dichloromethane and hexanes (50:50) as the eluent. 1.1 g of product was obtained (50% yield).

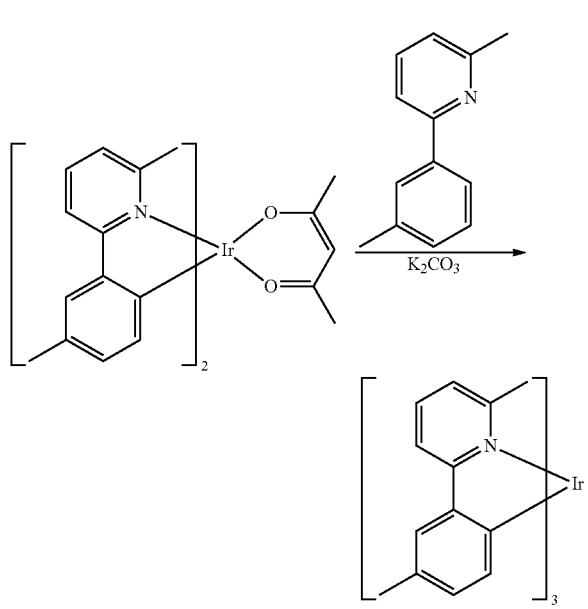

Compound 10

Step 1. A mixture of 2-chloro-6-methylpyridine (4.1 g, 32.4 mmol), biphenyl-3-ylboronic acid (7.7 g, 38.9 mmol), triphenylphosphine (0.85 g, 3.24 mmol), and potassium carbonate (11.2 g, 81.0 mmol) in 60 mL of dimethoxyethane and 40 mL of water was prepared. Nitrogen was purged into the mixture for 20 minutes. Palladium acetate was added (0.36 g, 1.62 mmol) and the reaction mixture was heated to reflux overnight under nitrogen. The reaction was cooled and diluted with water and ethyl acetate. The layers were separated and the aqueous layer was extracted with ethyl acetate. The organic layers were dried over magnesium sulfate, filtered and evaporated to a residue. The residue was purified by column chromatography eluting with 0, 1, and 2% ethyl acetate/hexanes. 6.9 g (87% yield) of a clear liquid was obtained.

A mixture of the Ir dimer (2.0 g, 1.87 mmol) in 200 mL of dichloromethane and 10 mL of methanol was prepared. Silver trifluoromethanesulfonate (1.0 g. 3.92 mmol) was added and the reaction mixture was stirred for 3 hours. A green solid was filtered off and washed with a small amount of dichloromethane. The filtrate was evaporated to dryness and dried under high vacuum. The material was transferred to a 100 mL flask and the product from Step 1 was added (1.8 g, 7.48 mmol) followed by 15 mL of tridecane. The mixture was heated at 190° C. overnight. Four compounds were formed. A green solid was filtered off and purified by column chromatography eluting with 10, 20, 40, and 50% dichloromethane/hexanes. 0.80 g of crude Compound 34 was obtained which was further purified by column chromatography, recrystallization from toluene and sublimation to 0.26 g of product.

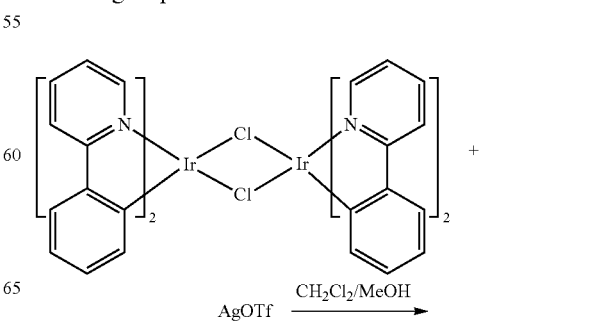

-continued

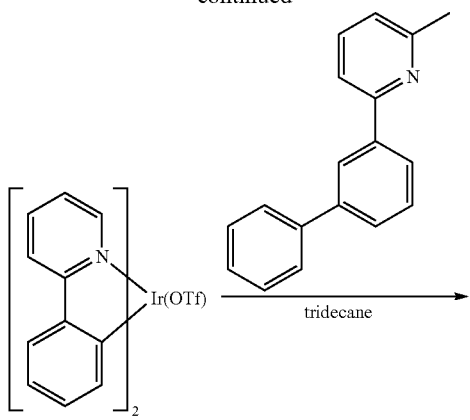

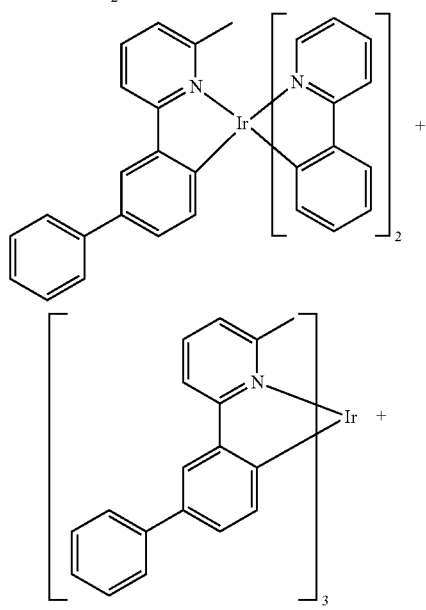

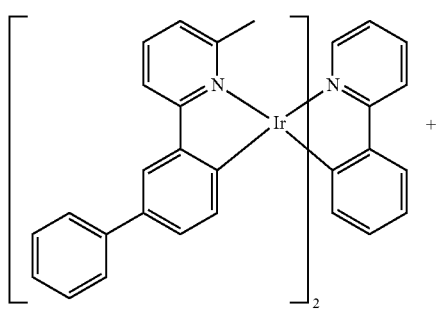

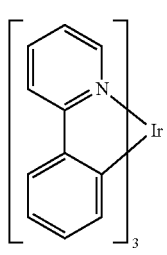

-continued

Compound 11

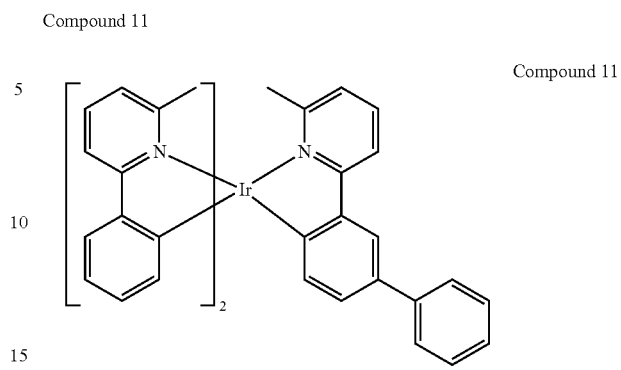

Compound 11

Step 1. A mixture of 2-bromo-6-methylpyridine (100.0 g, 580 mmol), phenylboronic acid (80.0 g, 640 mmol), palladium acetate (3.3 g, 2.5 mol %)), triphenylphosphine (8.0 g, 5 mol %) and potassium carbonate (240 g, 1740 mmol) in 600 mL of dimethoxyethane and 600 mL of water was purged with nitrogen for 30 minutes and then the solution was refluxed for 8 hours under nitrogen. The reaction was then allowed to cool to room temperature and the organic phase was separated from the aqueous phase. The aqueous phase was washed with ethyl acetate and the organic fractions were combined and dried over magnesium sulfate and the solvent removed under vacuum. The product was column chromatographed using silica gel with ethyl acetate and hexanes as the eluent. The solvent was removed to give 90.5 g of a clear liquid (92% yield).

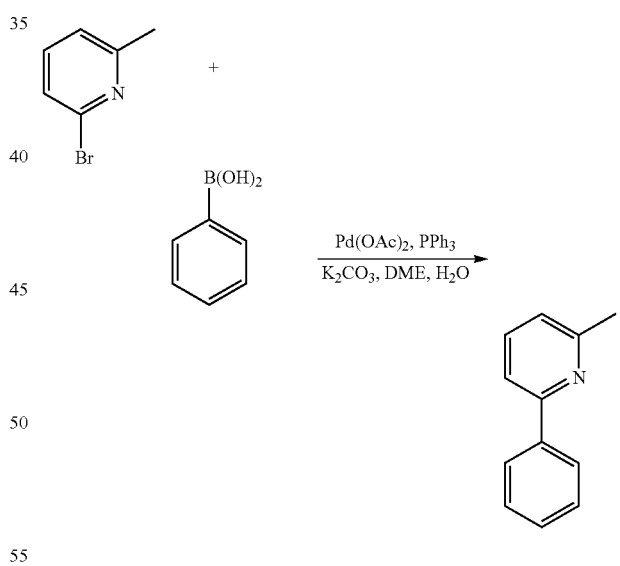

Step 2. 2-phenyl-6-methylpyridine (24.0 g, 142 mmol) and iridium(III) chloride (20.0 g, 56.8 mmol) was dissolved in 250 mL of a 3:1 mixture of 2-ethoxyethanol and water in a 500 mL round bottom flask. The mixture was purged with nitrogen for 10 minutes and then refluxed under nitrogen for 16 hours. The reaction mixture was the allowed to cool to room temperature and the precipitate was filtered and washed with methanol. The dimer was then dried under vacuum and used for next step without further purification. 16.0 g of the dimer was obtained after vacuum drying (50% yield).

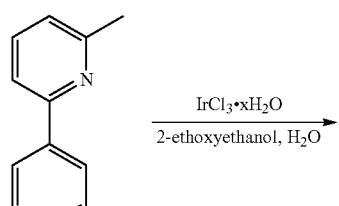

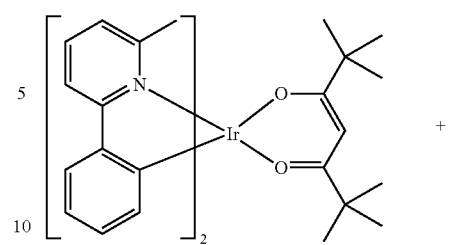

Step 3. The dimer (15.0 g, 13.3 mmol), dipivaloylmethane (25.0 g, 133 mmol), and potassium carbonate (18.0 g, 133 mmol) was added to 250 mL of 1,2-dichloroethane and refluxed for 24 hours. The reaction mixture was allowed to cool and the solvent was removed under vacuum. The residue was column chromatographed using silica gel pre-treated with triethylamine. Dichloromethane and hexanes (1:1) were used as the eluent. 17.8 g (94% yield) of product was obtained.

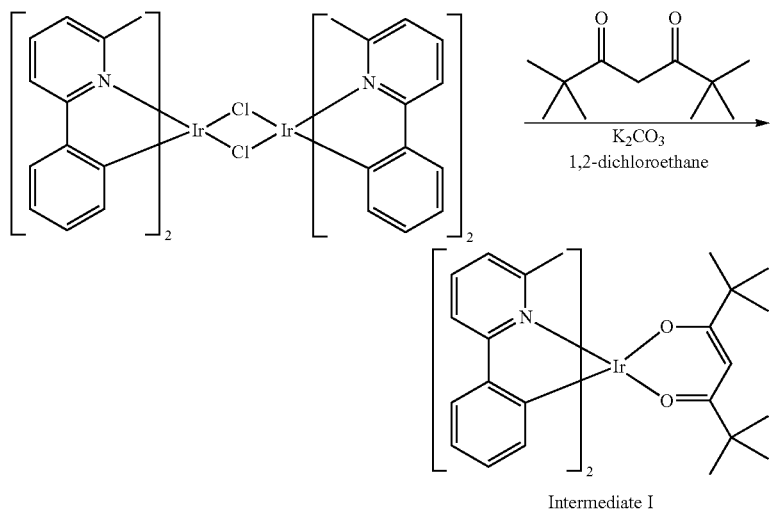

Intermediate I

Step 4. A mixture of the Ir complex (10.0 g, 14.0 mmol) was placed in a 100 mL round bottom flask. 2-phenyl-6-methylpyridine (23.0 g, 1360 mmol) and sodium carbonate (7.7 g, 70.0 mmol) was heated in a sand bath (temperature of sand 300° C.) for 24 hours under nitrogen. The reaction was then allowed to cool and methanol was added. The mixture was filtered and washed with methanol. The crude product was dissolved in dichloromethane and passed through a silica gel plug. The solvent was removed and the product was washed with methanol and then dried to give 7.2 g of product (74% yield).

-continued

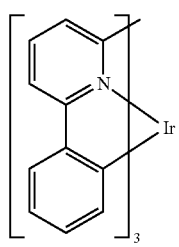

Step 5. Tris(2-phenyl-6-methylpyridine) iridium(III) (5.0 g, 7.2 mmol) was dissolved in 1 L of dichloromethane. N-bromosuccimide (2.6 g, 15.6 mmol) in dichloromethane was added drop wise over a 15-minute period. The reaction mixture was stirred at room temperature for 2 hours. The reaction volume was reduced to 200 mL and 200 mL of ethanol was added to precipitate the product. The solid was filtered and air dried overnight and used for the next step without further purification. 6.0 g of product was collected, which contained ~71% of the mono brominated compound.

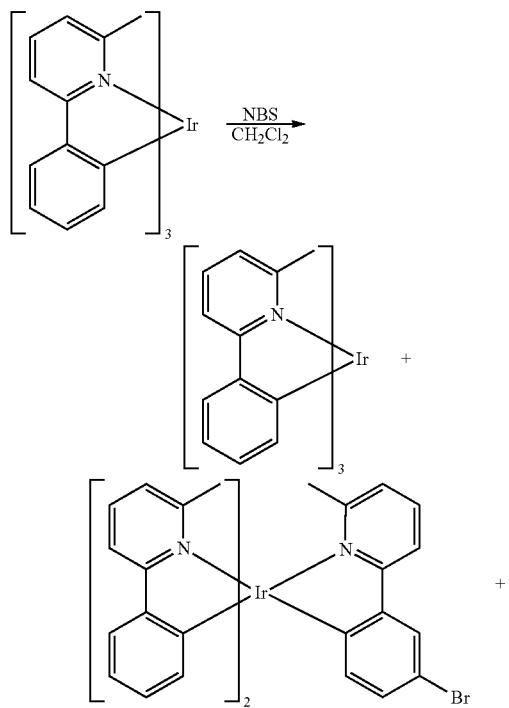

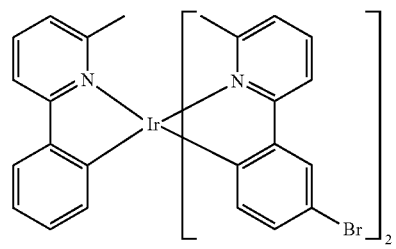

Step 6. The brominated mixture (6.2 g, 7.3 mmol), pinacolatodiboron (7.38 g, 29 mmol), potassium acetate (2.14 g, 21.8 mmol) and 300 mL of dioxane were mixed in a three-neck flask. The system was purged with nitrogen for 30 minutes. Pd(dppf)$_2$Cl$_2$ was then added (0.60 g, 0.74 mmol) to the reaction mixture. The reaction was heated to 90° C. for 15 hours. After the reaction was complete, the solvent was evaporated. The residue was chromatographed using a silica gel column with first 1:1 dichloromethane and hexanes as the eluent followed by 60:40 dichloromethane and hexanes. 0.8 g of product was obtained.

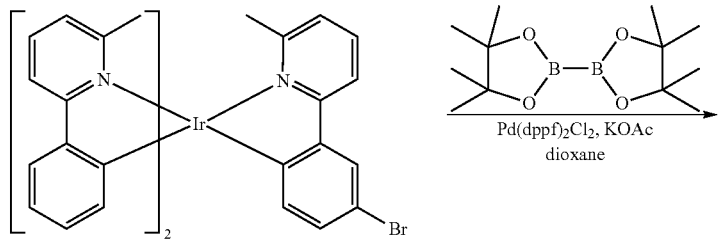

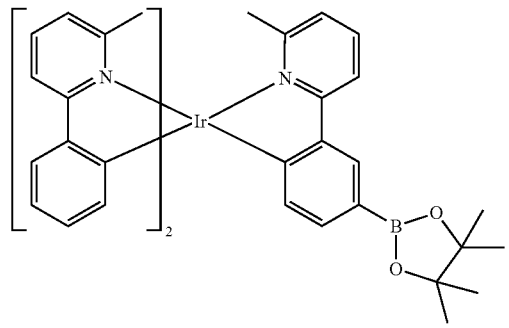

Step 7. A mixture of the Ir borate ester (0.8 g, 0.8 mmol), bromobenzene (1.32 g, 8.4 mmol), potassium phosphate (5.0 g, 21.7 mmol), 2-dicyclohexylphosphino-2',6'-dimethoxybiphenyl (0.30 g, 10 mol %) in 100 mL of toluene and 10 mL of water was purged with nitrogen for 30 minutes. Pd$_2$(dba)$_3$ (0.08 g, 2 mol %) was added to the reaction mixture which was then refluxed for 2 hours. The reaction was cooled to room temperature and was filtered through a Celite plug. The residue was chromatographed using a silica gel column with 1:1 dichloromethane and hexanes as the eluent. 0.7 g of product was obtained.

cool to room temperature and the organic phase was separated from the aqueous phase. The aqueous phase was washed with ethyl acetate and the organic fractions were combined and dried over magnesium sulfate and the solvent removed under vacuum. The product was column chromatographed using silica gel with ethyl acetate and hexanes as the eluent. The solvent was removed to give 12.0 g of a white solid (38% yield).

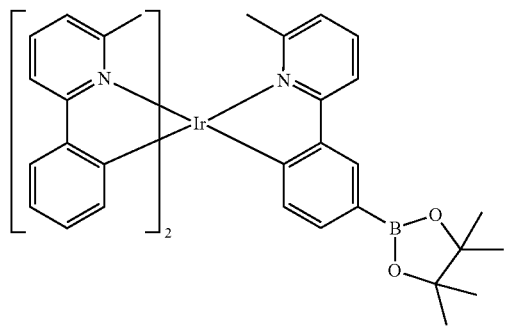

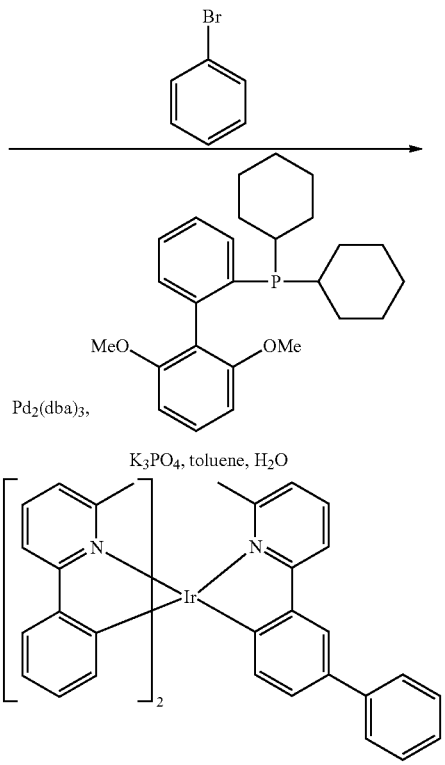

Compound 12

Compound 12

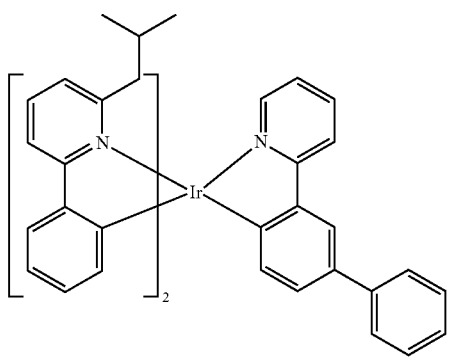

Step 1. A mixture of 2,6-dichloropyridine (25.0 g, 169 mmol), phenylboronic acid (22.7 g, 186 mmol), palladium acetate (0.9 g, 2.5 mol %)), triphenylphosphine (2.2 g, 5 mol %) and potassium carbonate (70.0 g, 507 mmol) in 300 mL of dimethoxyethane and 300 mL of water was purged with nitrogen for 30 minutes and then the solution was refluxed for 8 hours under nitrogen. The reaction was then allowed to

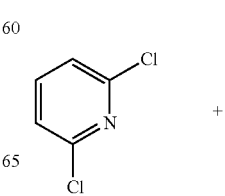

+

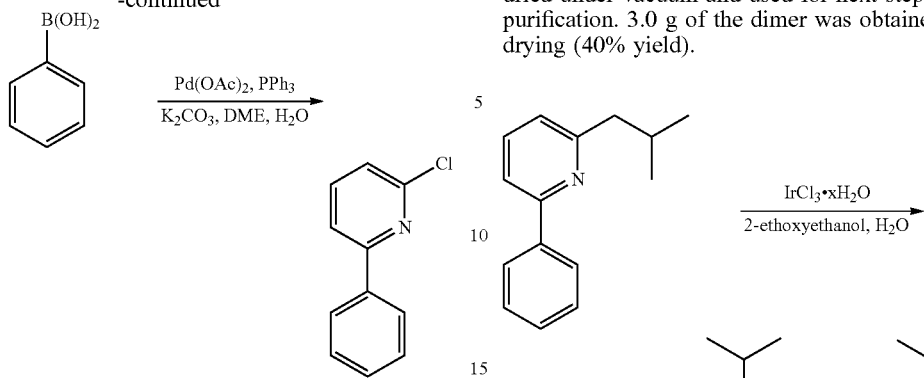

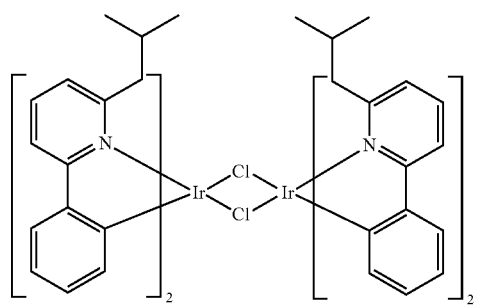

Step 2. A mixture of 2-phenyl-6-chloropyridine (12.0 g, 63.0 mmol), isobutylboronic acid (19.5 g, 190 mmol), Pd$_2$(dba)$_3$ (0.60 g, 1 mol %), 2-dicyclohexylphosphino-2',6'-dimethoxybiphenyl (0.8 g, 3 mol %), potassium phosphate monohydrate (40.0 g, 189 mmol) in 200 mL of toluene in a 500 mL round bottom flask was purged with nitrogen for 20 minutes and the mixture was refluxed in a nitrogen atmosphere overnight. The reaction mixture was allowed to cool and the solvent removed under vacuum. The crude product was chromatographed using a silica gel column with 2% ethyl acetate in hexanes as the eluent. The solvent was then removed under vacuum to give 12 g of product.

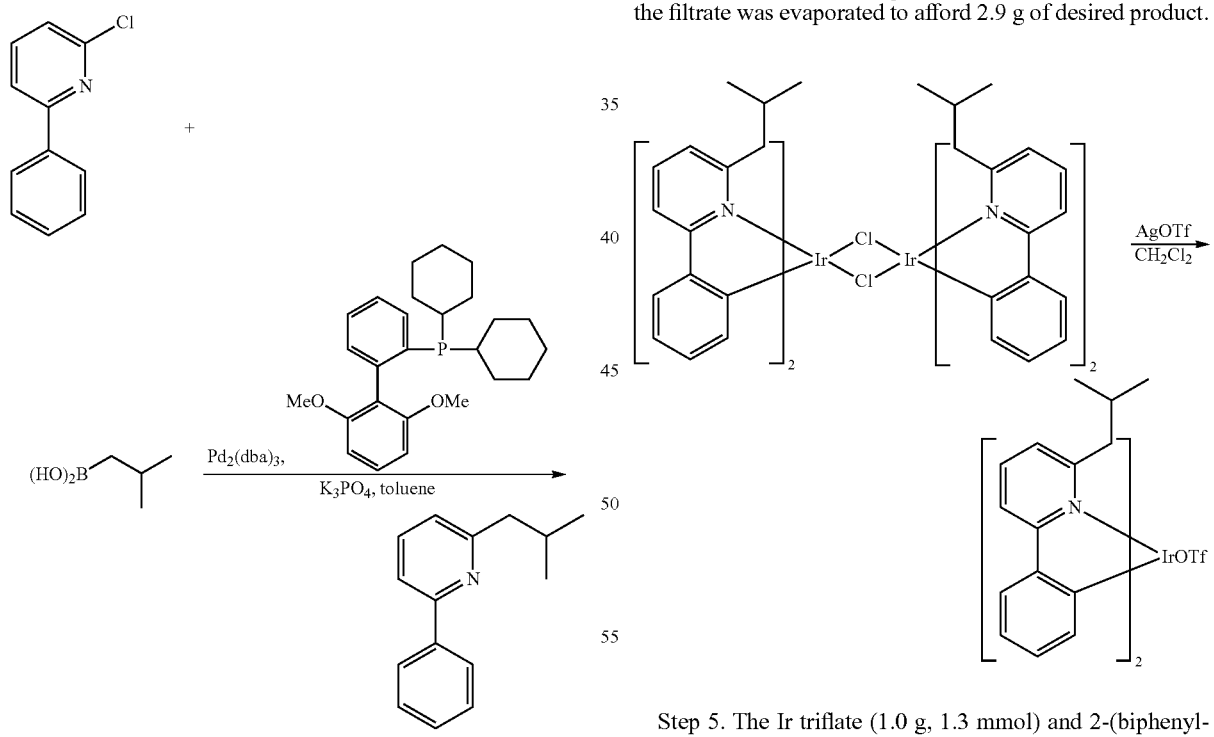

Step 3. A mixture of 2-phenyl-6-isobutylpyridine (5.0 g, 23.7 mmol) and iridium(III) chloride (2.08 g, 5.6 mmol) in 50 mL of a 3:1 mixture of 2-ethoxyethanol and water was purged with nitrogen for 10 minutes and then refluxed under a nitrogen for 16 hours. The reaction mixture was the allowed to cool to room temperature and the precipitate was filtered and washed with methanol. The dimer was then dried under vacuum and used for next step without further purification. 3.0 g of the dimer was obtained after vacuum drying (40% yield).

Step 4. The dimer (2.5 g, 1.9 mmol) was dissolved in 200 mL of dichloromethane in a 500 mL round bottom flask. A solution of silver triflate (1.0 g, 3.9 mmol) in 10 mL of methanol was added to the dimer solution. The reaction mixture was stirred overnight. The mixture was filtered and the filtrate was evaporated to afford 2.9 g of desired product.

Step 5. The Ir triflate (1.0 g, 1.3 mmol) and 2-(biphenyl-3-yl)pyridine (0.9 g, 3.4 mmol) was placed in a 100 mL round bottom flask. 10 mL of ethanol was added to the flask. The mixture was purged with nitrogen for 10 minutes and then refluxed under nitrogen for 16 hours. The reaction was allowed to cool to room temperature and isopropanol was added to precipitate the product. The reaction mixture was filtered and the residue was chromatographed using a silica gel column with 1:1 dichloromethane and hexanes as the eluent. 0.7 g of product was obtained,

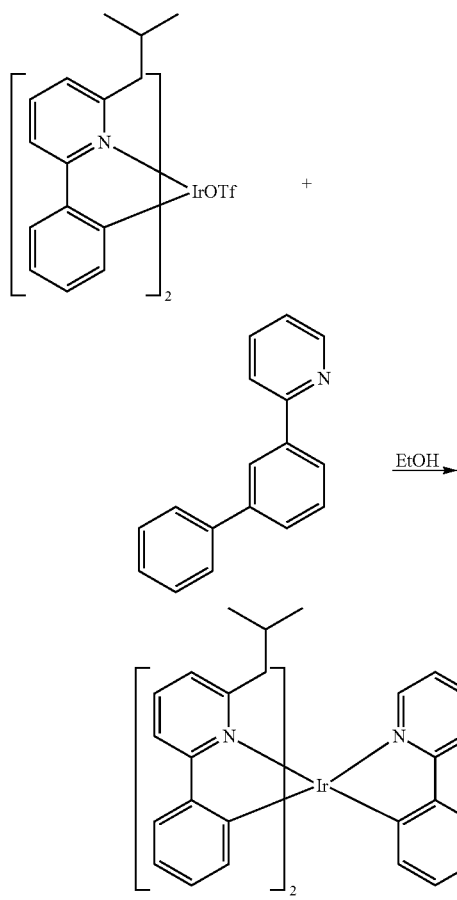

Compound 13

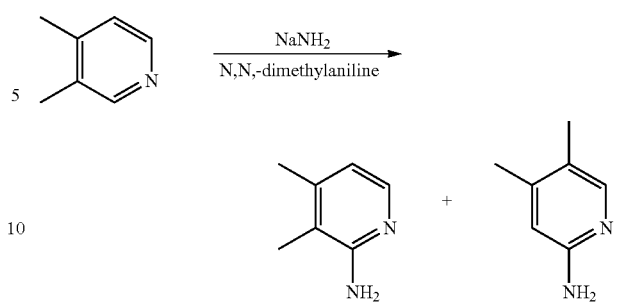

Step 2. 8.0 g (0.065 mol) of the Step 1 mixture was added to ~25 mL of 60% HBr, then stirred under −15° C. to −17° C. 31.0 g of pre-cooled (~0° C.) Br₂ (0.2 mol) was added drop wise and the mixture was stirred for 20 minutes. Pre-cooled (0° C.) NaNO₂ solution of 11.4 g (0.16 mol) NaNO₂ dissolved in 20 mL of water was added drop wise into the reaction mixture at −15° C. to −17° C. After addition, the reaction was stirred for one hour. Ice-cooled 25% NaOH solution was added slowly until the solution became basic. The mixture was extracted with ethyl acetate. The organic extract was concentrated and distilled under vacuum. 10.7 g (88% yield) of solid mixture of 2-bromo-3,4-dimethylpyridine (~78%) and 2-bromo-4,5-dimethyl-pyridine (~22%) was obtained which was used for next step without purification.

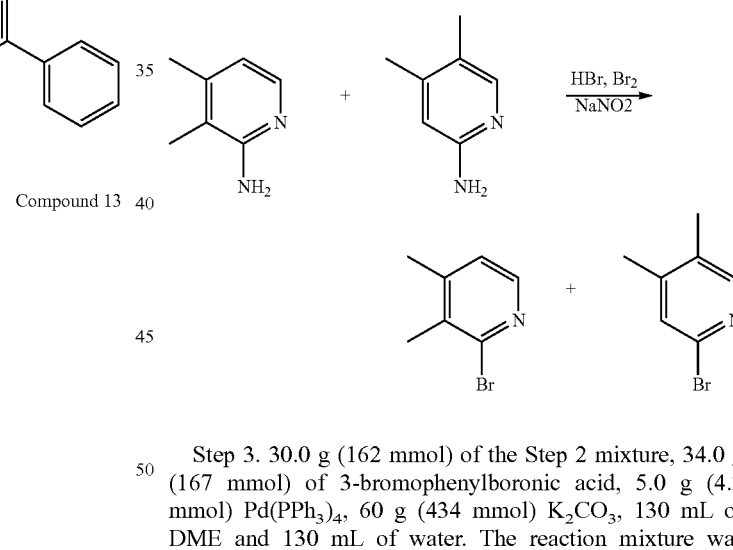

Step 3. 30.0 g (162 mmol) of the Step 2 mixture, 34.0 g (167 mmol) of 3-bromophenylboronic acid, 5.0 g (4.3 mmol) Pd(PPh₃)₄, 60 g (434 mmol) K₂CO₃, 130 mL of DME and 130 mL of water. The reaction mixture was refluxed for 20 hours and the organic extract was purified by silica gel column with 10% ethyl acetate in hexanes solvent as the eluent followed by distillation. The two isomers were further separated by recrystallization in hexanes.

Step 1. 100 g (0.94 mol) of 3,4-dimethylpyridine and 40 g (1.0 mol) of sodium amide was added to 240 mL of N,N,-dimethylaniline. The reaction mixture was heated with stirring under nitrogen for 7 hours at 150° C. After cooling, the reaction mixture was added to 400 mL of ice water. The mixture was extracted with ethyl acetate. The organic phase was concentrated and fractionally distilled. 40 g (35% yield) of white solid mixture of 2-aminuteso-3,4-dimethylpyridine (~78% by GC) and 2-aminuteso-4,5-dimethylpyridine (~22% by GC) was obtained which was used for next step without further purification.

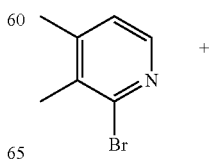

-continued

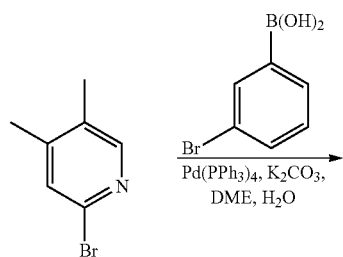

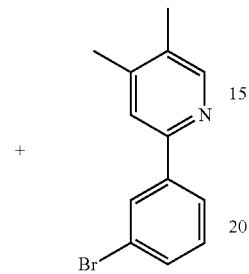

Step 4. 1.7 g (6.5 mmol) of 2-(3-bromophenyl)-3,4-dimethylpyridine, 1.2 g (7.8 mmol) of 3,-5-dimethylphenylboronic acid, 235 mg (0.203 mmol) of Pd(PPh$_3$)$_4$, 2.8 g (20.2 mmol) K$_2$CO$_3$, 50 mL of DME and 50 mL of water were charged in a 200 mL flask and heated to reflux under nitrogen for overnight. The organic extract was purified by silica gel column with dichloromethane as eluent. 1.5 g (81% yield) of product was obtained.

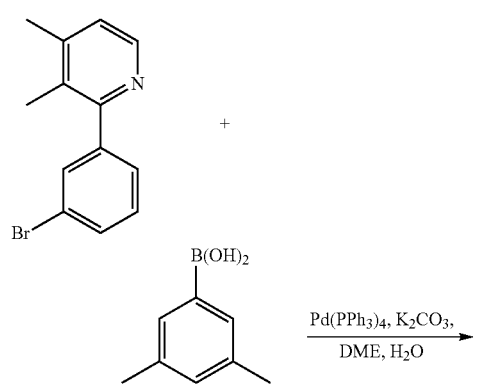

Step 5. 4.1 g (14.2 mmol) of the ligand from Step 4, 1.4 g (2.86 mmol) of Ir(acac)$_3$ were added in a Schlenk tube. The tube was heated to 250° C. for 30 hours. The reaction residue was purified by silica gel column. 2.2 g (66% yield) of product was obtained.

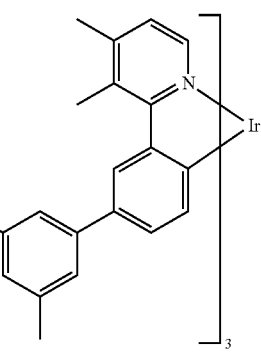

Compound 14

Compound 14

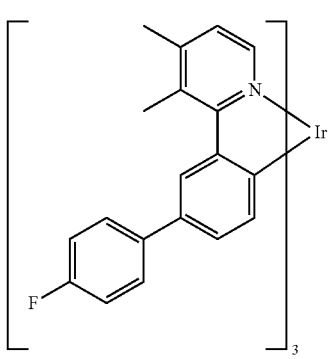

Step 1. 3.0 g (11.4 mmol) of 2-(3-bromophenyl)-3,4-dimethylpyridine from Step 3 of Compound 36, 1.8 g (12.8 mmol) of 4-fluorophenylboronic acid, 0.4 g (0.34 mmol) of Pd(PPh$_3$)$_4$, 4.8 g (34.7 mmol), K$_2$CO$_3$, 100 mL of DME and 100 of mL water were charged in a 500 mL flask and heated to reflux under nitrogen for overnight. The reaction mixture was purified by silica gel column with dichloromethane as elute. 2.5 g (80% yield) of product was obtained.

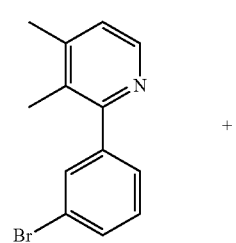

-continued

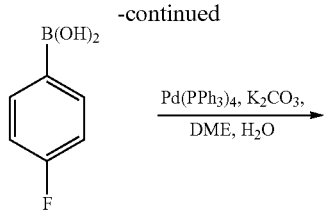

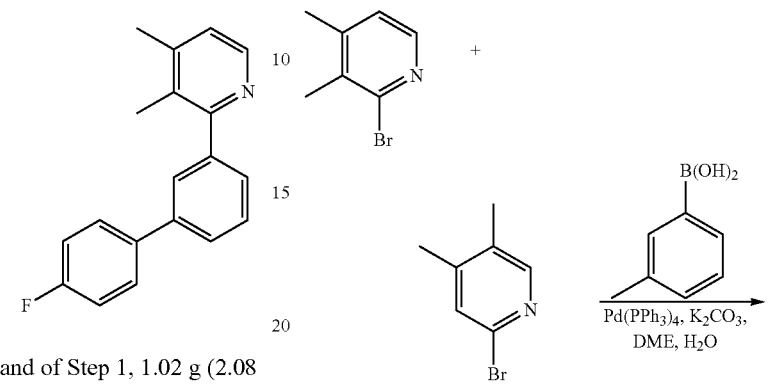

Step 5. 2.3 g (8.3 mmol) of ligand of Step 1, 1.02 g (2.08 mmol) of Ir(acac)₃ were added in a Schlenk tube. The tube was heated to 250° C. for 30 hours. The reaction residue was purified by silica gel column. 1.3 g (63%) of solid product was obtained.

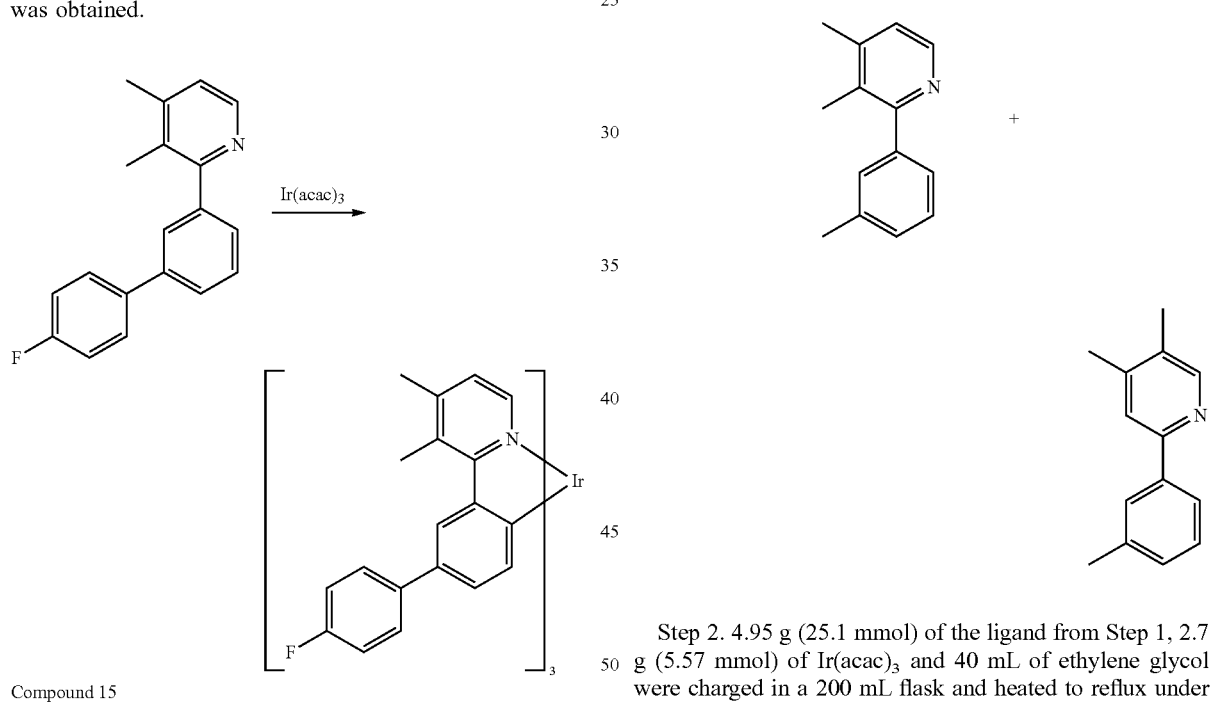

Compound 15

Compound 15

Step 1. 20.0 g (107.5 mol) of the mixture from Step 2 of Compound 36, 17.7 g (129 mmol) of 3-methylphenylboronic acid, 3.7 g (3.2 mol) of (PPh₃)₄, 44 g (0.321 mol) of K₂CO₃, 100 mL of DME and 100 mL of water were mixed and refluxed for 20 hours. The organic extract was purified by silica gel column with 10% ethyl acetate in hexanes as eluent. 5.1 g of 2-(3-methyl)-4,5-dimethylpyridine was obtained which was confirmed by NMR and GCMS.

Step 2. 4.95 g (25.1 mmol) of the ligand from Step 1, 2.7 g (5.57 mmol) of Ir(acac)₃ and 40 mL of ethylene glycol were charged in a 200 mL flask and heated to reflux under nitrogen for overnight. The reaction residue was purified by silica gel column with dichloromethane as eluent. 2.6 g (60% yield) of product was obtained.

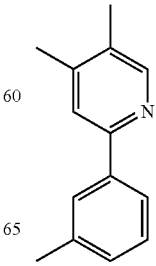

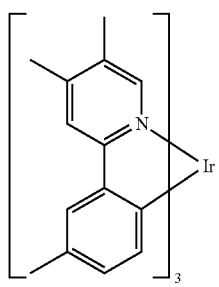

Compound 16

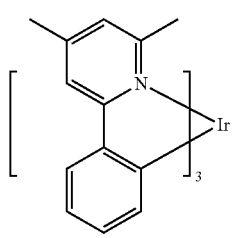

Compound 16

Step 1. Concentrated sulfuric acid (27 mL) was dissolved in 160 mL water and cooled to 0° C. Then 4,6-dimethyl-2-aminuteso-pyridine (25 g, 205 mmol) was added into the solution. A solution of sodium nitrite (18.4 g, 266 mmol) in 40 mL of water was then slowly added (the temperature was controlled to be below 5° C.). After all the sodium nitrite was added, the mixture was stirred at 0° C. for 45 minutes, then heated to 95° C. for 15 minutes. After the reaction mixture was cooled to room temperature, 50% w/w NaOH/water was used to adjust the pH value to the range of 6.5-7.0. The precipitate was collected by filtration and redissolved in dichloromethane. The aqueous filtrate was extracted by dichloromethane. The organic extracts were combined and dried with $MgSO_4$. The solvent was evaporated under reduced pressure. The crude product was recrystallized from 400 mL of ethyl acetate to give 19.2 g (76% yield) of a yellow solid.

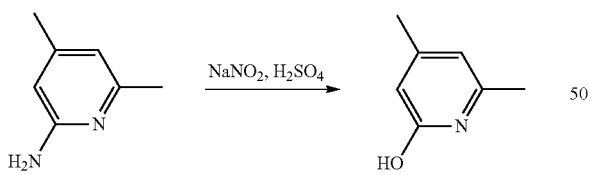

Step 2. 4,6-dimethylpyridin-2-ol (17 g, 138 mmol) was dissolved in 300 mL of pyridine. The mixture was cooled to −10° C. by an acetone/ice bath. The reaction was kept under nitrogen by bubbling nitrogen into the solution. Triflate anhydride (47 g, 28 mL, 166 mmol) was added. The mixture was stirred at 0° C. for 1 hour and then poured into 300 mL of saturated sodium bicarbonate aqueous solution (some gas will be released). The mixture was extracted by dichloromethane. The organic extract was dried by $MgSO_4$ and concentrated under reduced pressure to give 33 g of a brown oil (94% yield). The crude product was used for next step without further purification.

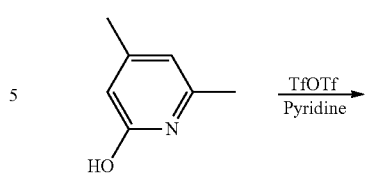

Step 3. 4,6-dimethylpyridin-2-yl trifluoromethanesulfonate (18.8 g, 74 mmol), phenylboronic acid (10.8 g. 88 mmol), potassium phosphate tribasic (56 g, 264 mmol), toluene (550 mL) and water 55 (mL) were mixed in one 1 L 3-neck flask. The system was purged with nitrogen for 15 minutes before $Pd_2(dba)_3$ (0.81 g, 0.88 mmol) and 2-dicyclohexylphosphino-2',6'-dimethoxybiphenyl (1.45 g, 3.5 mmol) were added. The system was purged with nitrogen for another 10 minutes, then refluxed for four hours. After the reaction was cooled to room temperature, the organic layer was collected, dried with $MgSO_4$ and evaporated under reduced pressure. The crude product was purified by silica column eluted with 10% ethyl acetate in hexanes to give 12.0 g of product (90% yield).

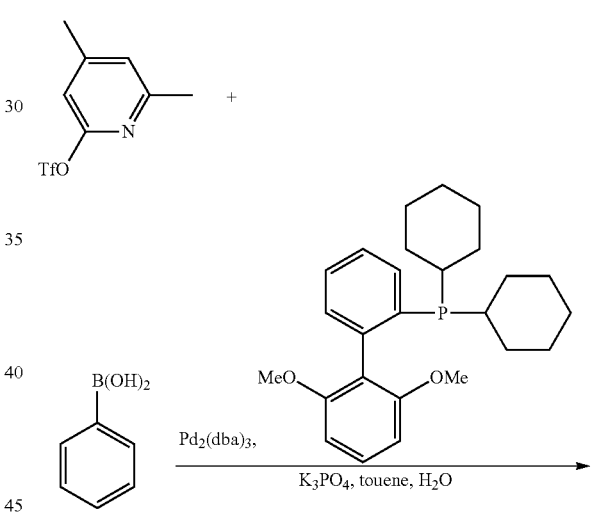

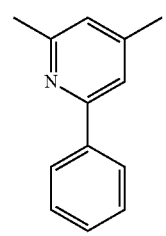

Step 4. 2.0 g (10.9 mmol) of Step 3 ligand, and 1.1 g (2.2 mmol) of $Ir(acac)_3$ were charged in a Schlenk tube and heated to 250° C. under nitrogen with stirring for 20 hours. The reaction residue was purified by silica gel column with dichloromethane 50% in hexanes as the eluent. 0.6 g (34% yield) product was obtained.

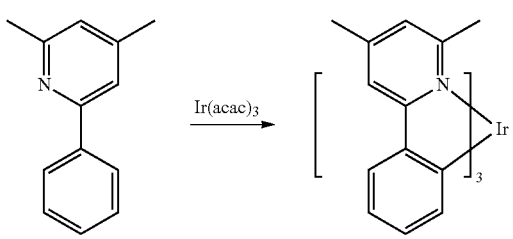

Compound 17

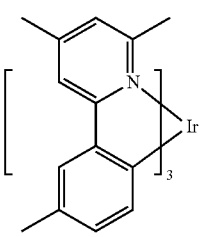

Compound 17

Step 1. 4,6-dimethylpyridin-2-yl trifluoromethanesulfonate (18.8 g, 74 mmol), m-tolylboronic acid (12 g, 88 mmol), potassium phosphate tribasic (56 g, 264 mmol), toluene (550 mL) and water (55 mL) were mixed in one 1 L 3-neck flask. The system was purged with nitrogen for 15 minutes before $Pd_2(dba)_3$ (0.81 g, 0.88 mmol) and 2-dicyclohexylphosphino-2',6'-dimethoxybiphenyl (1.45 g, 3.5 mmol) were added. The system was purged with nitrogen for another 10 minutes, then refluxed for 4 hours. After the reaction was cooled to room temperature, the organic layer was collected, dried with $MgSO_4$ and evaporated under reduced pressure. The crude product was purified by silica column eluted with 2% ethyl acetate in hexanes to give 13.3 g of a white solid (91% yield).

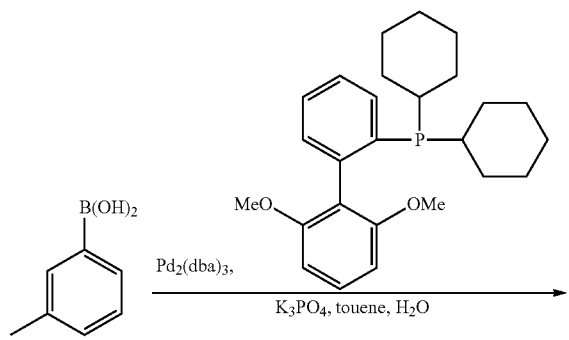

-continued

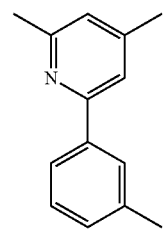

Step 2. The product from Step 1 (10 g, 50.6 mmol), iridium chloride (4.4 g, 12.6 mmol), 2-ethoxyethanol (180 mL) and water (60 mL) were mixed in a 500 mL 3-neck flask. The system was purged with nitrogen for 15 minutes, then refluxed for overnight. After the reaction was cooled to room temperature, the solvent was evaporated under reduced pressure. The residue was washed with methanol to give 3.7 g of dark a red solid (24% yield).

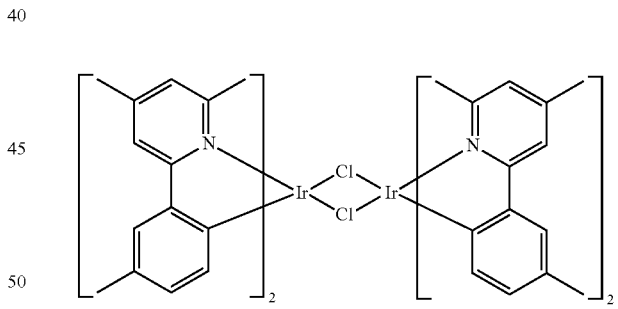

Step 3. The dimer (2.7 g, 2.2 mmol), dipivaloylmethane (4.0 g, 4.5 mL, 21.6 mmol), sodium carbonate (2.3 g, 21.6 mmol) and 2-ethoxyethanol (100 mL) were mixed in a 300 mL 3-neck flask. The system was purged with nitrogen for 20 minutes. The reaction then was refluxed for 3 hours. After cooled to room temperature, the mixture was run through a Celite plug and washed by methanol. After the yellow color in the Celite was washed away, dichloromethane was used to wash the Celite plug until filtrate turned colorless. The dichloromethane filtrate was collected and evaporated under reduced pressure. The crude product was purified by silica column (pretreated by 20% triethylamine in hexanes) with up to 100% dichloromethane in hexanes to give 2 g of a yellow solid (60% yield).

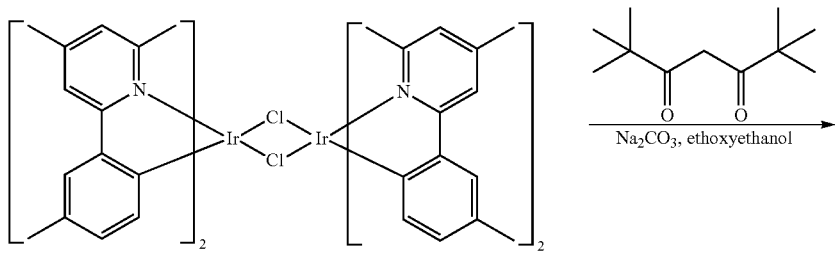

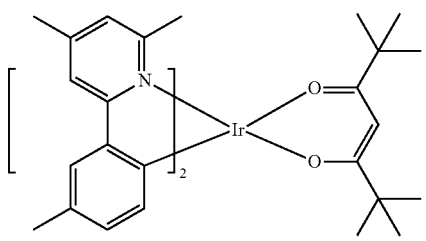

Step 4. The product from Step 3 (1.8 g, 2.3 mmol), 2,4-dimethyl-6-m-tolylpyridine (4.5 g, 22.8 mmol), sodium carbonate (1.2 g. 11.4 mmol) were mixed. The system was vacuumed and refilled with nitrogen 3 times. The mixture was heat at 270° C. (sand bath temperature) for 3 hours. After cooled to room temperature, the mixture was dissolved in dichloromethane and put through a Celite plug. The Celite plug was washed with dichloromethane. The combined filtration was evaporated under reduced pressure. The crude product was purified by silica column eluted 1:2 dichloromethane and hexanes to give 1 g of a yellow solid. The product was further purified by high vacuum sublimation at 240° C.

-continued

Compound 18

Compound 18

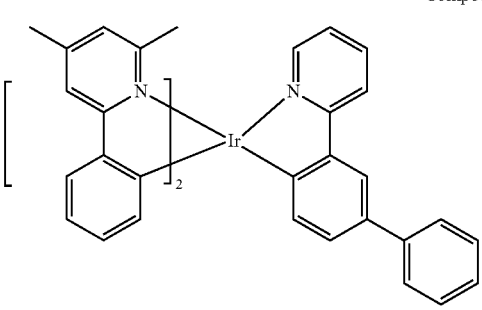

Step 1. A mixture of 2-bromopyridine (8.66 g, 54.8 mmol), 3-methoxyphenylboronic acid (10 g, 65.8 mmol), triphenylphosphine (1.44 g. 5.48 mmol), potassium carbonate (18.9 g. 137 mmol) in of 100 mL dimethoxyethane and 66 mL of water was purged with nitrogen for 20 minutes. Then palladium acetate was added (0.61 g, 2.74 mmol). The reaction mixture was heated to reflux overnight under nitrogen. The reaction mixture was cooled and water and ethyl acetate were added. The layers were separated and the aqueous layer was extracted with ethyl acetate. The organic extracts were dried over magnesium sulfate, filtered, and evaporated to a residue. The residue was purified by column chromatography eluting with 0 to 20% ethyl acetate/hexanes. 9.7 g of a clear oil (96% yield) was obtained.

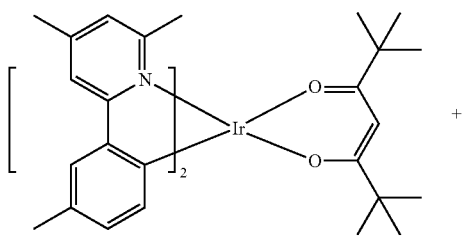

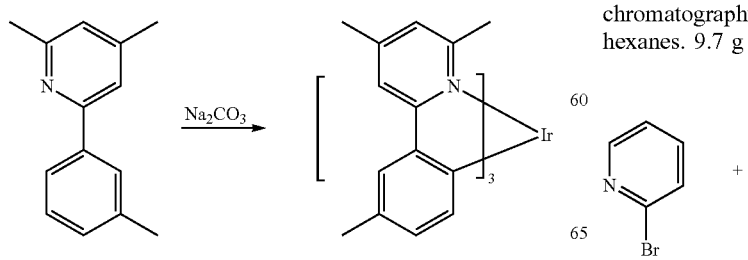

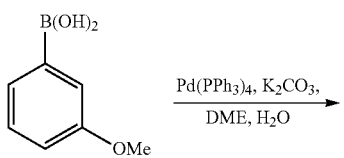

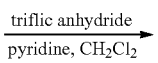

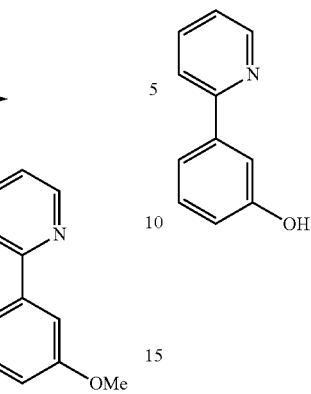

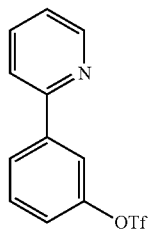

Step 2. A mixture of 2-(3-methoxyphenyl)pyridine (9.7 g, 52.37 mmol) and pyridine hydrochloride (72.6 g, 628.44 mmol) was heated to 220° C. for 2 hours. Water was added to the cooled mixture and then extracted with dichloromethane twice. The organic extracts were dried over magnesium sulfate, filtered, and evaporated to a residue. The residue was purified by column chromatography eluting with 0, 1, and 2% methanol/dichloromethane, followed by vacuum distillation and recrystallization from 2:1 hexanes/ethyl acetate. 5 g of a white solid (56% yield) was obtained.

Step 4. 10.7 g (58.5 mmol) of 2-phenyl-4,6-dimethylpyridine. 5.4 g (14.6 mmol) of iridium chloride, 2-ethoxyethanol of 150 mL and water of 50 mL were mixed in a 500 mL 3-neck flask. The system was purged with nitrogen for 15 minutes, then refluxed for overnight. After the reaction was cooled to room temperature, the solvent was evaporated under reduced pressure. The residue was washed with methanol to give 4.1 g of a dark red solid (46% yield).

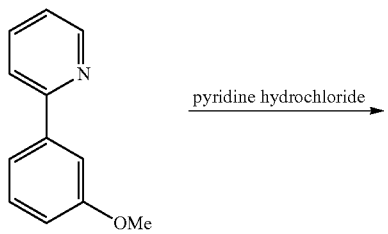

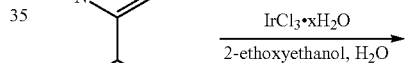

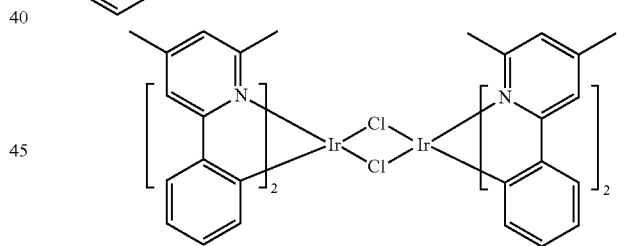

Step 3. A solution of 3-(pyridin-2-yl)phenol (5 g, 29.21 mmol) in 100 mL of dichloromethane was prepared. To this solution was added pyridine (4.7 mL, 58.42 mmol) and the solution was cooled in an ice-salt bath. To this solution was added a solution of trifluoromethanesulfonic anhydride (9.8 mL. 58.42 mmol) in 20 mL of dichloromethane drop wise. The reaction was allowed to warm slowly and was complete after 2 hours. Water and dichloromethane were added and the layers were separated. The aqueous layer was extracted with dichloromethane. The organic extracts were dried over magnesium sulfate, filtered and evaporated to a residue. The residue was purified by column chromatography eluting with 5, 10, and 15% ethyl acetate/hexanes. 8 g of a clear liquid (90% yield) was obtained.

Step 5. 3.0 g of the dimer (2.5 mmol) was dissolved in 200 mL of dichloromethane and 1.32 g (5.1 mmol) of AgOTf and 10 mL of methanol were. The reaction mixture was stirred for 30 minutes at room temperature. The residue was filtered, washed with methanol (2×50 mL). The filtrate was evaporated to give a yellow solid which was used in next step without any purification.

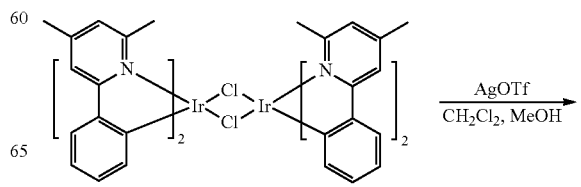

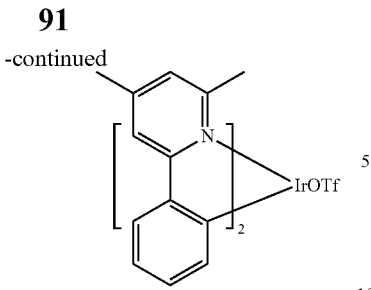

Step 6. The product from Step 5 was added with 3.1 g of (10.0 mmol) the product of Step 3 and 150 mL 2-methoxyethanol. The reaction mixture was heated to 90° C. for 18 hours. The reaction mixture was cooled down and purified by silica gel column with 40% dichloromethane in hexanes as eluent. 1.6 g of a yellow solid was obtained.

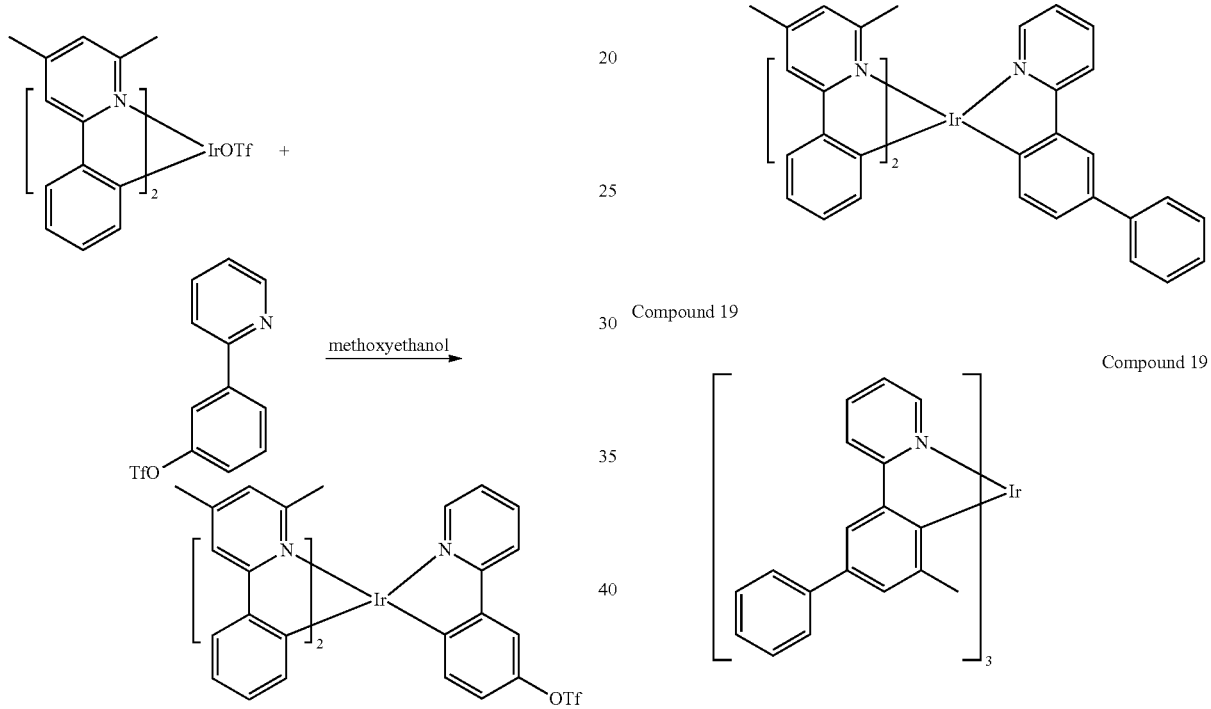

Step 9. 1.6 g (1.86 mmol) of the Step 6 product, 0.86 g (7.0 mmol) of phenylboronic acid, 35 mg (0.037 mmol) of Pd$_2$(dba)$_3$, 62 mg (0.149 mmol) of 2-dicyclohexylphosphino-2',6'-dimethoxybiphenyl, 1.3 g (5.6 mmol) of potassium phosphate tribasic monohydrate and 150 mL of dry toluene were charged in a 3-neck flask. Nitrogen was purged through the reaction mixture for 40 minutes, then heated to reflux for overnight. The organic extract was purified by silica gel column with 30% dichloromethane in hexanes as the eluent. 1.3 g (~90% yield) of product was obtained.

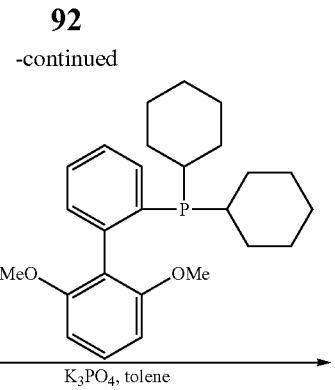

Compound 19

Compound 19

Step 1. 25 g (98 mmol) of 3,5-dibromomethylbenzene, 12.2 g (98 mmol) of phenylboronic acid, 3.4 g (2.9 mmol) of Pd(PPh$_3$)$_4$, 41 g (297 mmol) of K$_2$CO$_3$, 150 mL of DME and 150 mL of water were charged in a 500 mL flask. The reaction mixture was heated to reflux under nitrogen for overnight. The organic extract was purified by silica gel column. 16 g (66% yield) of product was obtained.

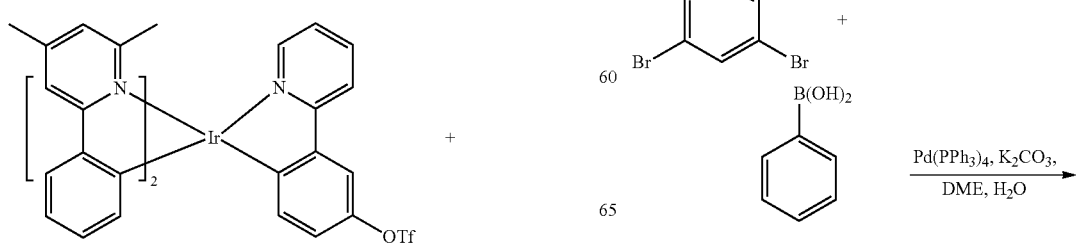

-continued

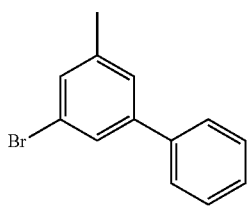

Step 2. 10.2 g (41.4 mmol) of the Step 1 product, 100 mL (50 mmol) of 0.5 M pyridinylzinc bromide in THF and 1.5 g (1.29 mmol) of Pd(PPh$_3$)$_4$ were added in a dry 200 mL flask under nitrogen. The reaction was refluxed under nitrogen for 5 hours and the organic extract was purified by silica gel column with 10% ethyl acetate in hexanes as eluent. 8.5 g (85% yield) of product was obtained.

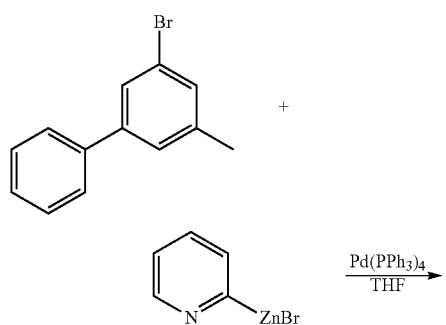

Step 3. 5.2 g (21.2 mmol) of the product from Step 2, 2 g (4.24 mmol) of Ir(acac)$_3$ were charged in a Schlenk tube and heated to 280° C. for 48 hours under nitrogen. The reaction residue was purified by silica gel column. 0.3 g (7.6% yield) of product was obtained.

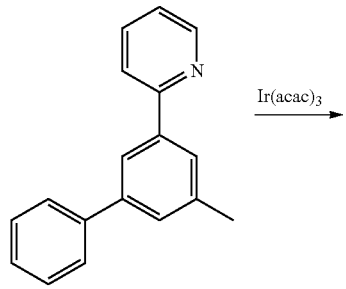

-continued

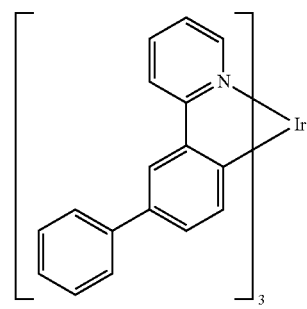

Compound 20

Compound 20

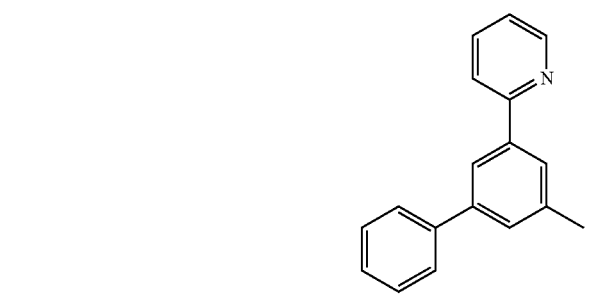

Step 1. A mixture of 2-bromopyridine (40 g, 253 mmol), 3-bromophenylboronic acid (61.0 g, 303.8 mmol), triphenylphosphine (6.64 g, 25.3 mmol), potassium carbonate (87.4 g, 632.5 mmol) in of 300 mL of dimethoxyethane and 200 mL of water was purged with nitrogen for 20 minutes. Then palladium acetate (2.84 g, 12.65 mmol) was added. The reaction mixture was heated to reflux under nitrogen. The reaction mixture was cooled and water and ethyl acetate were added. The layers were separated and the aqueous layer was extracted with ethyl acetate. The organic extracts were dried over magnesium sulfate, filtered, and evaporated to a brown oil which was purified by column chromatography eluting with 0 to 40% ethyl acetate/hexanes followed by distillation under vacuum. 45.1 g (52% yield) of product was obtained.

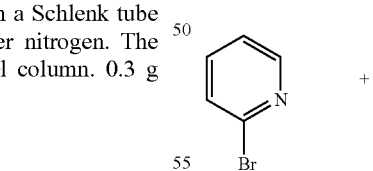

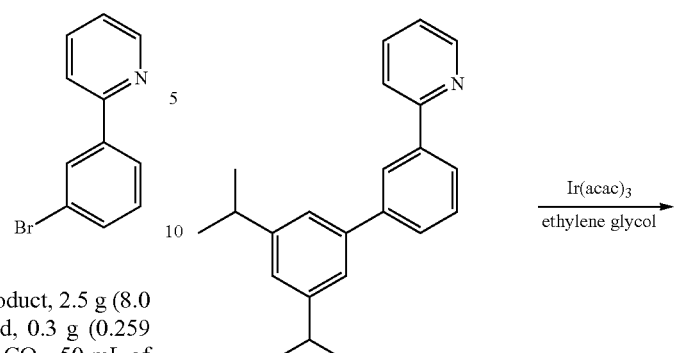

Step 2. 2.5 g (10.7 mmol) of the Step 1 product, 2.5 g (8.0 mmol) of 3,5-diisopropylphenylboronic acid, 0.3 g (0.259 mmol) of Pd(PPh$_3$)$_4$, 3.6 g (26 mmol) of K$_2$CO$_3$, 50 mL of DME and 50 mL of water were charged in a 200 mL flask. The reaction mixture was heated to reflux under nitrogen for overnight. The organic extract was purified by silica gel column. 1.4 g (56% yield) of product was obtained.

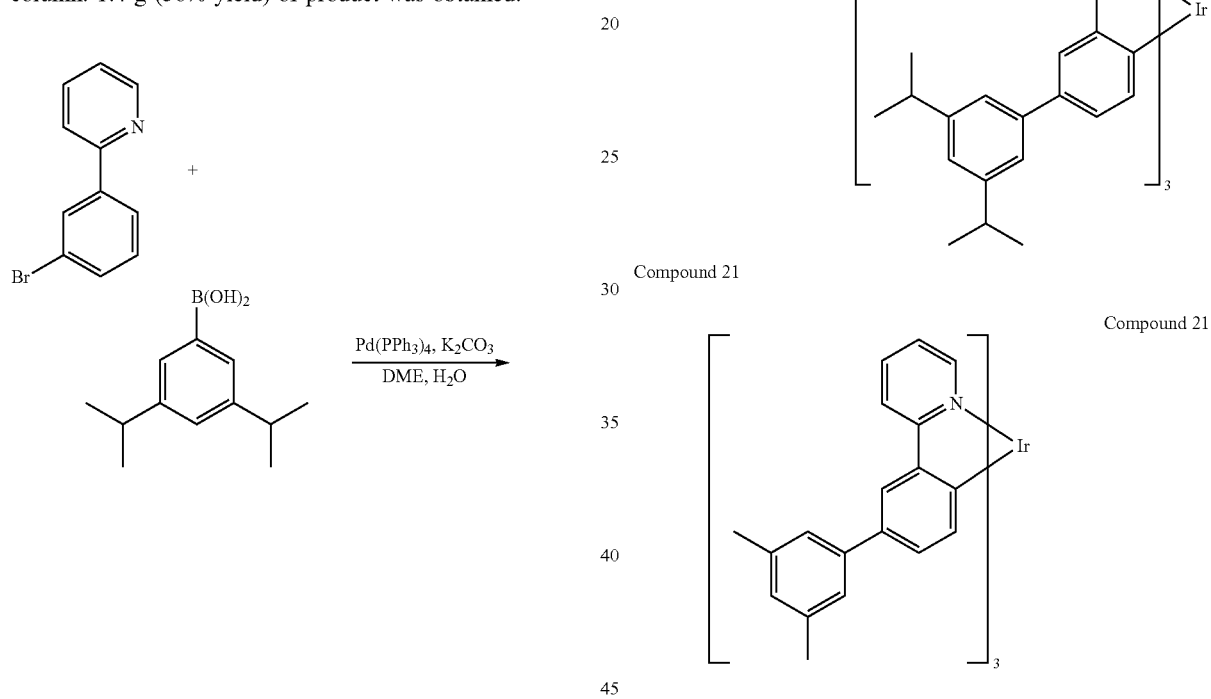

Compound 21

Compound 21

Step 1. 2.5 g (10.7 mmol) of 2-(3-bromophenyl)pyridine, 2.4 g (16 mmol) of 3,5-dimethylphenylboronic acid, 0.37 g (0.321 mmol) of Pd(PPh$_3$)$_4$, 4.5 g (32.6 mmol) of K$_2$CO$_3$, 50 mL of DME and 50 mL of water were charged in a 200 mL flask. The reaction mixture was heated to reflux under nitrogen for overnight. The organic extract was purified by silica gel column. 2.3 g (83% yield) of product was obtained.

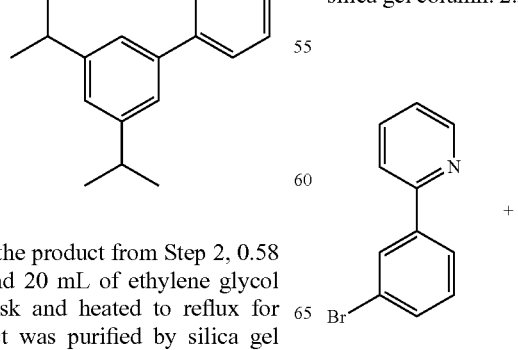

Step 3. 1.3 g (4.1 mmol) of the product from Step 2, 0.58 g (1.17 mmol) of Ir(acac)$_3$ and 20 mL of ethylene glycol were added in a 100 mL flask and heated to reflux for overnight. The organic extract was purified by silica gel column. 0.7 g (56% yield) of product was obtained.

97
-continued

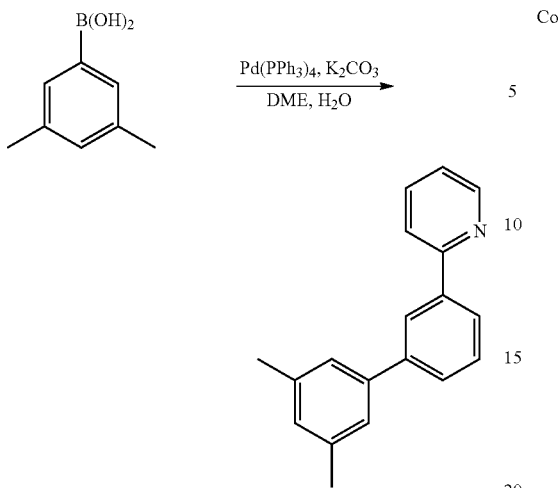

Step 2. 2.0 g (7.68 mmol) the product of Step 1, 1.1 g (2.14 mmol) of Ir(acac)₃ and 20 mL of ethylene glycol were added in a 100 mL flask and heated to reflux for overnight. The organic extract was purified by silica gel column. 1.7 g (86% yield) of product was obtained.

98
-continued

Compound 22

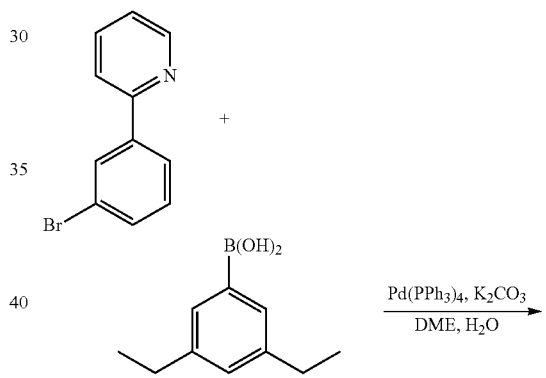

Compound 22

Step 1. 3.5 g (15.0 mmol) of 2-(3-bromophenyl)pyridine, 3.5 g (19.7 mmol) of 3,5-diethylphenylboronic acid, 0.4 g (0.345 mmol) of Pd(PPh₃)₄, 6.2 g (44.9 mmol) of K₂CO₃, 100 mL of DME and 100 mL of water were charged in a 250 mL flask. The reaction mixture was heated to reflux under nitrogen for overnight. The organic extract was purified by silica gel column. 3.2 g (74% yield) of product was obtained.

Step 2. 2.2 g (7.64 mmol) of the product from Step 1, 1.04 g (2.12 mmol) of Ir(acac)₃ and 30 mL of ethylene glycol were added in a 100 mL flask and heated to reflux for overnight. The organic extract was purified by silica gel column. 1.5 (67% yield) of product was obtained.

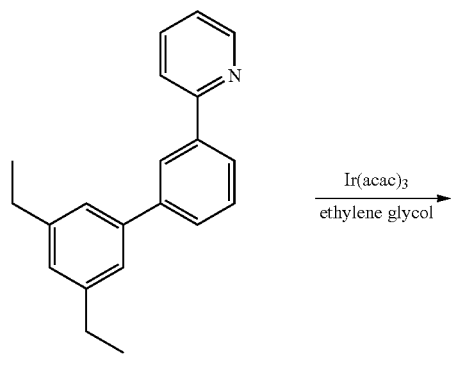

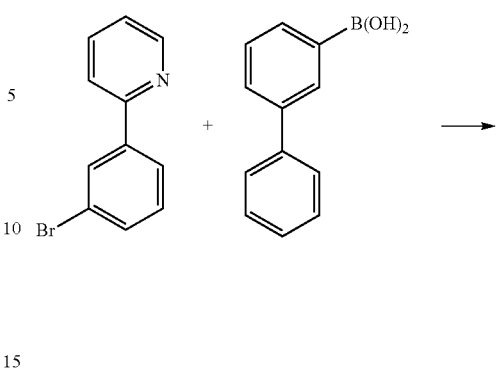

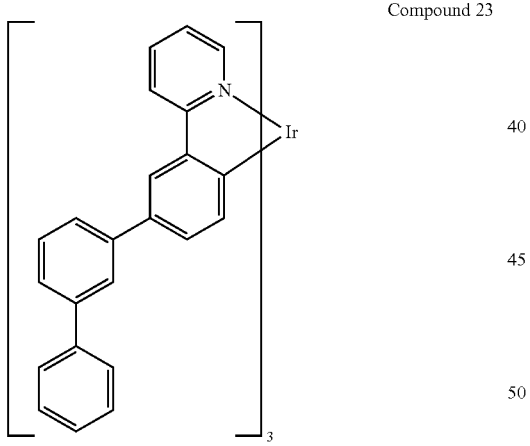

Compound 23

Compound 23

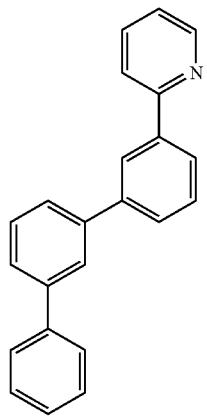

Step 2. 1.5 g (4.8 mmol) of the Step 1 ligand, 0.68 g (1.39 mmol) of Ir(acac)₃ and 25 mL of ethylene glycol were charged in a 100 mL flask. The reaction mixture was heated to reflux under nitrogen for overnight. The reaction was cooled down and filtered with methanol washing 3 times (3×50 mL). The solid was purified by silica gel column to yield 0.8 g (51%) of product.

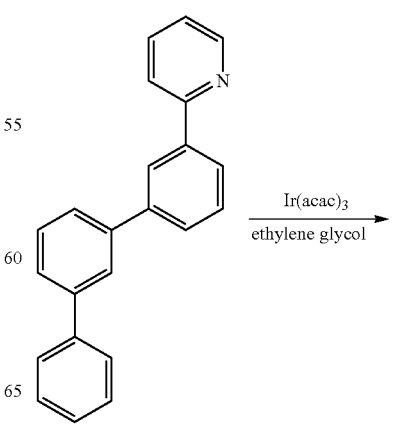

Step 1. A mixture of 2-(3-bromophenyl)pyridine (15 g, 64 mmol), 3-biphenylboronic acid (13.70 g, 69 mmol), potassium carbonate (27 g, 195 mmol) in 100 mL of dimethoxyethane and 60 mL of water was purged with nitrogen for 20 minutes. Pd(PPh₃)₄ (2.3 g, 2 mmol) was then added and the reaction mixture was heated to reflux overnight under nitrogen. The next day the reaction mixture was cooled and diluted with water and ethyl acetate. The layers were separated and the aqueous layer was extracted with ethyl acetate. The organic layers were dried over magnesium sulfate, filtered, evaporated to a red oil. The oil was purified by column chromatography eluting with 5 to 30% ethyl acetate/hexanes to yield 19 g of a clear oil as the product.

-continued

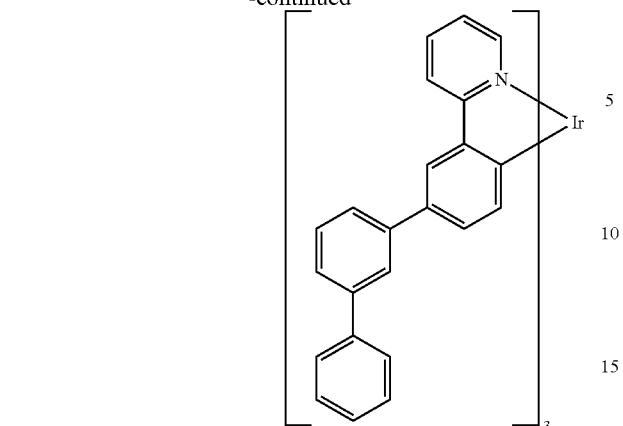

Compound 24

Compound 24

Step 1. A mixture of 2-(3-bromophenyl)pyridine (12.2 g, 52.10 mmol), 3-(4,4,5,5-tetramethyl-1,3,2-dioxaborolan-2-yl)phenol (13.76 g, 62.53 mmol), 2-dicyclohexylphosphino-2',6'-dimethoxybiphenyl (856 mg, 2.08 mmol), potassium phosphate tribasic monohydrate (36 g, 156.3 mmol) in 180 mL of dioxane and 18 mL of water was purged with nitrogen for 20 minutes. Then Pd$_2$(dba)$_3$ was added (477 mg, 0.52 mmol). The reaction mixture was heated at 100° C. for 3 hours under nitrogen, then allowed to cool to room temperature overnight. Water was added to the reaction mixture and the mixture was extracted 3 times with ethyl acetate. The organic extracts were dried over magnesium sulfate, filtered and evaporated to a residue. The residue was purified by column chromatography eluting with 20 and 40% ethyl acetate/hexanes to yield 12.5 g of a yellow oil (97% yield) as the product.

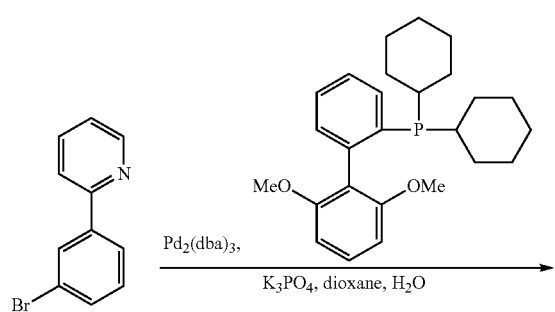

-continued

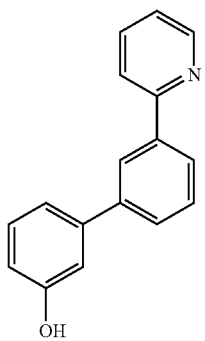

Step 2. 12.5 g (50.6 mmol) of the Step 1 product, 12 mL of pyridine and 200 mL of dichloromethane were mixed in a 500 mL round bottle flask at 0° C. 14.3 g (101.2 mmol) of trific anhydride was added. The mixture was stirred for 30 minutes at 0° C. and room temperature for 1 hour. The reaction mixture was washed with water several times. 19.0 g (~100% yield) of product was obtained after evaporation of solvent.

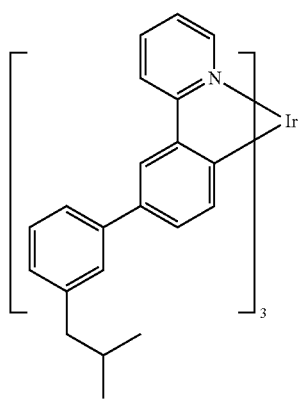

trific anhydride
pyridine, CH$_2$Cl$_2$

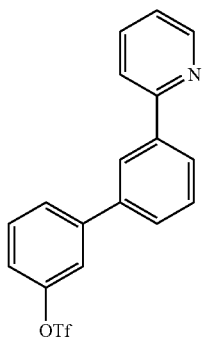

Step 3. 8.8 g (23.2 mmol) of the product from Step 2, 4.7 g (46 mmol) of isobutylboronic acid, 0.02 g of Pd$_2$(dba)$_3$ (0.23 mmol), 0.4 g (0.965 mmol) of 2-dicyclohexylphosphino-2',6'-dimethoxybiphenyl, 16.7 g (72.6 mmol) of K$_3$PO$_4$.H$_2$O and 300 mL of toluene were charged in a 500 mL round bottle flask. The reaction mixture was heated to reflux under nitrogen overnight with stirring. The reaction mixture was purified by silica gel chromatography with 10% ethyl acetate in hexanes as the eluent. 5.8 g (yield 87%) of product was obtained.

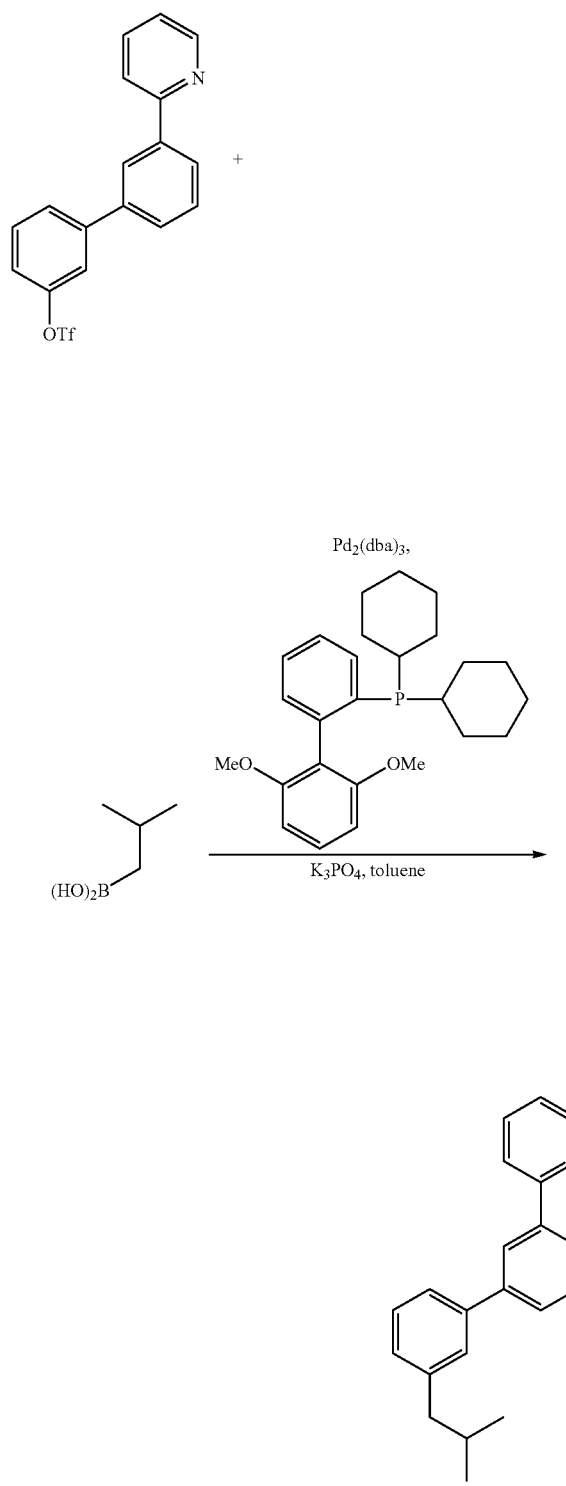

Step 4. 2.0 g (6.9 mmol) of the ligand from Step 3, 0.97 g (2.0 mmol) of Ir(acac)₃, and 25 mL of ethylene glycol were charged in a 100 mL round bottle flask. The reaction mixture was heated to reflux under nitrogen overnight. The reaction mixture was cooled down and 100 mL methanol was added. The solid was filtered, washed with methanol and dried. 1.3 g (62% yield) of product was obtained after silica column purification.

2.0 g (2.55 mmol) of the Ir(ppy)₃ boronic ester, prepared according to U.S. Ser. No. 11/951,879, 1.6 g (7.6 mmol) of 4-isobutylbromobenzene, 0.21 g (0.52 mmol) of 2-dicyclohexylphosphino-2',6'-dimethoxybiphenyl, 1.1 g (5.1 mmol) of potassium phosphate, 80 mL of toluene, and 8 mL of water were mixed in a 3-neck flask. The mixture was purged with nitrogen for 30 minutes. To the degassed mixture was added 0.12 g (0.127 mmol) of Pd₂(dba)₃. The reaction was refluxed under nitrogen atmosphere for overnight. After cooling to room temperature, the reaction mixture was filtered through a Celite bed. The yellow precipitate on the Celite bed was washed with dichloromethane. The solution was dried with magnesium sulfate. After solvent evaporation, the residue was purified by column using 1:1 hexanes and dichloromethane as eluent. 1.65 g of product was obtained.

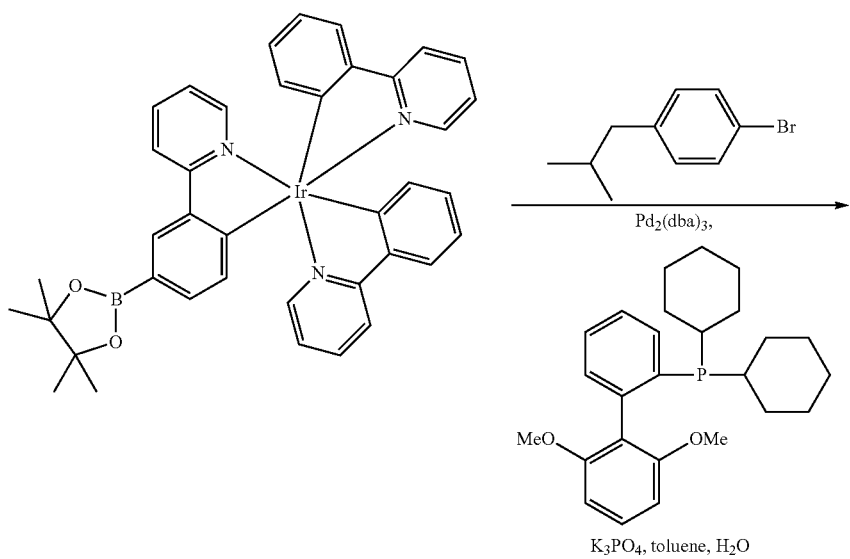

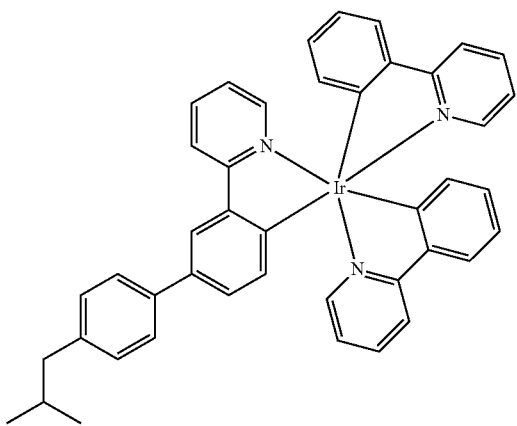

Compound 26

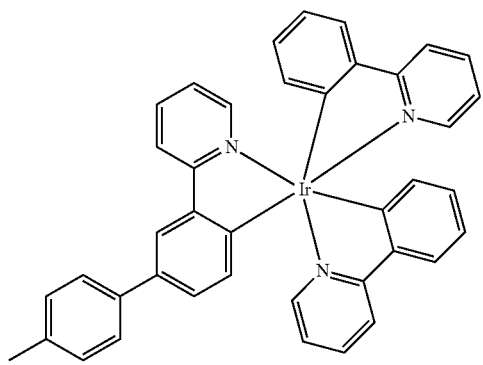

Compound 26

2.0 g (2.55 mmol) of the Ir(ppy)₃ boronic ester, 1.35 g (7.69 mmol) of 4-methylbromobenzene, 0.21 g (0.52 mmol) of 2-dicyclohexylphosphino-2',6'-dimethoxybiphenyl, 1.6 g (7.5 mmol) of potassium phosphate, 80 mL of toluene, and 8 mL of water were mixed in a 3-neck flask. The mixture was purged with nitrogen for 30 minutes. To the degassed mixture was added 0.12 g (0.127 mmol) of Pd₂(dba)₃. The reaction was refluxed under nitrogen atmosphere for overnight. After cooling to room temperature, the reaction mixture was filtered through a Celite bed. The yellow precipitate on the Celite bed was washed with dichloromethane. The solution was dried with magnesium sulfate. After solvent evaporation, the residue was purified by column using 1:1 hexanes and dichloromethane as eluent. 1.55 g (83% yield) of product was obtained.

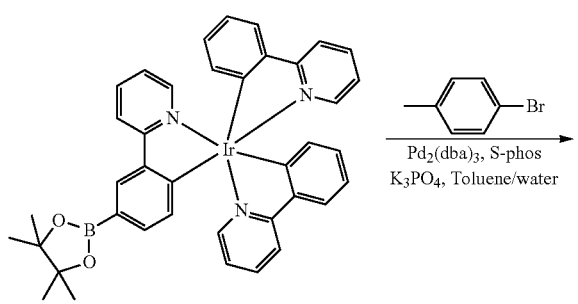

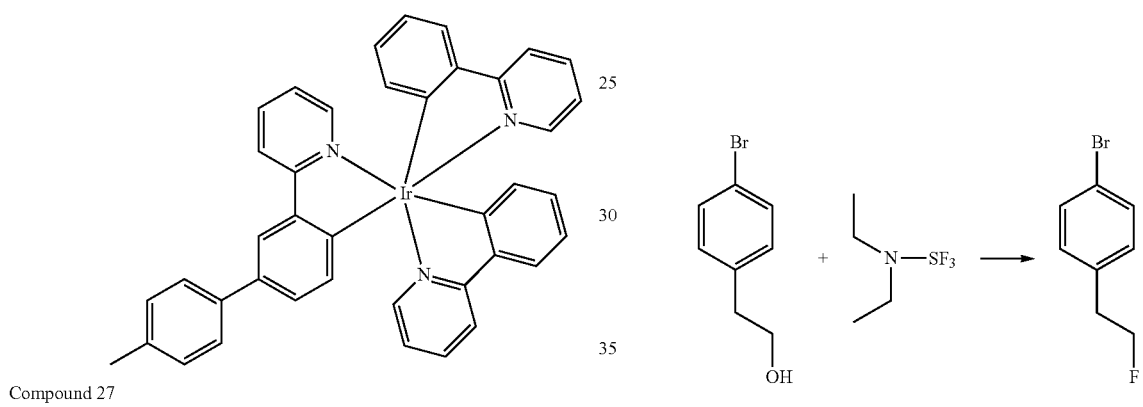

Compound 27

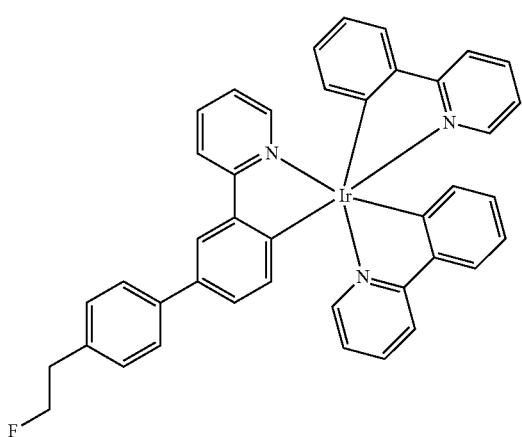

Compound 27

Step 1. 10.0 g (49.2 mmol) of 4-bromophenethyl alcohol, 9.17 g (54.1 mmol) of DAST were charged in a dry 250 mL flask with 150 mL anhydrous dichloromethane and the reaction mixture was stirred under nitrogen at room temperature for 20 hours. NaHCO$_3$ solution (40 g in 300 mL water) was slowly added to quench the reaction. After addition, it was further stirred for 2 hours until no CO$_2$ evolution. The organic extract was purified by silica gel column to yield 9 g (91% yield) of product.

Step 2. 2.0 g (2.55 mmol) of the Ir(ppy)$_3$ boronic ester, 1.0 g (5.0 mmol) of the Step 1 product, 0.21 g (0.52 mmol) of 2-dicyclohexylphosphino-2',6'-dimethoxybiphenyl, 1.6 g (7.5 mmol) of potassium phosphate, 80 mL of toluene, and 8 mL of water were mixed in a 3-neck flask. The mixture was purged with nitrogen for 30 minutes. To the degassed mixture was added 0.12 g (0.127 mmol) of Pd$_2$(dba). The reaction was refluxed under nitrogen atmosphere for overnight. After cooling to room temperature, the reaction mixture was filtered through a Celite bed. The yellow precipitate on the Celite bed was washed with dichloromethane. The solution was dried with magnesium sulfate. After solvent evaporation, the residue was purified by column using 1:1 hexanes and dichloromethane as eluent to yield 1.65 g (85% yield) of product was obtained.

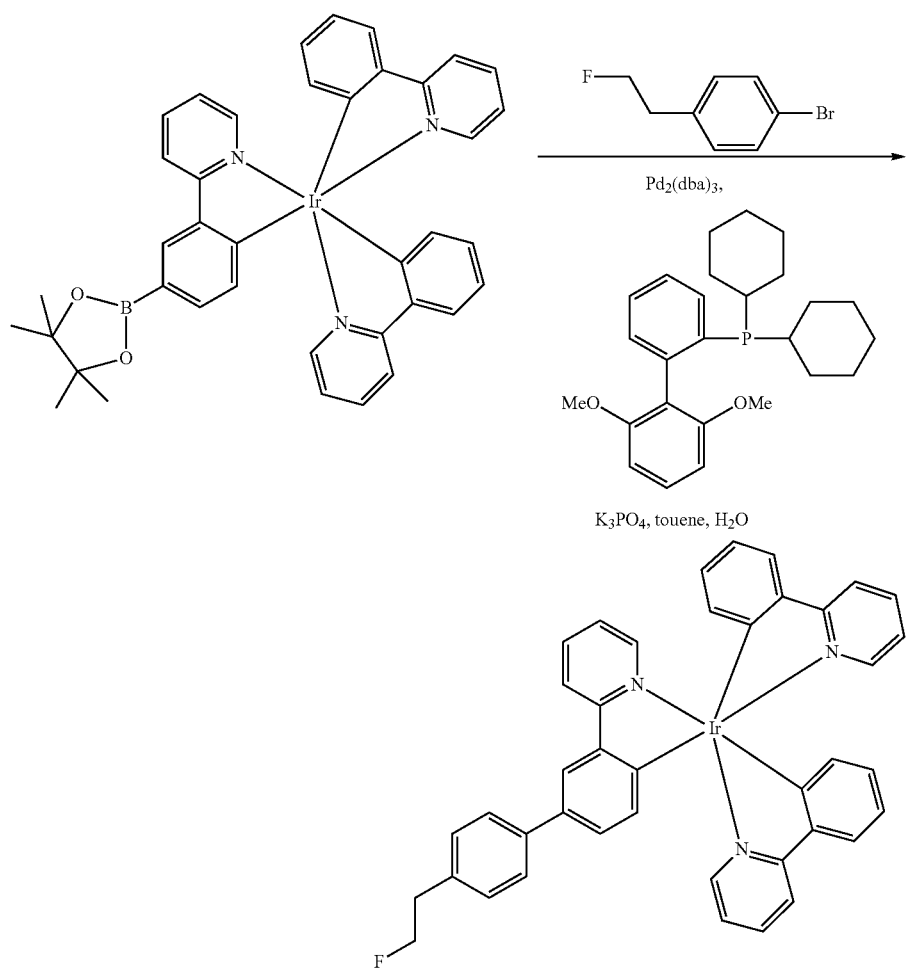

Compound 28

Compound 28

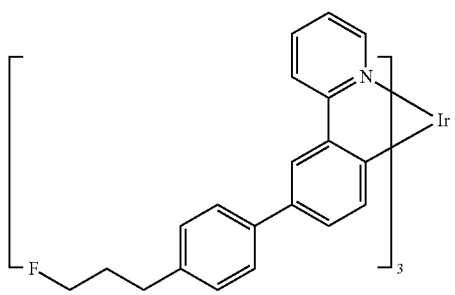

Step 1. 9.5 mL of BuLi (23.75 mmol; 2.5 M BuLi in hexanes) was added slowly to 4.0 g (19.7 mmol) of 4-(2-fluoroethyl)bromobenzene 100 mL of anhydrous THF at −78° C. The mixture was stirred for 1 hour at −78° C., then 2.6 mL (23.7 mmol) of B(OMe)$_3$ in 10 mL of anhydrous THF was added at −78° C. The reaction was warmed to room temperature and stirred for overnight. 60 mL HCl (1 M) was added and the mixture was stirred for 3 hours. Ethyl acetate was added to the reaction solution to extract the organic phase. The organic phase was combined and evaporated. A white solid was obtained which was washed by hexanes and dried. The boronic acid obtained was used for next step without further purification.

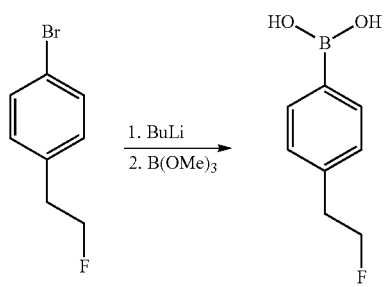 [SMILES: FCCc1ccc(Br)cc1 ; OB(O)c1ccc(CCF)cc1]

Step 2. 2.5 g (14.8 mmol) of the boronic acid from Step 1, 3.0 g (13.5 mmol) of 2-(3-bromophenyl)pyridine, 0.48 g (0.415 mmol) of Pd(PPh$_3$)$_4$, 5.6 g (40.57 mmol) K$_2$CO$_3$, 50 mL of DME and 50 mL of water were charged in a 200 flask. The reaction mixture was heated to reflux under nitrogen for overnight. The organic extract was purified by silica gel column. 3.2 g (86% yield) of product was obtained.

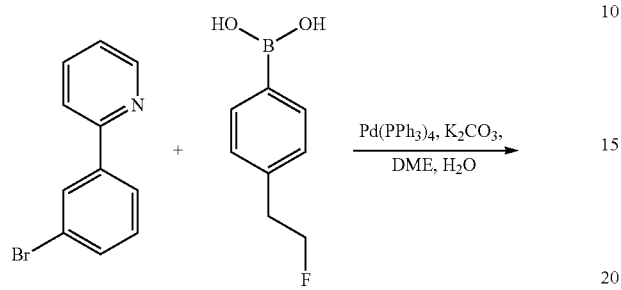

Step 3. 3.0 g (10.8 mmol) of the ligand from Step 2, 1.3 g (2.7 mmol) of Ir(acac)$_3$ and 50 mL of ethylene glycol were added in a 100 mL flask and heated to reflux under nitrogen for overnight. The organic extract was purified by silica gel column. 1.65 g (60% yield) of product was obtained.

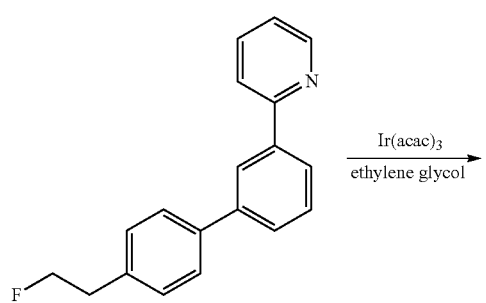

Compound 29

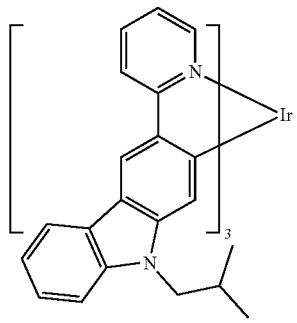

Step 1. Carbazole (10 g, 60 mmol), 1-bromo-2-methyl-propane (16.4 g, 120 mmol), KOH (8.4 g, 150 mmol), 18-crown-6 (160 mg, 0.6 mmol) and DMF 50 mL were mixed and stirred at room temperature for two days. The mixture was diluted with 400 mL water and extracted with dichloromethane for 3 times. The combined organic layers were dried with MgSO$_4$ and evaporated under reduced pressure. The crude product was purified by silica column with up to 5% CH$_2$Cl$_2$ in hexanes to provide 12 g of product (66% yield).

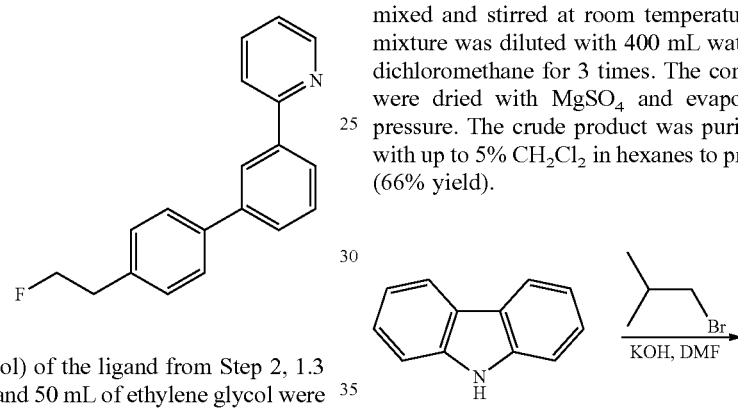

Step 2. 9-isobutyl-9H-carbazole (12 g, 53.7 mmol), N-bromosuccinimide (9.6 g, 53.7 mmol) and 300 mL of DMF were mixed and stirred at room temperature for two days. The solvent was evaporated under reduced pressure. The mixture was redissolved in dichloromethane and washed with water. The organic layer was collected and dried with MgSO$_4$ to provide 16.7 g of product (100% yield).

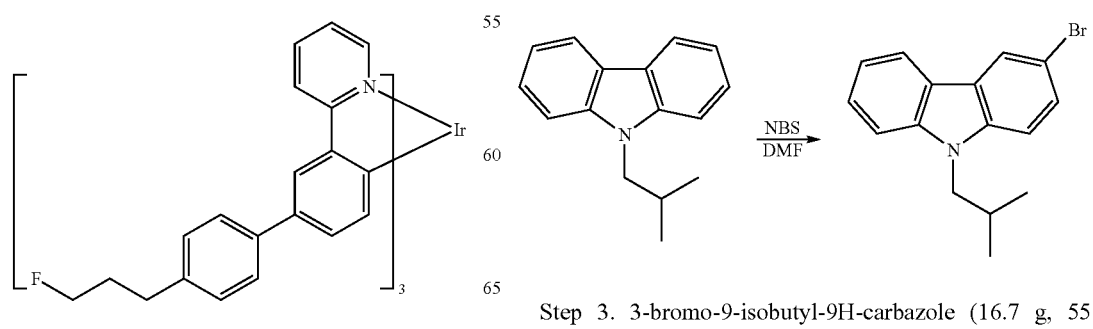

Step 3. 3-bromo-9-isobutyl-9H-carbazole (16.7 g, 55 mmol), pinacolatodiboron (28 g, 110 mmol), potassium acetate (16 g, 165 mmol) and 400 mL of anhydrous dioxane were mixed to and purged with nitrogen for 20 minutes. Then Pd(dppf)$_2$Cl$_2$ was added and the system was purged with nitrogen for another 15 minutes. After heated at 90° C. for overnight, the solvent was evaporated. The crude product was purified by silica column with up to 10% ethyl acetate in hexanes to afford 3 g of pure product (16% yield).

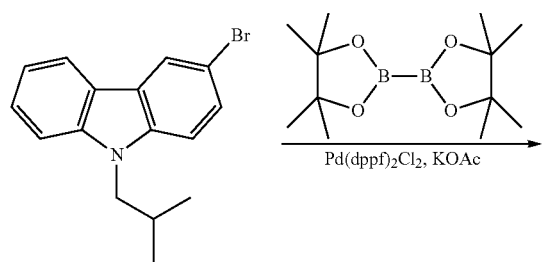

Step 4. 9-isobutyl-3-(4,4,5,5-tetramethyl-1,3,2-dioxaborolan-2-yl)-9H-carbazole (3.1 g, 8.9 mmol), bromopyridine (2.8 g, 17.8 mmol), potassium carbonate (3.7 g, 26.6 mmol), triphenylphosphine (0.28 g, 1.1 mmol), 60 mL dimethoxyethane and 20 mL water were mixed in a 3-neck flask. The system was purged with nitrogen for 30 minutes. Then palladium acetate (60 mg, 0.27 mmol) was added and the mixture was purged with nitrogen for another 15 minutes. After being refluxed overnight, the organic layer was collected and the solvent was evaporated. The mixture was purified by silica column with up to 10% ethyl acetate in hexanes to give 2.1 g of a white solid (79% yield).

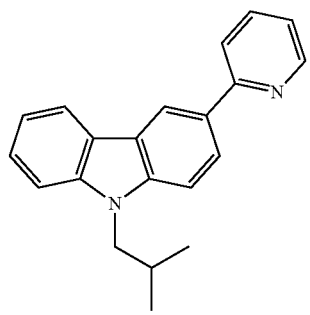

Step 5. 3-phenyl-9-isobutyl-9H-carbazole (2.1 g, 7 mmol), Ir(acac)$_3$ (0.86 g, 1.7 mmol) and 20 mL ethylene glycol were mixed. The mixture was vacuumed and refilled with nitrogen 3 times and then heated at 220° C. for two days. After the mixture was cooled down to room temperature, methanol was added to precipitate the complex. The residue was collected and washed by methanol. The crude product was purified by silica column with 1:1 CH$_2$Cl$_2$ and hexanes to give 1.2 g of a yellow solid (65% yield). The product was further purified by high vacuum sublimation at 290° C.

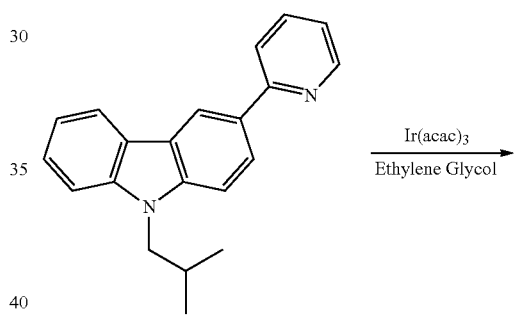

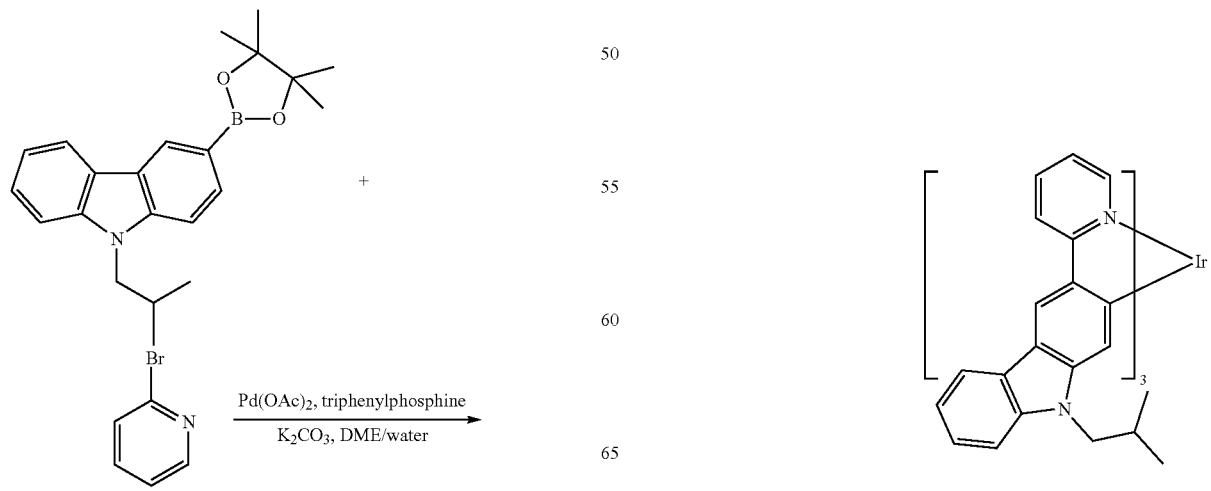

Compound 30

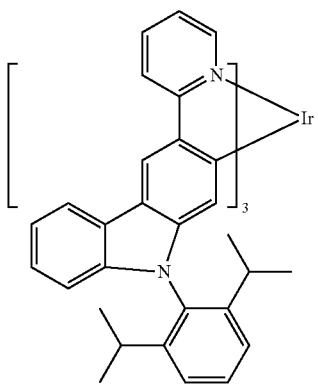
Compound 30

Step 1. 5.3 g (30 mmol) of 2,6-diisopropylaniline, 9.36 g (30 mmol) of 2,2'-dibromobiphenyl, 0.99 g (2.4 mmol) of 2-dicyclohexylphosphino-2',6'-dimethoxybiphenyl, 8.8 g (90 mmol) of sodium t-butoxide, and 0.55 g (0.6 mmol) of $Pd_2(dba)_3$ were mixed in 100 mL of xylene. The mixture was refluxed under nitrogen overnight. After cooled to room temperature, the reaction mixture was filtered through a Celite bed. The product was columned with hexanes. 5.8 g of product was obtained after column (59% yield).

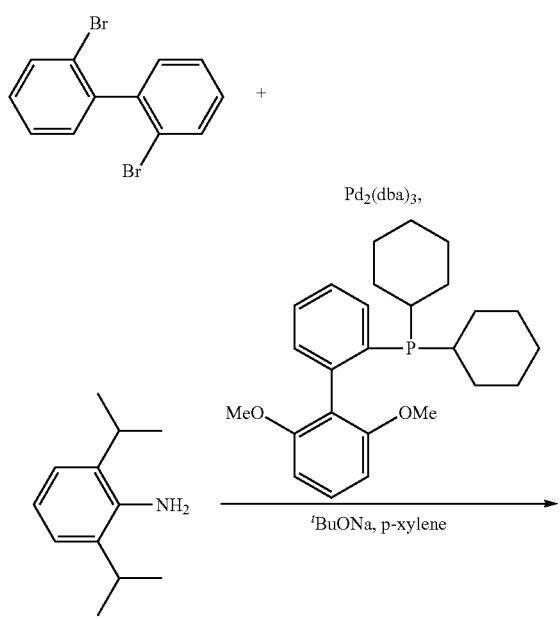

Step 2. 5.7 g (17 mmol) of 9-(2,6-diisopropylphenyl)-9H-carbazole was dissolved in 100 mL of DMF. To the solution was added 3.1 g (17 mmol) of NBS in small portions. The reaction was allowed to react for 2 hours. Water was added to precipitate the product. The product was the dissolved with dichloromethane, washed with water, and dried with magnesium sulfate. After solvent evaporation, 6.78 g of product was obtained, which contains about 72% of product from HPLC. The product was used directly for the next step without further purification.

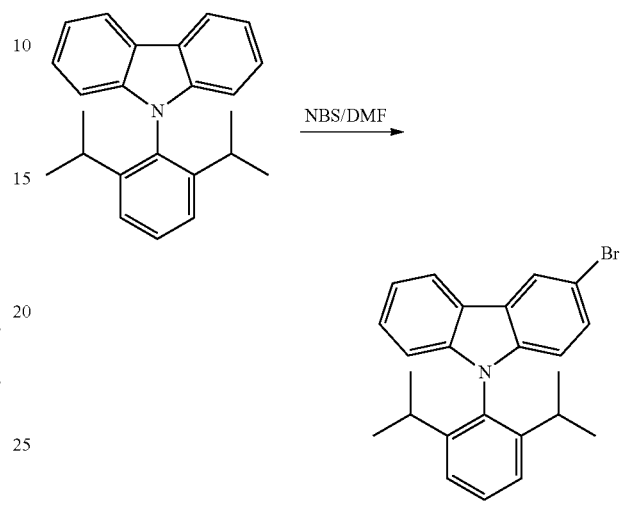

Step 3. 6.78 g of 3-bromo-9-(2,6-diisopropylphenyl)-9H-carbazole, 5.8 g (23 mmol) of pinacolatodiboron, 4.9 g (50 mmol) of potassium acetate, 100 mL of DMSO were mixed in a 3-neck flask. The system was purged with nitrogen for 30 minutes. To the mixture was added 0.4 g (0.5 mmol) of $Pd(dppf)_2Cl_2$. The reaction was heated to 80° C. for 15 hours. The reaction was monitored by TLC. After the reaction was complete, the product was precipitated with 300 mL of water. The solid was columned with 1:5 dichloromethane and hexanes. 4.3 g of product was obtained (57% yield).

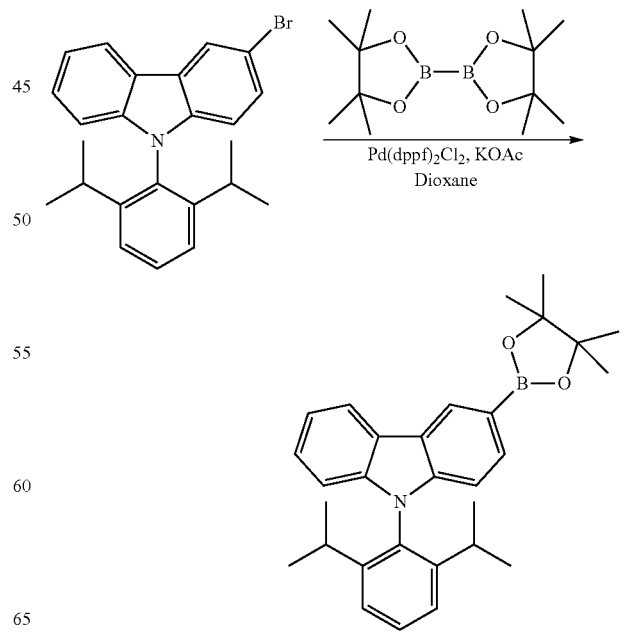

4.3 g (9.5 mmol) of the boronic ester, 1.8 g (11.4 mmol) of 2-bromopyridine, 6.4 g (28.5 mmol) of potassium phosphate, 0.16 g (0.38 mmol) of 2-dicyclohexylphosphino-2',6'-dimethoxybiphenyl, 100 mL of toluene and 10 mL of water were mixed in a 3-neck flask. The system was purged with nitrogen for 30 minutes. 0.09 g (0.09 mmol) of $Pd_2(dba)_3$ was added and the mixture was heated to reflux overnight. The product was column chromatography with 5% ethyl acetate in hexanes. 1.0 g of product was obtained after column.

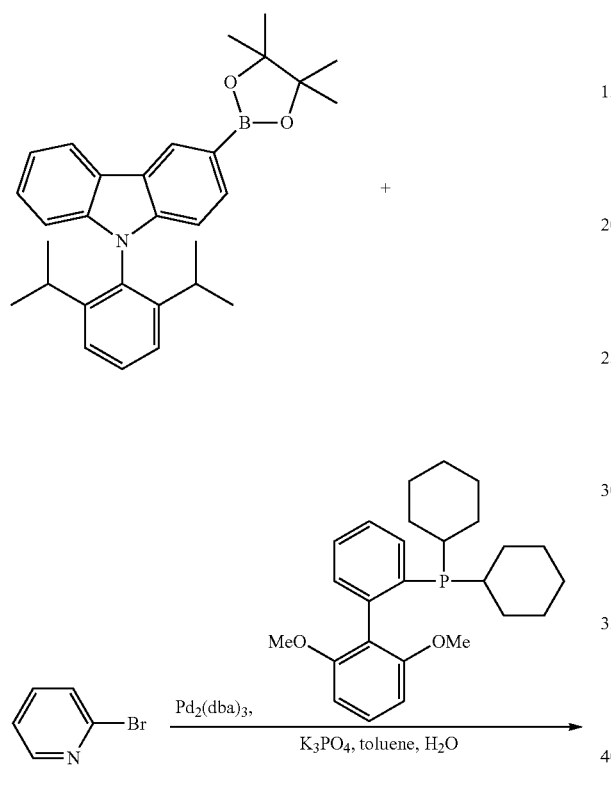

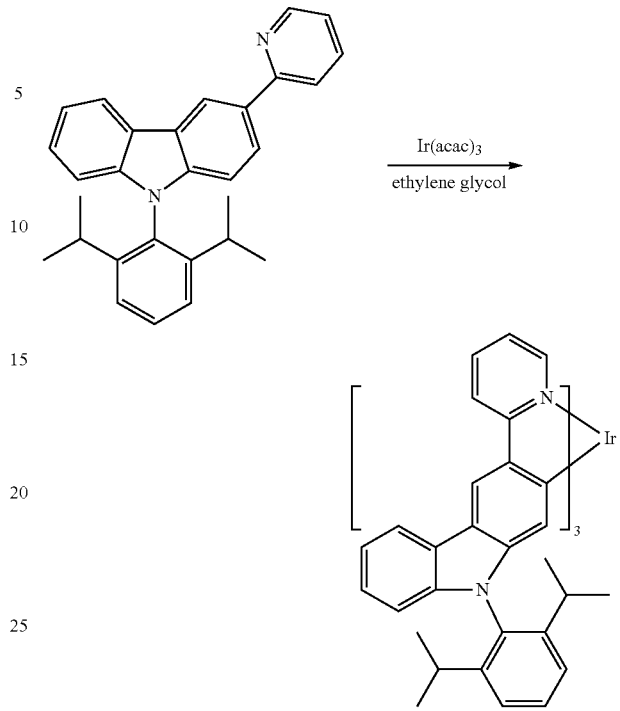

Compound 31

Compound 31

0.9 g (2.2 mmol) of 9-(2,6-diisopropylphenyl)-3-(pyridin-2-yl)-9H-carbazole and 0.22 g (0.45 mmol) of $Ir(acac)_3$ were heated to reflux in 20 mL of ethylene glycol for 48 hours. After cooled to room temperature, 100 mL of methanol was added. The precipitate was collected by filtration. The solid was purified by column using 1:1 dichloromethane and hexanes as eluent. 0.07 g product was obtained after column purification. The product was further purified by high vacuum sublimation at 350° C.

Step 1. 4.5 g (21.9 mmol) of 5-bromo-2-fluoro-m-xylene, 6.2 g (24.1 mmol) of pinacolatodiborane. 0.54 g (0.66 mmol) of $Pd(dppf)_2Cl_2 \cdot CH_2Cl_2$, 6.4 g (65.7 mmol) of KOAc, and 100 mL of DMSO were charged in a 200 mL flask. The reaction mixture was heated at 80° C. under nitrogen for overnight. The organic extract was purified by silica gel column with 10% ethyl acetate in hexanes as the eluent. 4.3 g (79.6% yield) of product was obtained.

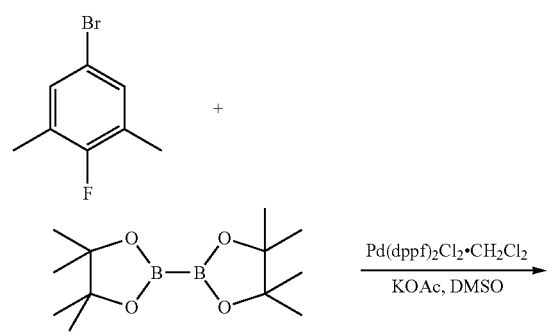

-continued

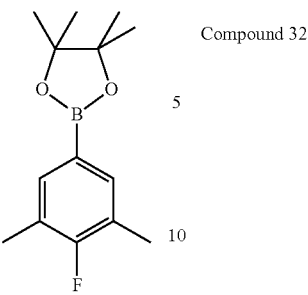

Compound 32

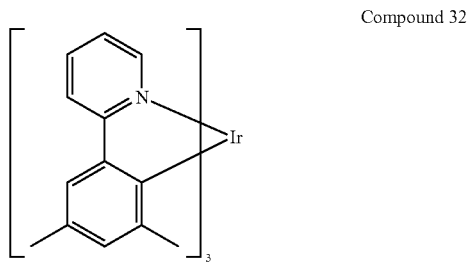

Compound 32

Step 2. 4.0 g (16 mmol) of the Step 1 product, 2.3 g (14.5 mmol) of bromopyridine, 0.51 g (0.44 mmol) of Pd(PPh$_3$)$_4$ and 6 g (43.3 mmol) K$_2$CO$_3$, 50 mL of DME and 50 mL of water were added in a 250 mL flask. The reaction was refluxed under nitrogen for 5 hours. The reaction was then worked up with silica gel column with 4% ethyl acetate in hexanes as the eluent. 2.8 g (96% yield) of product was obtained.

Step 1. 12.6 g (80 mmol) of 2-bromopyridine, 12 g (80 mmol) of 3,5-phenylboronic acid, 0.18 g (0.8 mmol) of palladium acetate, 0.84 g (3.2 mmol) of triphenylphosphine and 33 g (240 mmol) of potassium carbonate, 80 mL of dimethoxyethane and 50 mL of water was purged with nitrogen and heated to reflux for 12 hours. Upon cooling, the organic layer was separated, washed with water, and dried with MgSO$_4$. The product was separated by column chromatography using 5% ethyl acetate in hexanes as the eluent.

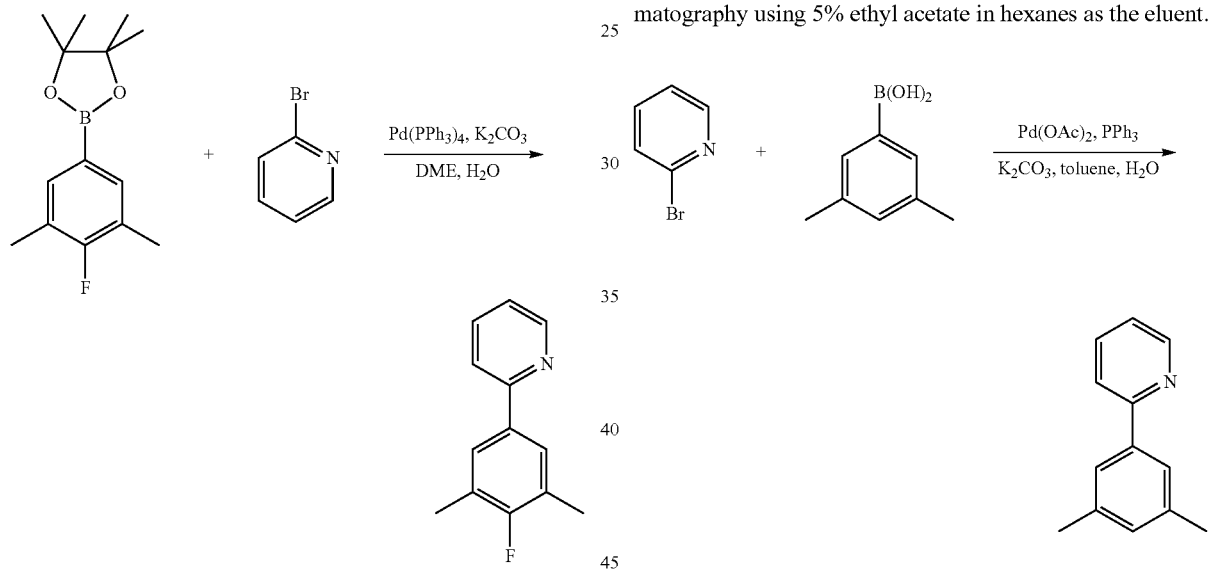

Step 3. 2.1 g (10.2 mmol) of the Step 2 product and 1.27 g (2.6 mmol) of Ir(acac)$_3$ were charged in a Schlenk tube and heated to 245° C. for 28 hours under nitrogen. The precipitate was collected and purified by silica gel column with 25% dichloromethane in hexanes as the eluent. 0.25 g (11% yield) of product was obtained.

Step 2. A mixture of 1 g (5.45 mmol) of 2-(3,5-dimethylphenyl)pyridine and 0.53 g (1.09 mmol) of Ir(acac)$_3$ was heated with a sand bath to an external temperature of 290° C. for 3 hours. The mixture was cooled and dissolved in dichloromethane. The product was dry-packed on Celite and separated by column chromatography using hexanes/dichloromethane as the eluent (40% dichloromethane). 0.1 g of product was collected.

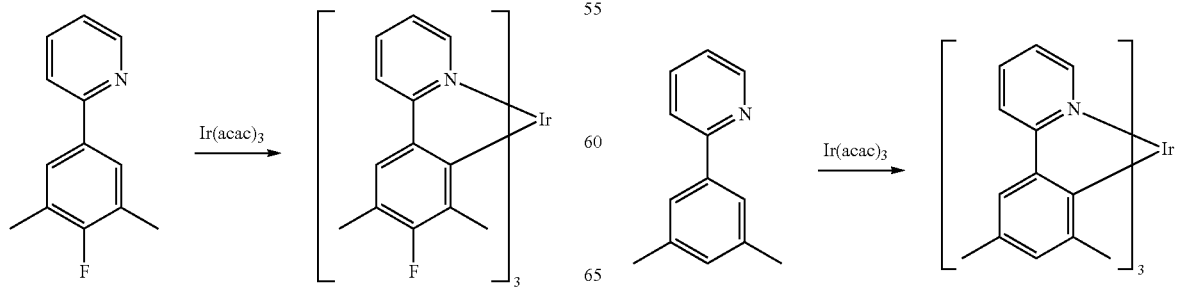

Alternative method for Compound 32

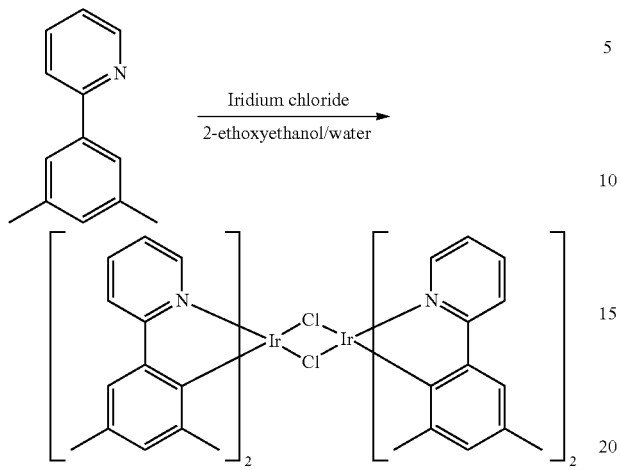

Step 1. 6.6 g (36 mmol) of 2-(3,5-dimethylphenyl)pyridine and 4.23 g (12 mmol) of iridium chloride, 90 ml of 2-ethoxyethanol, and 30 mL of water were mixed and heated to reflux overnight under nitrogen. After being cooled to room temperature, the solid was collected by filtration, and washed thoroughly with methanol and hexanes. The solid was dried and used for the next step without further purification. 6 g of desired product was obtained (84% yield).

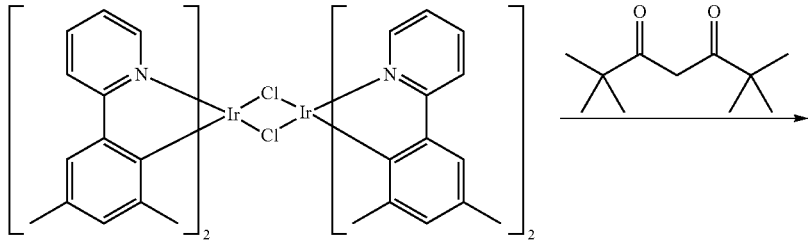

Step 2. 6.0 g (5 mmol) of the dimer, 9.2 g (50 mmol) of 2,2,6,6-tetramethylheptane-3,5-dione, 2.7 g (25 mmol) of sodium carbonate, and 100 mL of 2-ethoxyethanol were mixed in a flask and heated to reflux under nitrogen for 4 hours. After being cooled to room temperature, the mixture was filtered through a Celite bed. The solid was thoroughly washed with methanol. The solid on top of the Celite bed was dissolved with dichloromethane. The solution was then run through a triethylamine treated silica gel plug. After solvent evaporation, 5.9 g of desired product was obtained (80% yield).

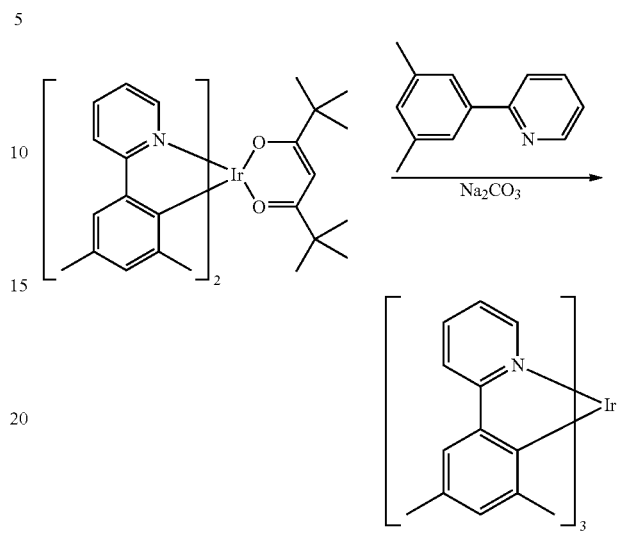

Step 3. 2.95 g (4 mmol) of the 'Buacac complex, 7.3 g (40 mmol) of 2-(3,5-dimethylphenyl)pyridine, and 2.1 g (20 mmol) of sodium carbonate was mixed and degassed carefully. The mixture was heated to 270° C. for 24 hours then

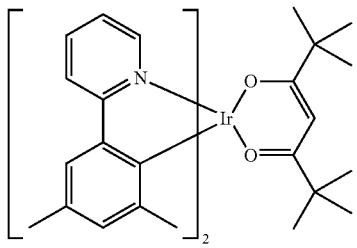

290° C. for 6 hours. The reaction was cooled to room temperature. 30 mL of dichloromethane was added. The mixture was filtered through Celite. The solvent was evaporated and 300 mL of hexanes was added to the residue. The mixture was stirred overnight. The solid was collected by filtration. The unreacted starting materials were gone. The solid was further purified by silica gel columns using 3:1 hexanes and dichloromethane as solvent. 0.7 g of material was collected after purification. The complex was further purified by high vacuum sublimation. 0.4 g of product was obtained.

Compound 33

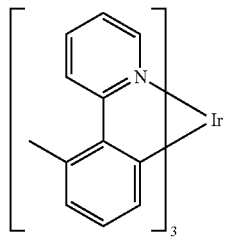

Compound 33

Step 1. A mixture of 8.1 g (51.5 mmol) of 2-bromopyridine, 7 g (51.5 mmol) o-tolylboronic acid, 0.47 g (0.51 mmol) of $Pd_2(dba)_3$. 0.84 g (2.06 mmol) of 2-dicyclohexylphosphino-2',6'-dimethoxybiphenyl and 32 g (154.5 mmol) of potassium phosphate tribasic, 100 mL of toluene and 30 mL of water was purged with nitrogen. The solution was heated to reflux for 12 hours. Upon cooling, the organic layer was separated, and dried with $MgSO_4$. The product was separated by column chromatography using hexanes/ethyl acetate (5% ethyl acetate) as the eluent. The solvent was removed by rotary evaporation, and the product was dried under vacuum resulting in 6 g (35.5 mmol) of 2-(o-tolyl)pyridine.

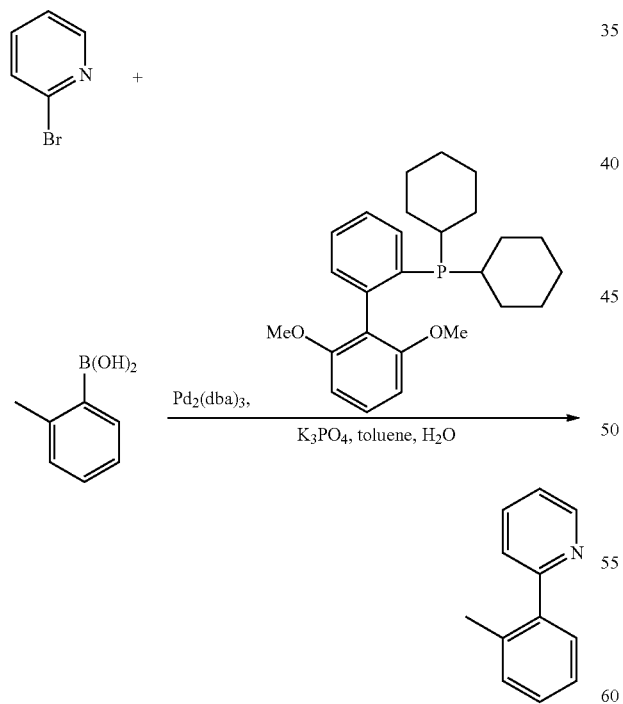

Step 2. A mixture of 1.5 g (8.8 mmol) of 2-(o-tolyl)pyridine and 0.7 g (1.45 mmol) $Ir(acac)_3$ was heated with a sand bath to an external temperature of 290° C. for 12 hours. The reaction was cooled and dissolved in dichloromethane. The product is dry-packed on Celite and separated by column chromatography using hexanes/dichloromethane as the eluent (40% dichloromethane). 0.75 g (1.07 mmol) of the product was collected.

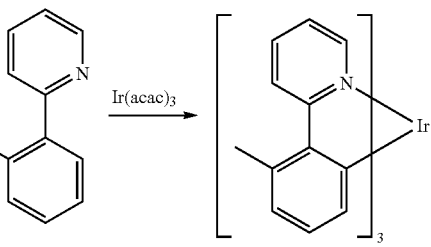

Compound 34

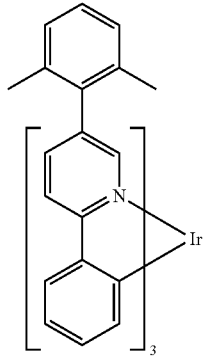

Compound 34

Step 1. 3.0 g (12.8 mmol) of 5-bromo-2-phenylpyridine, 2.3 g (15.4 mmol) of 2,6-dimethylphenylboronic acid, 8.6 g (38.4 mmol) of potassium phosphate, 0.21 g (0.52 mmol) of 2-dicyclohexylphosphino-2',6'-dimethoxybiphenyl, 100 mL of toluene and 10 mL of water were mixed in a 3-neck flask. The system was purged with nitrogen for 30 minutes. 0.12 g (0.13 mmol) of $Pd_2(dba)_3$ was added and the mixture was heated to reflux overnight. After cooled to room temperature, the reaction mixture was filtered through a Celite bed. The product was column chromatographed with 5% ethyl acetate in hexanes. 3.0 g of product was obtained after column (90% yield).

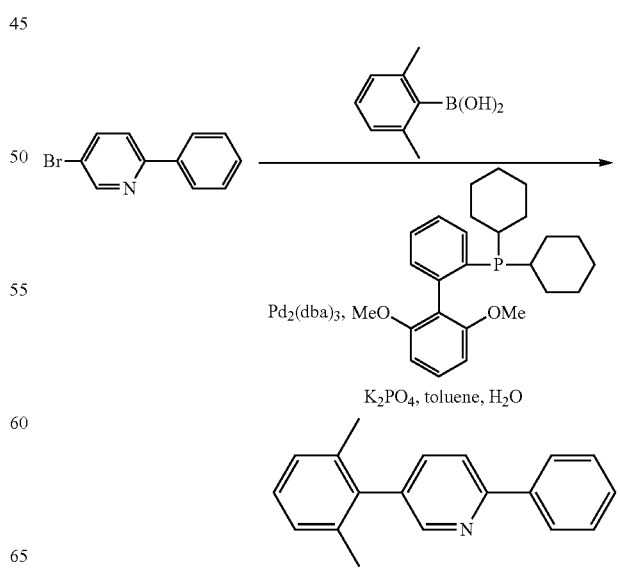

3.0 g (11.6 mmol) of 5-(2,6-dimethylphenyl)-2-phenylpyridine and 1.1 g (2.3 mmol) of Ir(acac)₃ were heated to reflux in 30 mL of ethylene glycol for 42 hours. After cooled to room temperature, 100 mL of methanol was added. The precipitate was collected by filtration. The solid was purified by column using 1:1 dichloromethane and hexanes as the eluent. 1.0 g product was obtained. The product was further purified by high vacuum sublimation at 270° C.

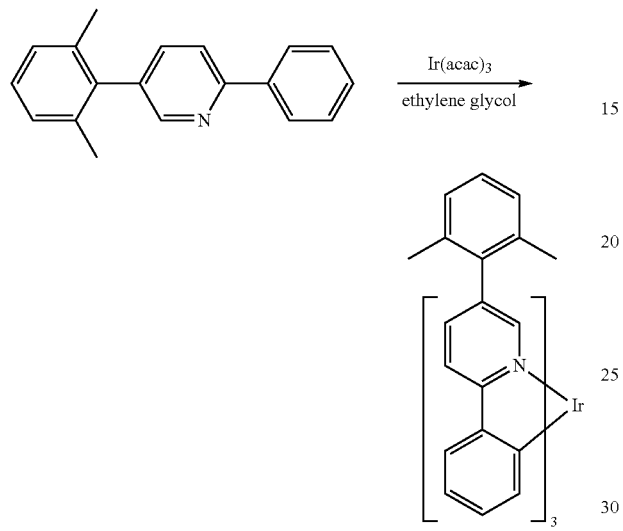

Compound 35

Synthesis of Compound 35: 0.52 g (0.64 mmol) of the above mono boronic ester, 0.3 g (1.93 mmol) phenylboronic acid, 0.006 g (0.0064 mmol) tris(dibenzylideneacetone)dipalladium (0) [Pd₂(dba)₃], 0.10 g (0.025 mmol) 2-dicyclohexylphosphino-2',6'-dimethoxybiphenyl (SPhos), and 0.4 g (1.92 mmol) potassium phosphate tribasic (K₃PO₄) were weighed into a flask. 30 mL toluene and 10 mL water were used as solvent and the solution was purged with nitrogen. The solution was heated to reflux for twelve hours. Upon cooling, the organic layer was separated, and dried with MgSO₄. The product was separated by column chromatography using hexanes/dichloromethane as eluent. The solvent was removed by rotary evaporation, and the product dried under vacuum. The product was further purified by high vacuum sublimation at 250° C. resulting in 0.3 g (0.39 mmol).

Compound 35

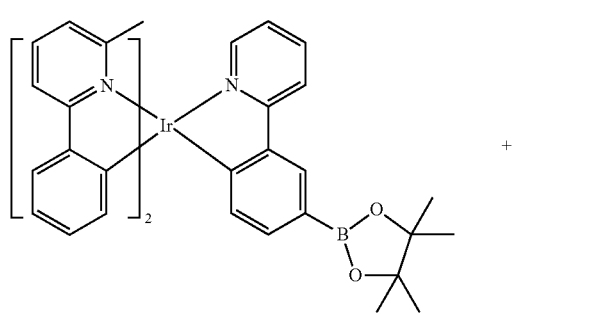

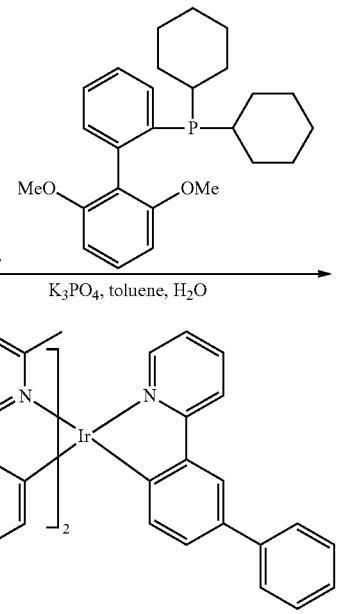

Compound 36

Synthesis of Compound 36:

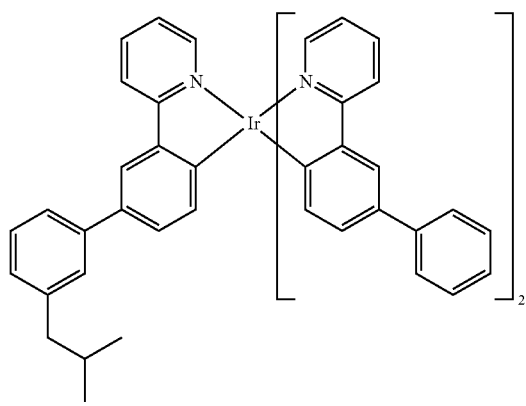

A mixture was prepared of 2-bromopyridine (40 g, 253 mmol), 3-bromophenylboronic acid (61.0 g, 303.8 mmol), triphenylphosphine (6.64 g, 25.3 mmol), potassium carbonate (87.4 g, 632.5 mmol) in of 300 mL dimethoxyethane, and 200 mL of water. Nitrogen was bubbled directly into the mixture for 20 minutes, then palladium acetate was added (2.84 g, 12.65 mmol). The reaction mixture was heated to reflux under nitrogen. At the end of the day, a trace of 2-bromopyridinme was detected by TLC. Thus an additional 10 grams of 2-bromophenylboronic acid was added and reaction continued to reflux overnight. The reaction mixture was cooled and water was added along with ethyl acetate. The layers were separated and the aqueous layer was extracted with ethyl acetate. The organic layers were dried over magnesium sulfate, filtered, and evaporated to a brown oil. The oil was purified by column chromatography eluting with 0 to 40% ethyl acetate/hexanes followed by distillation under vacuum. Obtained 45.1 g of desired product (52% yield), as confirmed by GC-MS.

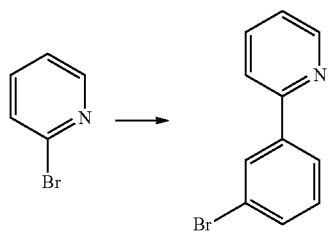 [SMILES: Brc1ccccn1 ; Brc1cccc(-c2ccccn2)c1]

A mixture was prepared of 2-(3-bromophenyl)pyridine (12.2 g, 52.10 mmol), 3-(4,4,5,5-tetramethyl-1,3,2-dioxaborolan-2-yl)phenol (13.76 g, 62.53 mmol), 2-dicyclohexylphosphino-2',6'-dimethoxybiphenyl (856 mg, 2.08 mmol), potassium phosphate tribasic monohydrate (36 g, 156.3 mmol) in 180 mL of dioxane, and 18 mL of water. Nitrogen was bubbled directly into the mixture for 20 minutes, then tris(dibenzylideneacetone)dipalladium(0) was added (477 mg, 0.52 mmol). The reaction mixture was heated at 100° C. for 3 hours under nitrogen, then allowed to cool to room temperature overnight. Water was added to the reaction mixture and the mixture was extracted three times with ethyl acetate. The organic extracts were dried over magnesium sulfate, filtered and evaporated to a residue. The residue was purified by column chromatography eluting with 20 and 40% ethyl acetate/hexanes. Obtained 12.5 g of a yellow oil (97% yield), as confirmed by GC-MS.

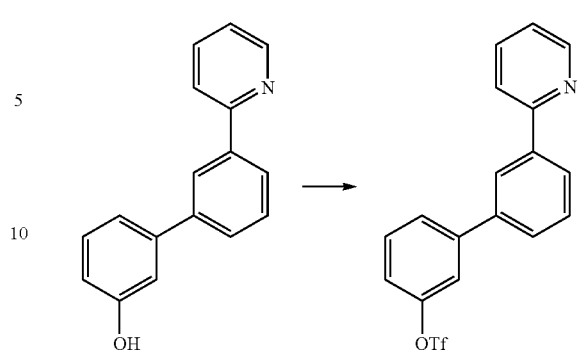

8.8 g (23.2 mmol) 3'-(pyridin-2-yl)biphenyl-3-yl trifluoromethanesulfonate, 4.7 g (46 mmol) isobutaneboronic acid, 211 mg $Pd_2(dba)_3$ (0.23 mmol), 396 mg (0.965 mmol) S-Phos, 16.7 gram (72.6 mmol) $K_3PO_4H_2O$, and 300 ml toluene were charged in a 500 ml round bottle flask. The reaction mixture was heated up to reflux under nitrogen overnight with stirring. The reaction mixture was purified by silica gel chromatography with 10% (v/v) ethyl acetate in hexane as elute. ~5.8 gram solid (yield 87%) product was obtained, as confirmed by GC-MS.

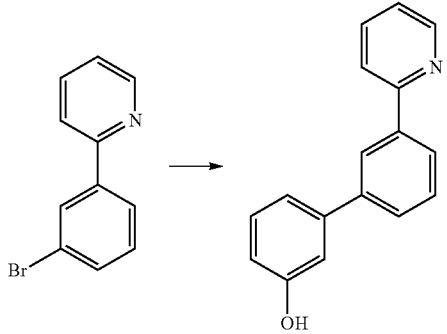 [SMILES: Brc1cccc(-c2ccccn2)c1 ; Oc1cccc(-c2cccc(-c3ccccn3)c2)c1]

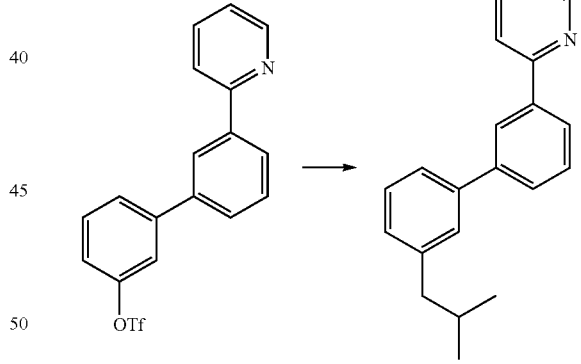

12.5 gram (50.6 mmol) 3'-(pyridin-2-yl)biphenyl-3-ol, 12 ml pyridine, and ~200 ml methylene chloride were mixed in a 500 ml round bottle flask at 0° C. To the mixture, 14.3 gram (101.2 mmol) trifluoroacetic anhydride was added and stirred for 30 min at 0° C., then stirred at room temperature for 1 hour. The reaction mixture was washed with water several times. ~19 gram (~100% yield) triflate was obtained after evaporation of solvent, as confirmed by GC-MS.

3.4 gram (11.8 mmol) 2-(3'-isobutylbiphenyl-3-yl)pyridine, 2.0 gram (5.3 mmol) $IrCl_3.3H_2O$, and 150 ml solvent mixture (2 ethoxyethanol/water: 3:1) were charged in a 250 ml round bottle flask. The reaction mixture was heated up to reflux under nitrogen overnight. The reaction mixture was cooled down and added ~100 ml methanol, then filtered. The solid was washed with methanol and dried. About 3.85 gram of chloro-bridged iridium dimer was obtained and used for next step without further purification.

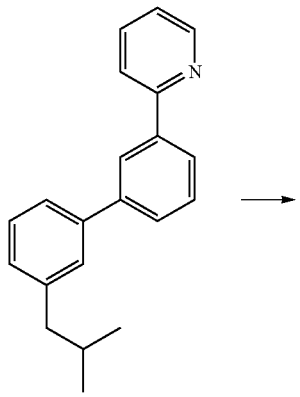

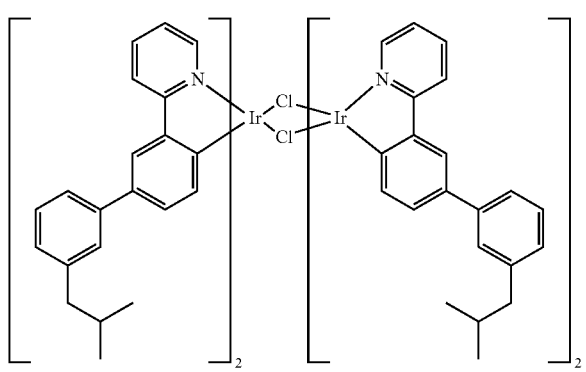

A mixture was prepared of 2-bromopyridine (8.66 g, 54.8 mmol), 3-methoxy phenylboronic acid (10 g, 65.8 mmol), triphenylphosphine (1.44 g, 5.48 mmol), potassium carbonate (18.9 g, 137 mmol) in 100 mL dimethoxyethane and 66 mL of water. Nitrogen was bubbled directly into the mixture for 20 minutes, then palladium acetate was added (0.61 g, 2.74 mmol). The reaction mixture was heated to reflux overnight under nitrogen. The reaction mixture was cooled and water was added along with ethyl acetate. The layers were separated and the aqueous layer was extracted with ethyl acetate. The organic layers were dried over magnesium sulfate, filtered, and evaporated to residue. The residue was purified by column chromatography eluting with 0 to 20% ethyl acetate/hexanes. Obtained 9.7 g of a clear oil (96% yield), as confirmed by GC-MS.

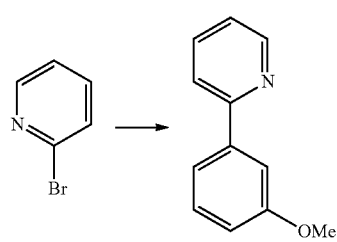 [SMILES: Brc1ccccn1 ; COc1cccc(-c2ccccn2)c1]

A mixture of 2-(3-methoxyphenyl)pyridine (9.7 g, 52.37 mmol) and pyridine hydrochloride (72.6 g, 628.44 mmol) was prepared. The mixture was heated to 220° C. The reaction was done in 2 hours. Water was added to the cooled mixture and then extracted with dichloromethane twice. The organic extracts were dried over magnesium sulfate, filtered, and evaporated to a residue. The residue was purified by column chromatography eluting with 0, 1, and 2% methanol/dichloromethane, followed by Kugelrohr distillation and recrystallization from 2:1 hexane/ethyl acetate. Obtained 5 g of a white solid (56% yield), as confirmed by GC-MS.

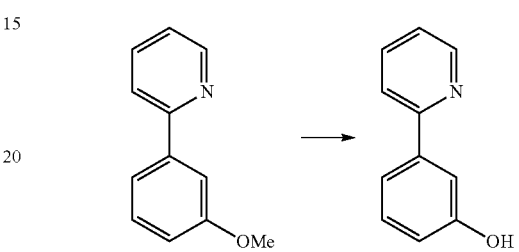

A solution was prepared of 3-(pyridin-2-yl)phenol (5 g, 29.21 mmol) in 100 mL of dichloromethane. To this solution was added pyridine (4.7 mL, 58.42 mmol) and the solution was cooled in an ice-salt bath. To this solution was added a solution of trifluoromethanesulfonic anhydride (9.8 mL, 58.42 mmol) in 20 mL of dichloromethane drop wise. The reaction was allowed to warm slowly and was complete after 2 hours. Water and dichloromethane was added and the layers were separated. The aqueous layer was extracted with dichloromethane. The organic layers were dried over magnesium sulfate, filtered and evaporated to a residue. The residue was purified by column chromatography eluting with 5, 10, and 15% ethyl acetate/hexanes. Obtained 8 g of a clear liquid (90% yield), as confirmed by GC-MS.

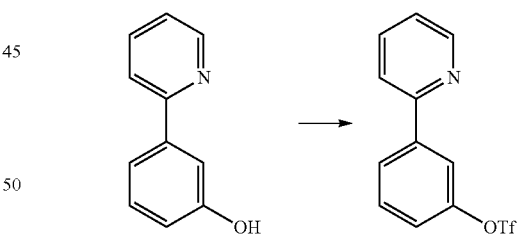

3.85 gram (2.41 mmol) the above chloro-bridged iridium dimer, 1.42 gram (5.3 mmol) silver triflate $AgOSOCF_3$, 2.93 gram (9.64 mmol) 3-(pyridin-2-yl)phenyl trifluoromethane sulfonate and ~300 ml 2-ethoxyethanol were mixed in a 500 mL round bottle flask. The mixture was heated up to reflux under nitrogen for 24 hours. The reaction mixture was purified on silica gel with 50% methylene chloride in hexane. About 900 mg product was separated from the reaction mixture which containing four ligand-scrambled iridium complexes. The product was confirmed by LC-MS. The desired fraction can be obtained through column chromatography.

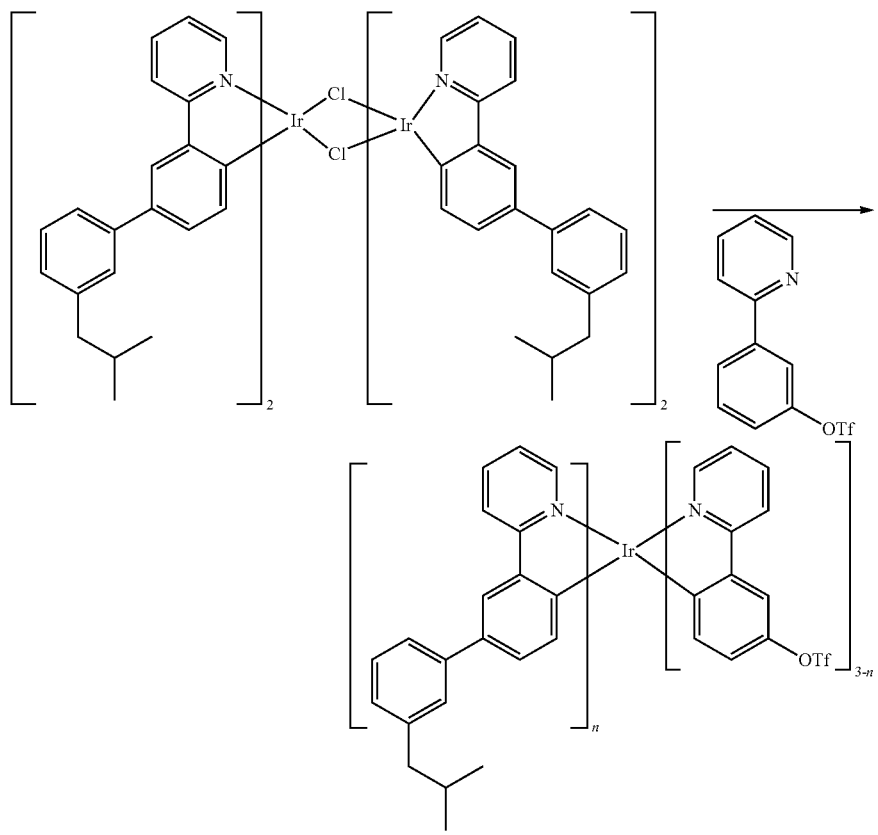

n = 0, 1, 2, 3

700 mg (0.647 mmol) of the triflate iridium complex, 394 mg (3.23 mmol) phenylboronic acid, 60 mg $Pd_2(dba)_3$ (0.065 mmol), 110 mg (0.268 mmol) S-Phos, 840 mg (3.65 mmol) $K_3PO_4 \cdot H_2O$ and 50 ml dry toluene were charged in a 100 ml three-necked flask. The reaction mixture was bubbled nitrogen for 30 minutes then heated up to reflux for 20 hours under nitrogen. The reaction mixture was separated on silica gel column. 610 mg solid (99% yield) was obtained, as confirmed by NMR and LC-MS.

Compound 36

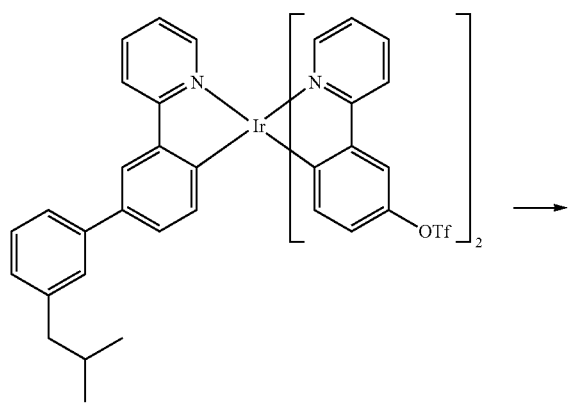

-continued

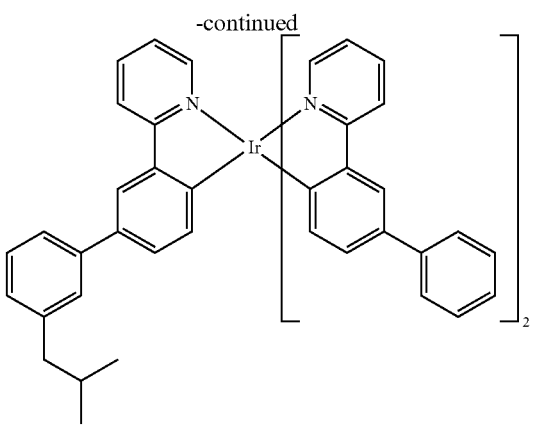

All devices are fabricated by high vacuum ($<10^{-7}$ Torr) thermal evaporation. The anode electrode is ~1200 Å of indium tin oxide (ITO). The cathode consists of 10 Å of LiF followed by 1,000 Å of Al. All devices are encapsulated with a glass lid sealed with an epoxy resin in a nitrogen glove box (<1 ppm of $H_2O$ and $O_2$) immediately after fabrication, and a moisture getter was incorporated inside the package.

All device examples have organic stacks consisted of sequentially, from the ITO surface, 100 Å thick of copper phthalocyanine (CuPc) or Compound A as the hole injection layer (HIL), 300 Å of 4,4'-bis[N-(1-naphthyl)-N-phenylamino]biphenyl (α-NPD), as the hole transporting layer (HTL), 300 Å of 4,4'-bis(N-carbazolyl)biphenyl (CBP), Compound G or Compound H doped with 6-10 wt % of the dopant emitter (invention compounds and comparative compounds) as the emissive layer (EML). The electron transporting layers (ETL) consisted of 50 Å of HTP as the ETL2 and 450 Å of tris(8-hydroxyquinolinato)aluminum ($Alq_3$) as the ETL1, or 100 Å of Compound H as the ETL2 and 400 Å of $Alq_3$ as the $ETL_1$. The current-voltage-luminance (IVL) characteristics, electroluminescence properties [emission maximum ($Em_{max}$), full width at half maximum (FWHM) and CIE coordinates] and operational lifetimes are measured and summarized in the Table 1. A typical display brightness level of 1000 cd/m$^2$ for green emitting devices is chosen for the comparison between different devices. For device operation stability, all device examples and comparative device examples were tested at a constant current density (J) of 40 mA/cm$^2$ at room temperature. The initial brightness ($L_0$) at J=40 mA/cm$^2$ at room temperature is provided in the Table 1.

Particular devices are provided wherein Compound 1 or Compound 35 is the emissive dopant and Compound H or Compound G is the host.

As used herein, the following compounds have the following structures:

Compound 35

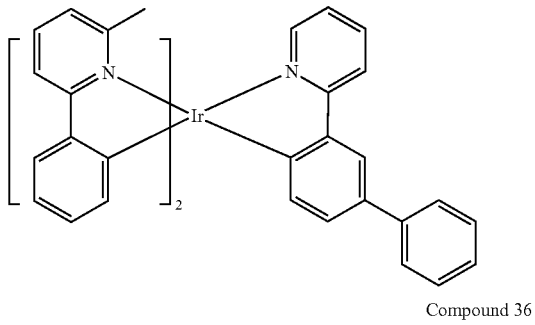

Compound 36

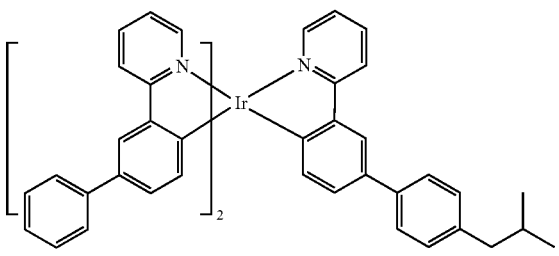

Compound A

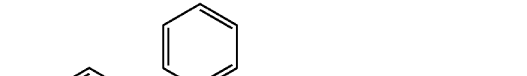

Compound B

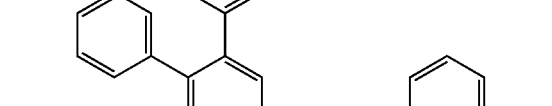

Compound C

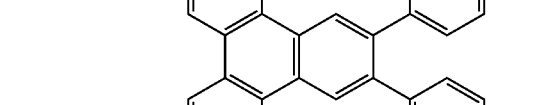

Compound D

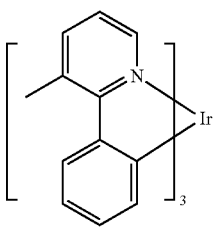

HPT

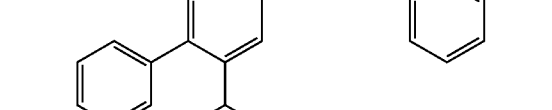

Compound G

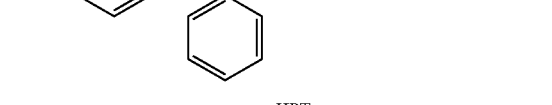

Compound H

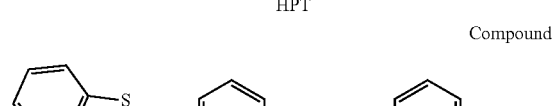

Particular emissive dopants for the emissive layer of an OLED are also provided which may lead to devices having particularly good properties. Specifically, devices having an emissive layer using Compounds 25 or 26 as the emissive dopant as shown in Table 1. Devices using Compound 25 and 26 respectively as emitters show improved device stability indicating that alkylphenyl substitutions may be beneficial. Cmpd. is an abbreviation of Compound.

Particular Ir(6-alkylppy) type compounds are provided which may lead to devices having particularly narrow luminescence linewidth. Specifically, devices using heteroleptic Compounds 35 or 11 as an emissive dopant as shown in Table 1. It is believed that a substitution at the 6-position has this effect because it exerts a steric effect on the Ir complex, resulting in a relatively longer N—Ir bond, which translates to a narrower emission. Thus having an Ir(ppy) compounds

TABLE 1

| Device Example | Cmpd. | Doping % | HIL | Host | ETL2 | $T_{evap}$ (°C.) at 0.2 Å/s | $Em_{max}$ (nm) | FWHM (nm) | CIE x | CIE y | V(V) | LE (cd/A) | EQE (%) | PE (lm/W) | $L_0$ (cd/m²) | $T_{80\%}$ (hr) |
|---|---|---|---|---|---|---|---|---|---|---|---|---|---|---|---|---|
| Comparative 1 | Ir(ppy) | 9 | A | CBP | HPT | 230 | 515 | 74 | 0.315 | 0.620 | 5.8 | 50.2 | 14.2 | 27.2 | 13,750 | 59 |
| 1 | 25 | 10 | A | CBP | HPT | 237 | 521 | 68 | 0.326 | 0.626 | 6.6 | 55.7 | 15.2 | 26.5 | 13,913 | 83 |
| 2 | 26 | 10 | A | CBP | HPT | 237 | 521 | 70 | 0.330 | 0.624 | 6.1 | 59.1 | 16.1 | 30.4 | 15,917 | 90 |
| 3 | 27 | 10 | A | CBP | HPT | 236 | 521 | 79 | 0.346 | 0.609 | 8.7 | 36.7 | 10.2 | 13.2 | 9,493 | 47 |
| Comparative 2 | B | 10 | A | CBP | HPT | 240 | 512 | 74 | 0.307 | 0.619 | 5.5 | 59 | 16.9 | 33.7 | 15,535 | 63 |
| 4 | 3 | 10 | A | CBP | HPT | 240 | 517 | 74 | 0.321 | 0.618 | 5.4 | 59.8 | 16.9 | 34.8 | 15,572 | 47 |
| Comparative 3 | C | 6 | CuPc | CBP | HPT | 240 | 514 | 72 | 0.3013 | 0.6292 | 7.3 | 41.4 | 11.6 | 17.8077 | 10,970 | 12 |
| 5 | 6 | 10 | A | CBP | HPT | 262 | 519 | 72 | 0.322 | 0.624 | 5.5 | 58.5 | 16.2 | 33.4 | 16,582 | 46 |
| Comparative 4 | D | 10 | A | CBP | HPT | 213 | 507 | 68 | 0.294 | 0.635 | 5.8 | 44.2 | 13.1 | 23.9 | 13,930 | 14 |
| 6 | 35 | 30 | A | CBP | HPT | 246 | 517 | 68 | 0.317 | 0.625 | 5.8 | 56.2 | 15.6 | 30.4 | 15,369 | 18 |
| 7 | 35 | 10 | A | H | H | 246 | 519 | 69 | 0.316 | 0.625 | 6.5 | 52.1 | 14.5 | 25.2 | 14,985 | 85 |
| 8 | 11 | 10 | A | H | H | 241 | 512 | 66 | 0.298 | 0.626 | 6.5 | 48.1 | 13.7 | 23.2 | 13,115 | 38 |
| 9 | 17 | 10 | A | CBP | HPT | 211 | 518 | 74 | 0.314 | 0.625 | 6.2 | 22.7 | 6.3 | 11.5 | 9,216 | 7 |
| 10 | 18 | 10 | A | CBP | HPT | 221 | 519 | 71 | 0.321 | 0.626 | 6.2 | 26.6 | 7.4 | 13.5 | 10,085 | 3 |
| 11 | 1 | 10 | A | CBP | HPT | 207 | 513 | 76 | 0.312 | 0.619 | 5.8 | 36.3 | 10.3 | 19.7 | 11,430 | 14 |
| 12 | 2 | 10 | A | CBP | HPT | 205 | 519 | 74 | 0.32 | 0.623 | 5.5 | 43.6 | 12.2 | 24.9 | 12,976 | 14 |
| 13 | 34 | 10 | A | H | H | 235 | 520 | 69 | 0.328 | 0.624 | 6.7 | 49.4 | 13.5 | 23.2 | 13,402 | 34 |
| 14 | 29 | 10 | A | H | H | 279 | 522 | 71 | 0.327 | 0.621 | 7.9 | 44.0 | 12.0 | 17.5 | 12,335 | 200 |
| 15 | 16 | 10 | A | H | H | 227 | 507 | 76 | 0.305 | 0.604 | 6.4 | 40.4 | 12.2 | 19.8 | 10,719 | 30 |
| 16 | 35 | 10 | A | G | H | 230 | 516 | 70 | 0.313 | 0.625 | 6.6 | 56 | 15.7 | 26.6 | 15,555 | 210 |
| 17 | 11 | 10 | A | G | H | 235 | 511 | 65 | 0.290 | 0.630 | 6.1 | 56.3 | 16.1 | 29.0 | 16,151 | 117 |

The alkyl substitution on the 5'-phenyl can be used to tune evaporation temperature and solubility, narrow emission, and increase device efficiency. The heteroleptic nature of Compounds 25 and 26, with only one of the 2-phenylpyridine substituted keeps the evaporation temperature low as shown in Table 1, which is important for OLED manufacturing because prolonged heating of the materials is needed, and low evaporation temperature translates to less thermal stress which typically results in cleaner evaporations. The alkyl substitution on the 5'-phenyl can also increase solubility as shown in Table 1, which is critical in device fabrication based on solution processes, such as inkjet printing. 5' alkylphenyl may also narrow emission which is preferred in OLED for display application because more saturated color can be achieved. In addition, devices using Compounds 25 and 26 demonstrate that using heteroleptic complexes may offer high device efficiency.

Similarly, devices having an emissive layer using heteroleptic Compounds 6, 35, 11, 18 or 2 as the dopant may lead to devices having particularly good properties. Specifically, devices having an emissive layer using Compound 6 as the dopant, an emissive layer with Compound 35 as a dopant, an emissive layer with Compound 35 as a dopant and Compound H as the host, an emissive layer with Compound 11 as the dopant and Compound H as the host, an emissive layer with Compound 18 as a dopant, and/or an emissive layer with Compound 2 as a dopant. Such devices often have one or more improvements in device stability, luminescence linewidth or device efficiency as shown in Table 1.

have a 6-alkyl group and with a heteroleptic nature is particularly useful in achieving narrow luminescence linewidth and improved device stability without much increase in evaporation temperature as compared to the homoleptic counterpart.

Table 1 is a summary of the device data. Comparative Example 1 and Device Examples 1-2 have the same device structure except that Comparative Example 1 uses Ir(ppy)$_3$ as the emitter whereas Device Examples 1-3 use Compounds 25 and 26 respectively as the emitters. Compound 25 has a isobutylphenyl and 26 has a methylphenyl at the 5'-position. Comparative Example 1 and Device Examples 1-2 have $T_{80\%}$ (defined as the time taken for the initial luminance, $L_O$, to drop to 80% of its initial luminance) of 59, 83 and 90 hours respectively. The result indicates that alkylphenyl substitutions may be beneficial to device stability as postulated in US20050119485A1. However, the heteroleptic nature of Compounds 25 and 26, with only one of the 2-phenypyridine substituted, keeps the evaporation temperature low, only a few ° C. high than Ir(ppy)$_3$. Low evaporation temperature is important for OLED manufacturing because prolonged heating of the materials is needed, and low evaporation temperature translates to less thermal stress which typically results in cleaner evaporations. The alkyl substitution on the 5'-phenyl can be further used to tune evaporation temperature and solubility. Having high solubility is critical in device fabrication based on solution processes such as inkjet printing. The result also shows that the 5'-alkylphenyl may narrow the emission. Comparative Example 1 has a FWHM of 74 nm whereas Device Examples 1 and 2 have FWHM of 68 and 70 nm respectively. Narrow emission is preferred in OLED for display application because more saturated color can be achieved. In addition, Comparative Example 1 and Device Examples 1 and 2 have device efficiency of 50, 56 and 59 cd/A respectively at 1000 cd/m². This indicates the using heteroleptic complexes may offer high device efficiency.

More comparisons of homoleptic and heteroleptic based on structurally similar ligands can be found in Table 1. Comparative Example 2 (with the homoleptic Compound B) and Device Example 4 (with the heteroleptic Compound 3) have $T_{80\%}$ of 63 and 47 hours respectively. The FWHM are both 74 nm and device efficiency are both about 60 cd/A. In this case, the heteroleptic nature does not provide a benefit. Comparative Example 3 (with the homoleptic Compound C, disclosed in WO06014599A2) and Device Example 5 (with the heteroleptic Compound 6) have $T_{80\%}$ of 12 and 46 hours respectively. The FWHM are both 72 nm, and device efficiency are 41 and 59 cd/A respectively. In this case, the heteroleptic nature provides benefits to the device stability and efficiency. Comparative Example 4 (with the homoleptic Compound D, disclosed in WO06014599A2), Device Example 6 (with the heteroleptic Compound 35), Device Example 7 (with the heteroleptic Compound 35 and Compound H as the host) and Device Example 8 (with the heteroleptic Compound 11 and Compound H as the host) have $T_{80\%}$ of 14, 18, 85 and 38 hours respectively. The FWHM are 68, 68, 69 and 66 nm, and device efficiency are 44, 52, 52 and 48 cd/A respectively. In this case, the heteroleptic nature provides benefits to the device stability. Comparative Example 9 (with the homoleptic Compound 17) and Device Example 10 (with the heteroleptic Compound 18) have $T_{80\%}$ of 7 and 3 hours respectively. The FWHM are 74 and 71 nm, and device efficiency are about 23 and 27 cd/A respectively. In this case, the heteroleptic nature provides benefits to the luminescence linewidth and device efficiency. Comparative Example 11 (with the homoleptic Compound 1) and Device Example 12 (with the heteroleptic Compound 2) both have $T_{80\%}$ of 4 hours. The FWHM are 76 and 74 nm, and device efficiency are about 35 and 44 cd/A respectively. In this case, the heteroleptic nature provides benefits to the luminescence linewidth and device efficiency. Summarizing the device result, there is often one or more improvements in device stability, luminescence linewidth or device efficiency based on devices using the heteroleptic analogs as the dopant emitters.

The Ir(6-alkylppy) type complexes have particularly narrow luminescence linewidth. Device Examples 6, 7 and 8 have FWHM of 68, 69 and 66 nm respectively. It is believed that a substitution at the 6-position has this effect because it exerts a steric effect on the Ir complex, resulting in a relatively longer N—Ir bond, which translates to a narrower emission. Thus having an Irppy complex have a 6-alkyl group and with a heteroleptic nature is particularly useful in achieving narrow luminescence linewidth and improved device stability without much increase in evaporation temperature compared to the homoleptic counterpart.

As seen from Table 1, the host and ETL2 materials may also be important in affecting the device performance and lifetime. For instance, Device Example 6 uses Compound 35 as the emitter, CBP as the host and HTP as the ETL2, Device Example 7 uses Compound 35 as the emitter, Compound H as the host and Compound H as the ETL2 and Device Example 16 uses Compound 35 as the emitter, Compound G as the host and Compound H as the ETL2. The efficiencies are 56, 52 and 56 cd/A, respectively. $T_{80\%}$ are 18, 85 and 210 hours at about $L_0$=15000 cd/m², respectively. The FWHM are 68, 69 and 70 nm, respectively. The CIE are (0.317, 0.625), (0.316, 0.625) and (0.313, 0.625), respectively. While the efficiency, FWHM and CIE are similar, devices with Compound H and Compound G as the host have improved lifetime by about 5 and 12 times respectively compared to devices with CBP as the host. Similarly, Device Example 8 uses Compound 11 as the emitter, Compound H as the host and Compound H as the ETL2 and Device Example 17 uses Compound 11 as the emitter, Compound G as the host and Compound H as the ETL2. The efficiencies are 48 and 56 cd/A, respectively. To are 38 hours at $L_0$=13000 cd/m² and 117 hours at L=16000 cd/m², respectively. The FWHM are 66 and 65 nm, respectively. The CIE are (0.298. 0.626) and (0.290, 0.630), respectively. In this case, the use of Compound G as a host improves the efficiency and CIE slightly, and improves the device lifetime by at least 3 times compared to the device with Compound H as the host. Compound H, based on triphenylene compounds as phosphorescent OLED hosts (U.S. Application No. 61/017,506) may be advantageous over carbazole as a host. Furthermore, Compound G, based on dibenzothiophene compounds as phosphorescent OLED hosts (U.S. Application No. 61/017,480) may be advantageous as a host. Using a triphenylene host and triphenylene ETL2 combination may be particularly advantageous. Using a dibenzothiophene host and triphenylene ETL2 combination may be even more advantageous.

The synthesis of Irppy complex having a 6-alkyl group by the direct complexation of the ligand with Ir(acac)₃ may be difficult. For example, the synthesis of the intermediate I in the preparation of Compound 11 was reported in WO 2006/014599A2. The direct complexation of the ligand with Ir(acac)₃ yielded only 5.4% of the intermediate I. However, in the preparation of Compound 11, Intermediate I is synthesized through the Ir(L)₂ᵗBuacac. The yield of the final step is significantly better (74%). Similarly, Compound 17 and Compound 32 was synthesized through the Ir(L)₂ᵗBuacac route in an improved yield compared to the direct complexation method. Without being bound by theory, it is believed that the tBuacac ligand is a better leaving group than the acac ligand, resulting in an easier displacement by the third ligand in the formation of the tris Ir complex. This method provides a synthesis for high yield of tris complexes having photoactive sterically demanding cyclometallated ligands for use in OLEDs.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:
1. An organic light emitting device comprising:
  an anode;
  a cathode; and
  an emissive organic layer, disposed between the anode and the cathode, the emissive organic layer comprising a host selected from

Compound H
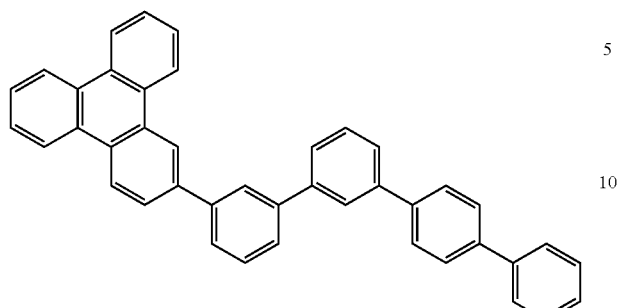
and
Compound G
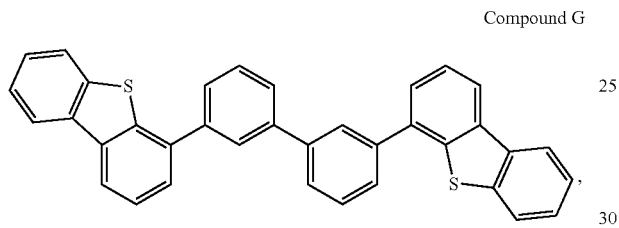
and an iridium compound selected from the group consisting of:
Compound 1
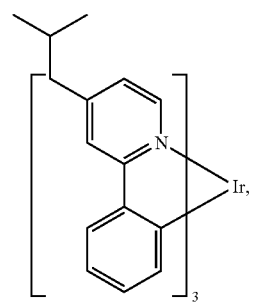
Compound 4
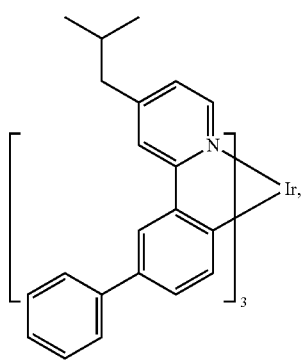
Compound 5
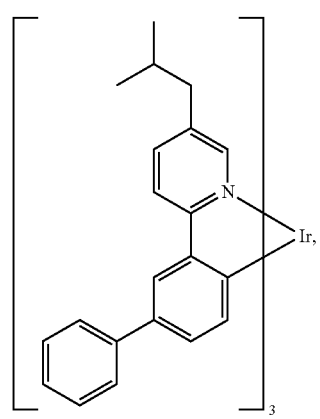
Compound 7
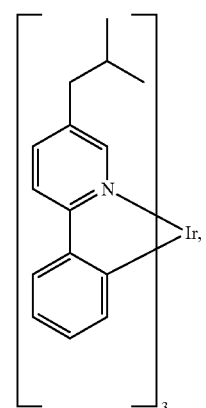
Compound 9
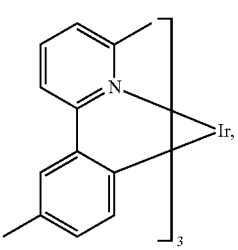
Compound 13
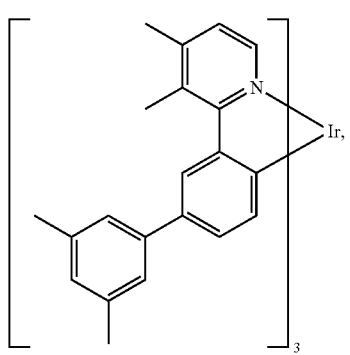

Compound 14
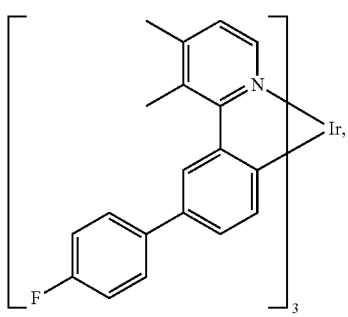
Compound 15
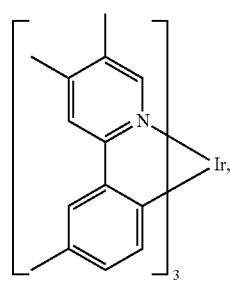
Compound 16
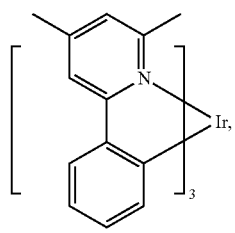
Compound 17
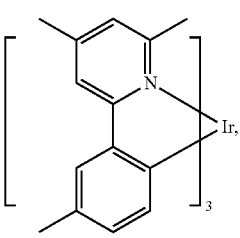
Compound 19
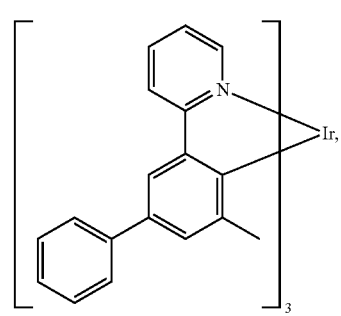
Compound 20
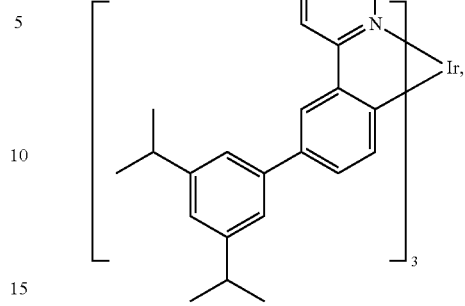
Compound 21
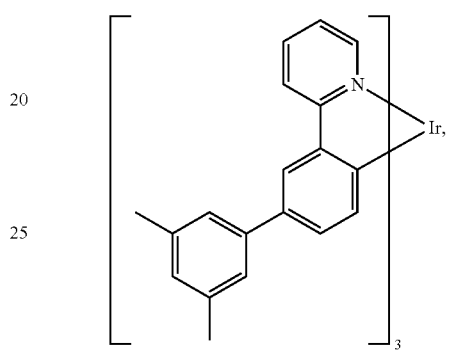
Compound 22
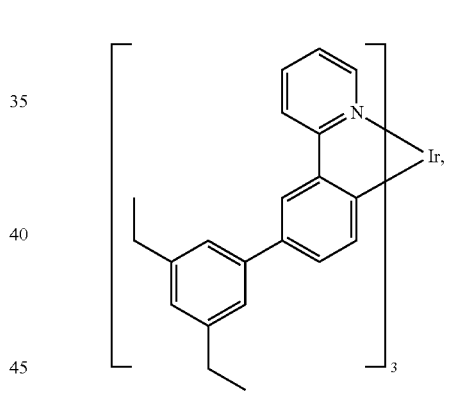
Compound 23
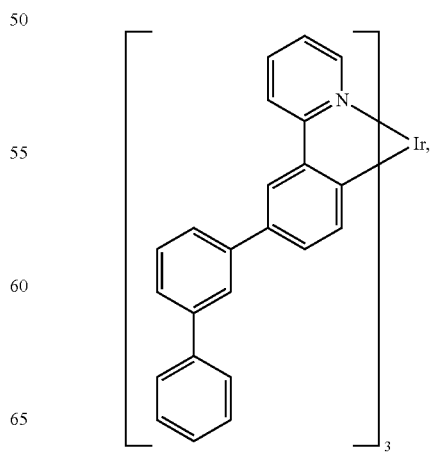

Compound 24
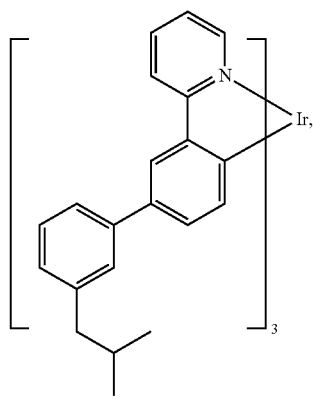
Compound 28
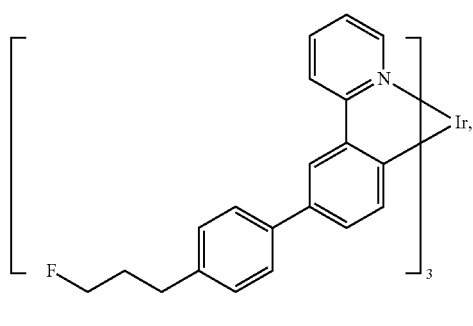
Compound 29
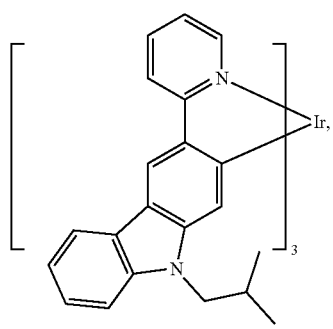
Compound 30
Compound 31
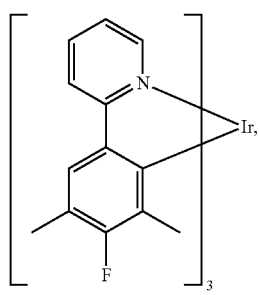
Compound 32
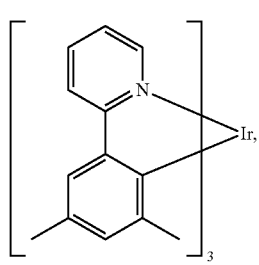
Compound 33
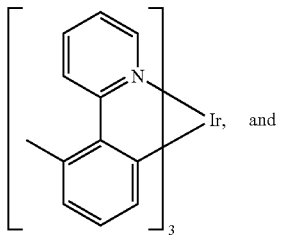
and
Compound 34
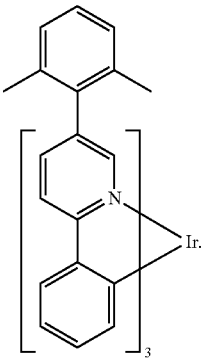
2. The device of claim 1, wherein the iridium compound is an emissive dopant.

3. The device of claim 1, wherein the host is
Compound H
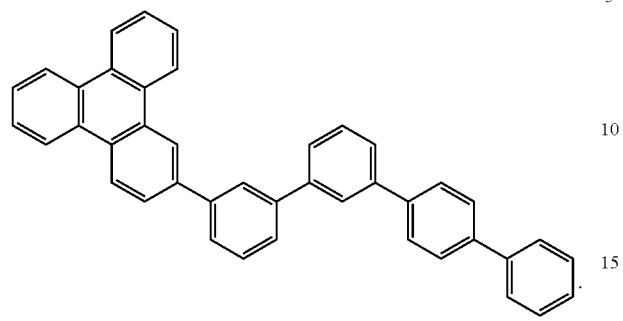
4. The device of claim 1, wherein the host is
Compound G
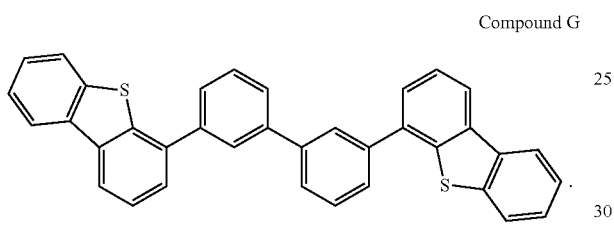
5. The device of claim 1, wherein the iridium compound is selected from the group consisting of
Compound 28
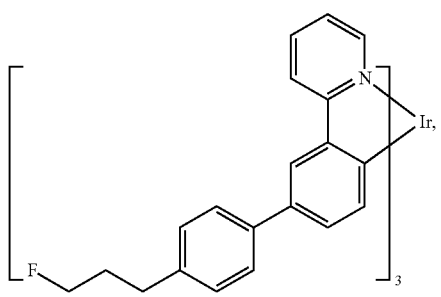
Compound 30
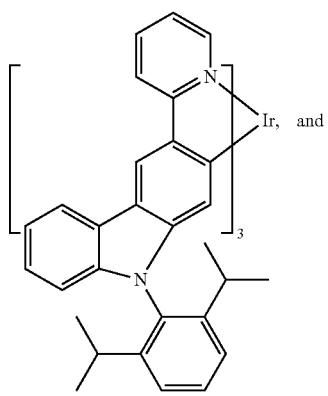
, and
-continued
Compound 34
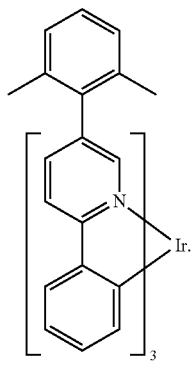
6. The device of claim 1, wherein the iridium compound is
Compound 28
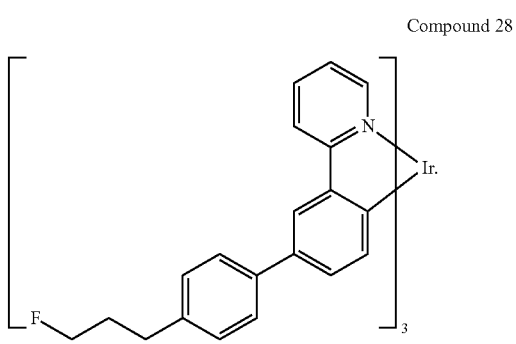
7. The device of claim 1, wherein the iridium compound is
Compound 30
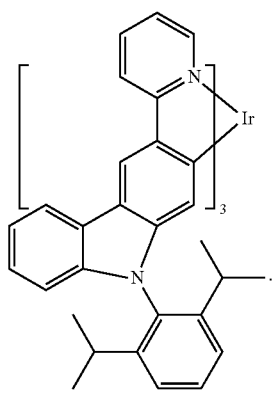

8. The device of claim 1, wherein the iridium compound is
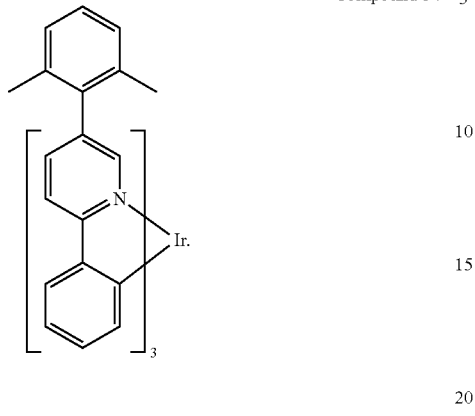
Compound 34
* * * * *

UNITED STATES PATENT AND TRADEMARK OFFICE
CERTIFICATE OF CORRECTION

PATENT NO. : 9,899,612 B2
APPLICATION NO. : 14/295696
DATED : February 20, 2018
INVENTOR(S) : Raymond Kwong et al.

It is certified that error appears in the above-identified patent and that said Letters Patent is hereby corrected as shown below:

In the Specification

Column 10, Line 40, please insert the word --aryl,-- after the word halo.

Column 10, Line 41, please delete the word "a" before the words heteroaryl, substituted aryl.

Signed and Sealed this
Fifteenth Day of May, 2018

Andrei Iancu
*Director of the United States Patent and Trademark Office*